US007470522B1

(12) United States Patent
Ryan

(10) Patent No.: US 7,470,522 B1
(45) Date of Patent: Dec. 30, 2008

(54) ISOLATED GENOMIC POLYNUCLEOTIDE FRAGMENTS ENCODING HUMAN RESISTIN AND THE HUMAN SYNTAXIN BINDING PROTEIN 2

(75) Inventor: James W. Ryan, Augusta, GA (US)

(73) Assignee: Ryogen LLC, Suffern, NY (US)

( * ) Notice: Subject to any disclaimer, the term of this patent is extended or adjusted under 35 U.S.C. 154(b) by 0 days.

(21) Appl. No.: 11/483,373

(22) Filed: Jul. 7, 2006

Related U.S. Application Data

(60) Provisional application No. 60/697,815, filed on Jul. 9, 2005.

(51) Int. Cl.
*C12P 21/06* (2006.01)
*C07H 17/00* (2006.01)
*C07K 14/00* (2006.01)

(52) U.S. Cl. .................. 435/69.1; 536/23.1; 435/320.1; 435/325; 435/252.3; 530/350

(58) Field of Classification Search ............... 536/23.1; 435/69.1, 320.1, 253.2, 325; 530/350
See application file for complete search history.

(56) References Cited

OTHER PUBLICATIONS

Darnell et al. 1986; Molecular Cell Biology, p. 373.*
McTernan et al. 2002; Increased resistin gene and protein expression in human abdominal adipose tissue. J. Clinical Endocrinology & Metabolism 87(5): 2407-2410.*
Chumakov et al., "C/EBP regulation of XCP/FIZZ/resistin genes", RH PubMed Accession No. AF352730, submitted Feb. 23, 2001, bases 1-4922.
Steppan et al., 2001, "The hormone resistin links obesity to diabetes", Nature 409:307-312.
Holcomb et al., "*Homo sapiens* cysteine-rich secreted protein (FIZZ3) mRNA, complete cds.", PubMed Accession No. AF205952, submitted Aug. 28, 2000, bases 1 to 457.
Waterston et al., "*Homo sapiens* chromosome 19 clone RP11-492L14", PubMed Accession No. AC021153, submitted Jan. 14, 2000, bases 1 to 155645.
DOE Joint Genome Institute and Stanford Human Genome Center, "*Home sapiens* chromosome 19 clone CTD-3214H19", PubMed Accession No. AC008763, submitted Aug. 3, 1999, bases 1 to 177062.
Altschul et al., 1997, "Gapped BLAST and PSI-BLAST: a new generation of protein database search programs", Nucl. Acids Res. 25:3389-3402.
Burge et al., 1997, "Prediction of Complete Genome Structures in Human Genomic DNA", 268:78-94.
Ziegler et al., 1996, "Molecular Characterization of a Nonneuronal Human UNC18 Homolog", Genomics 37:19-23.
Katagiri et al., 1995, "A Novel Isoform of Syntaxin-binding Protein Homologous to Yeast Sec1 Expressed Ubiquitously in Mammalian Cells", J. Biol. Chem. 270:4963-4966.
"*Homo sapiens* syntaxin binding protein 2 (STXBP2), mRNA", PubMed Accession No. NM_006949, bases 1 to 1815 (multiple submissions-earliest submission 1995).

* cited by examiner

*Primary Examiner*—Karen Cochrane Carlson
(74) *Attorney, Agent, or Firm*—Cheryl H. Agris

(57) ABSTRACT

The invention is directed to isolated genomic polynucleotide fragments that encode human resistin and human syntaxin binding protein 2, vectors and hosts containing these fragments and fragments hybridizing to noncoding regions as well as antisense oligonucleotides to these fragments. The invention is further directed to methods of using these fragments to obtain human resistin and human syntaxin binding protein 2 and to diagnose, treat, prevent and/or ameliorate a pathological disorder.

16 Claims, No Drawings

ISOLATED GENOMIC POLYNUCLEOTIDE FRAGMENTS ENCODING HUMAN RESISTIN AND THE HUMAN SYNTAXIN BINDING PROTEIN 2

PRIORITY CLAIM

This application claims priority to application Ser. No. 60/697,815, filed Jul. 9, 2005, the contents of which are herein incorporated by reference.

FIELD OF THE INVENTION

The invention is directed to isolated genomic polynucleotide fragments that encode human resistin and human syntaxin binding protein 2, vectors and hosts containing these fragments and fragments hybridizing to noncoding regions as well as antisense oligonucleotides to these fragments. The invention is further directed to methods of using these fragments to obtain human resistin and human syntaxin binding protein and to diagnose, treat, prevent and/or ameliorate a pathological disorder.

BACKGROUND OF THE INVENTION

Chromosome 19 p 13.3-p 13.2 contains genes encoding, for example, zinc-finger protein 14, oncogene VAV1, tartrate-resistant acid phosphatase, bone marrow stromal cell antigen, calponin 1 and syntaxin binding protein 2; the last of which is discussed in detail below. The gene that encodes resistin, is known to be disposed on chromosome 19.

Human Resistin

Human resistin is a protein that interferes with the actions of insulin on liver and muscle. It is disposed largely in white adipose tissue and in crypt epithelium of the intestine. Given its disposition in fatty tissue and its inhibition of insulin effects, resistin is believed to link obesity to type 2 diabetes (Steppan et al., Nature 409: 307-312, 2001). Consistent with this view, antibodies to resistin improve blood sugar levels and insulin actions in mice with diet-induced obesity. Conversely, administration of recombinant resistin impairs glucose tolerance and insulin actions. The resistin cDNA is identical to the cDNAs for entities called FIZZ3, accession number AF205952, and C/EBP-epsilon regulated myeloid-specific secreted cysteine-rich protein precursor, accession number AF352730. The latter sequence contains the intron sequences and some 5'- and 3'-sequences.

Human Syntaxin Binding Protein 2

Human syntaxin binding protein, a member of the STXBP/unc-18/Sec1 protein family, is disposed largely in placenta, lung, liver, kidney, peripheral lymphocytes and pancreas. It is believed to play a role in vesicular transport between the golgi apparatus and the cell membrane in non-neuronal tissues. Mouse syntaxin binding protein 2-binds to syntaxins 1A, 2 and 3 but not to syntaxin 4 (Katagiri et al., J. Biol. Chem. 270: 4963-6, 1995). The human gene is upregulated in interleukin-2 activated natural killer cells (Ziegler et al., Genomics 37: 19-23, 1996). The cDNA has been determined (see accession number NM_006949).

OBJECTS OF THE INVENTION

Although cDNAs encoding the above-disclosed proteins have been isolated, their locations on chromosome 19 have not been determined. Furthermore, genomic nucleic acids encoding these polypeptides have not been isolated. Noncoding sequences play a significant role in regulating the expression of polypeptides as well as the processing of RNA encoding these polypeptides.

There is clearly a need for obtaining genomic polynucleotide sequences encoding these polypeptides. Therefore, it is an object of the invention to isolate such genomic polynucleotide sequences.

SUMMARY OF THE INVENTION

The invention is directed to isolated genomic nucleic acid molecules or polynucleotides, said polynucleotides obtainable from human chromosome 19 comprising a naturally occurring polynucleotide sequence at least 95% identical to a sequence selected from the group consisting of:

(a) a forward or reverse strand of a nucleic acid molecule encoding a polypeptide selected from the group consisting of human resistin depicted in SEQ ID NO: 1 and/or human syntaxin binding protein 2 depicted in SEQ ID NO:2 or variant of SEQ ID NO: 1 or SEQ ID NO:2;

(b) a forward or reverse strand of a nucleic acid molecule containing SEQ ID NO:3 which encodes human resistin depicted in SEQ ID NO: 1 and/or SEQ ID NO:4 which encodes human syntaxin binding protein 2 depicted in SEQ ID NO:2 or variant of SEQ ID NO:3 and/or SEQ ID NO:4;

(c) a forward or reverse strand of a nucleic acid molecule at least 20 nucleotides in length unique to a noncoding region(s) of SEQ ID NO: 3 or 4, preferably about 20-35,000 in length;

(d) a forward or reverse strand of a nucleic acid molecule at least 60 nucleotides in length unique to a contiguous coding and noncoding nucleic acid sequence(s) of SEQ ID NO:3 or 4, preferably about 60-35,000 nucleotides in length;

(e) a nucleic acid molecule or its reverse strand that extends from the 5'-end of SEQ ID NO:3 through the 3'-end of SEQ ID NO:4 as depicted in SEQ ID NO:5;

(f) a nucleic acid molecule which hybridizes to any one of the nucleic acid molecules specified in (a)-(b) and as well as nucleic acid constructs, expression vectors and host cells containing these polynucleotide sequences.

The polynucleotides of the present invention may be used for the manufacture of a gene therapy for the prevention, treatment or amelioration of a medical condition by adding an amount of a composition comprising said polynucleotide effective to prevent, treat or ameliorate said medical condition.

The invention is further directed to obtaining these polypeptides by:

(a) culturing host cells comprising these sequences under conditions that provide for the expression of said polypeptide and (b) recovering said expressed polypeptide.

The polypeptides obtained may be used to produce antibodies by (a) optionally conjugating said polypeptide to a carrier protein;

(b) immunizing a host animal with said polypeptide or peptide-carrier protein conjugate of step (b) with an adjuvant and (c) obtaining antibody from said immunized host animal.

The nucleic acid molecules of the present invention may be used for the manufacture of a medicament for prevention, treatment or amelioration of a medical condition. In a specific embodiment, the noncoding regions are transcription regulatory regions. The transcription regulatory regions may be used to produce a heterologous peptide by expressing in a host cell, said transcription regulatory region operably linked to a polynucleotide encoding the heterologous polypeptide and recovering the expressed heterologous polypeptide.

The polynucleotides of the present invention may be used to diagnose a pathological condition in a subject comprising (a) determining the presence or absence of a mutation in the polynucleotides of the present invention and (b) diagnosing a pathological condition or a susceptibility to a pathological condition based on the presence or absence of said mutation.

The invention is further directed to kits and/or microarrays comprising the nucleic acids of the present invention. The kits may comprise microarrays. Furthermore, the kits of the present invention may comprise other sequences, e.g., cDNA sequences.

DEFINITIONS

In accordance with the present invention there may be employed conventional molecular biology, microbiology, and recombinant DNA techniques within the skill of the art. Such techniques are explained fully in the literature. See, e.g., Sambrook et al, 2001, "Molecular Cloning: A Laboratory Manual"; Ausubel, ed., 1994, "Current Protocols in Molecular Biology" Volumes I-III; Celis, ed., 1994, "Cell Biology: A Laboratory Handbook" Volumes I-III; Coligan, ed., 1994, "Current Protocols in Immunology" Volumes I-III; Gait ed., 1984, "Oligonucleotide Synthesis"; Hames & Higgins eds., 1985, "Nucleic Acid Hybridization"; Hames & Higgins, eds., 1984, "Transcription And Translation"; Freshney, ed., 1986, "Animal Cell Culture"; IRL Press, 1986, "Immobilized Cells And Enzymes"; Perbal, 1984, "A Practical Guide To Molecular Cloning."

Where a range of values is provided, it is understood that each intervening value, to the tenth of the unit of the lower limit unless the context clearly dictates otherwise, between the upper and lower limit of that range and any other stated or intervening value in that stated range is encompassed within the invention.

Unless defined otherwise, all technical and scientific terms used herein have the same meaning as commonly understood by one of ordinary skill in the art to which this invention belongs. Although any methods and materials similar or equivalent to those described herein can also be used in the practice or testing of the present invention, the preferred methods and materials are now described.

It must be noted that as used herein and in the appended claims, the singular forms "a," "and" and "the" include plural references unless the context clearly dictates otherwise. The terms "polynucleotide(s)", "nucleic acid molecule(s)" and "nucleic acids" will be used interchangeably.

Furthermore, the following terms shall have the definitions set out below.

As defined herein "isolated" refers to material removed from its original environment and is thus altered "by the hand of man" from its natural state.

The amino acid residues described herein are preferred to be in the "L" isomeric form. However, residues in the "D" isomeric form can be substituted for any L-amino acid residue, as long as the desired functional is retained by the polypeptide. $NH_2$ refers to the free amino group present at the amino terminus of a polypeptide. COOH refers to the free carboxy group present at the carboxy terminus of a polypeptide.

"Nucleic acid construct" is defined herein, is a nucleic acid molecule, either single- or double-stranded, which is isolated from a naturally occurring gene or which has been modified to contain segments of nucleic acid which are combined and juxtaposed in a manner which would not otherwise exist in nature. The term nucleic acid construct is synonymous with the term "expression cassette" when the nucleic acid construct contains all the control sequences required for expression of a coding sequence of the present invention.

The term "coding sequence" is defined herein as a portion of a nucleic acid sequence which directly specifies the amino acid sequence of its protein product. The boundaries of the coding sequence are generally determined by a ribosome binding site (prokaryotes) or by the ATG start codon (eukaryotes) of the first open reading frame at the 5'-end of the mRNA and a transcription terminator sequence located just downstream of the open reading frame at the 3'-end of the mRNA. A coding sequence can include, but is not limited to, DNA, cDNA, and recombinant nucleic acid sequences.

A "heterologous" region of a recombinant cell is an identifiable segment of nucleic acid within a larger nucleic acid molecule that is not found in association with the larger molecule in nature.

An "expression vector" may be any vector (e.g., a plasmid or virus) which can be conveniently subjected to recombinant DNA procedures and can bring about the expression of the nucleic acid sequence.

An "origin of replication" refers to those DNA sequences that participate in DNA synthesis.

An "expression control sequence" is a DNA sequence that controls and regulates the transcription and translation of another DNA sequence. A coding sequence is "under the control" of transcriptional and translational control sequences in a cell when RNA polymerase transcribes the coding sequence into mRNA, which is then translated into the protein encoded by the coding sequence. Transcriptional and translational control sequences are DNA regulatory sequences, such as promoters, enhancers, polyadenylation signals, terminators, and the like, that provide for the expression of a coding sequence in a host cell.

A "signal sequence" can be included before the coding sequence of the mature polypeptide. This sequence encodes a signal peptide, N-terminal to the mature polypeptide, that communicates to the host cell to direct the polypeptide to the cell surface or secrete the polypeptide into the media, and this signal peptide is clipped off by the host cell before the protein leaves the cell. Signal sequences can be found associated with a variety of proteins native to prokaryotes and eukaryotes.

A cell has been "transformed" by exogenous or heterologous DNA when such DNA has been introduced inside the cell. The transforming DNA may or may not be integrated (covalently linked) into chromosomal DNA making up the genome of the cell. In prokaryotes, yeast, and mammalian cells for example, the transforming DNA may be maintained on an episomal element such as a plasmid. With respect to eukaryotic cells, a stably transformed cell is one in which the transforming DNA has become integrated into a chromosome so that it is inherited by daughter cells through chromosome replication. This stability is demonstrated by the ability of the eukaryotic cell to establish cell lines or clones comprised of a population of daughter cells containing the transforming DNA.

It should be appreciated that also within the scope of the present invention are nucleic acid sequences encoding the polypeptide(s) of the present invention, which code for a polypeptide having the same amino acid sequence as the sequences disclosed herein, but which are degenerate to the nucleic acids disclosed herein. By "degenerate to" is meant that a different three-letter codon is used to specify a particular amino acid.

The term "polypeptide" refers to a polymer of amino acids and does not refer to a specific length of the product; thus, peptides, oligopeptides, and proteins are included within the definition of polypeptide. This term also does not refer to or exclude post-expression modifications of the polypeptide, for example, glycosylations, acetylations, phosphorylations and the like. Included within the definition are, for example, polypeptides containing one or more analogs of an amino acid (including, for example, unnatural amino acids, etc.), polypeptides with substituted linkages, as well as other modifications known in the art, both naturally occurring and non-naturally occurring.

A nucleic acid molecule is "operatively linked" to an expression control sequence wheh the expression control sequence controls and regulates the transcription and translation of nucleic acid sequence. The term "operatively linked" includes having an appropriate start signal (e.g., ATG) in front of the nucleic acid sequence to be expressed and maintaining the correct reading frame to permit expression of the nucleic acid sequence under the control of the expression control sequence and production of the desired product encoded by the nucleic acid sequence. If a gene that one desires to insert into a recombinant DNA molecule does not contain an appropriate start signal, such a start signal can be inserted in front of the gene.

The term "stringent hybridization conditions" are known to those skilled in the art and can be found in Current Protocols in Molecular Biology, John Wiley & Sons, N.Y. (1989), 6.3.1-6.3.6. A preferred, non-limiting example of stringent hybridization conditions is hybridization in 6× sodium chloride/sodium citrate (SSC) at about 45° C., followed by one or more washes in 0.2×SSC, 0.1% SDS at 50° C., preferably at 55° C., and more preferably at 60° C. or 65° C.

As used herein, "Arrays" or "Microarrays" refers to an array of distinct polynucleotides or oligonucleotides deposited on a substrate, such as paper, nylon or other type of membrane, filter, chip, glass slide, or any other suitable solid support. In one embodiment, the microarray is prepared and used according to the methods described in U.S. Pat. No. 5,837,832, PCT application WO95/11995, Lockhart et al. (1996; Nat. Biotech. 14: 1675-1680) and Schena et al. (1996; Proc. Natl. Acad. Sci. 93: 10614-10619). In other embodiments, such arrays are produced by the methods described by Brown et al., U.S. Pat. No. 5,807,522.

As defined herein, a "gene" is the segment of DNA involved in producing a polypeptide chain; it includes regions preceding and following the coding region, as well as intervening sequences (introns) between individual coding segments (exons).

As defined herein, "unique to" means a sequence that only occurs once in a genome.

DETAILED DESCRIPTION OF THE INVENTION

The invention is directed to isolated genomic polynucleotide fragments that encode human resistin and human syntaxin binding protein 2, which in a specific embodiment are the human resistin and human syntaxin binding protein 2 genes, as well as vectors and hosts containing these fragments and polynucleotide fragments hybridizing to noncoding regions, as well as antisense oligonucleotides to these fragments. The genomic polynucleotide fragments of the present invention may contain both sequences encoding resistin and syntaxin binding protein 2 and specifically may contain SEQ ID NO:3 and/or 4 or portions of SEQ ID NO:3 and/or 4.

The polynucleotides of the present invention may be in the form of RNA or in the form of DNA, which DNA includes genomic DNA and synthetic DNA. The DNA may be double-stranded or single-stranded and if single stranded may be the coding strand or non-coding strand. The genes encoding human resistin and human syntaxin binding protein 2 are disposed in the chromosome 19 genomic clones of accession numbers AC008763, gi 13699420, last contig (nucleotides 141174-194036), and AC021153, gi 8570240, reverse complement of contig 17 (nucleotide. 77433-94571). A composite of these two contigs, corrected for overlapping sequence, is prepared to yield a 64,700 base pair sequence. In the latter composite, the resistin gene is disposed in nucleotides 1-38587 (SEQ ID NO:3). The syntaxin binding protein 2 gene is disposed in the last 30943 nucleotides (SEQ ID NO:4).

The polynucleotides of the invention are naturally occurring polynucleotide sequences having at least a 95% identity and may have a 96%, 97%, 98%, 99%, 99.5% or 99.9% identity to the polynucleotides depicted in SEQ ID NOS:3, 4 or 5 as well as the polynucleotides in reverse sense orientation, or the polynucleotide sequences encoding the human resistin and human syntaxin binding protein 2 polypeptides depicted in SEQ ID NOS:1 or 2 respectively.

The comparison of sequences and determination of percent identity and similarity between two sequences can be accomplished using a mathematical algorithm. (Lesk, A. M., ed., 1988, Computational Molecular Biology, Oxford University Press, New York; Smith, D. W., ed., 1993, Biocomputing: Informatics and Genome Projects, Academic Press, New York; Griffin, A. M., and Griffin, H. G., eds, 1994, Computer Analysis of Sequence Data, Part 1, Humana Press, New Jersey; von Heinje, G., 1987, Sequence Analysis in Molecular Biology, Academic Press; and Gribskov, M. and Devereux, J., eds., 1991, Sequence Analysis Primer, M Stockton Press, New York). In a preferred embodiment, the percent identity between two amino acid sequences is determined using the Needleman and Wunsch (1970, J. Mol. Biol. 48: 444-453) algorithm which has been incorporated into the GAP program in the GCG software package (available at www.gcg.com), using either a Blossom 62 matrix or a PAM250 matrix, and a gap weight of 16, 14, 12, 10, 8, 6, or 4 and a length weight of 1, 2, 3, 4, 5, or 6. In yet another preferred embodiment, the percent identity between two nucleotide sequences is determined using the GAP program in the GCG software package (Devereux et al., 1984, Nucleic Acids Res. 12: 387) (available at http://www.gcg.com), using a NWSgapdna.CMP matrix and a gap weight of 40, 50, 60, 70, or 80 and a length weight of 1, 2, 3, 4, 5, or 6. In another embodiment, the percent identity between two amino acid or nucleotide sequences is determined using the algorithm of Myers and Miller (1989, CABIOS, 4: 11-17) which has been incorporated into the ALIGN program (version 2.0), using a PAM 120 weight residue table, a gap length penalty of 12 and a gap penalty of 4.

The nucleic acid sequences of the present invention can further be used as a "query sequence" to perform a search against sequence databases to, for example, identify other family members or related sequences. Such searches can be performed using the BLASTN and BLASTX programs (version 2.0) of Altschul, et al. (1990, J. Mol. Biol. 215: 403-410). BLAST nucleotide searches can be performed with the BLASTN program, score=100, wordlength=12 to obtain nucleotide sequences homologous to the nucleic acid molecules of the invention. BLASTN protein searches can be performed with the BLASTX program, score-50, wordlength=3 to obtain amino acid sequences homologous to the proteins of the invention. To obtain gapped alignments for comparison purposes, Gapped BLASTN can be utilized as described in Altschul et al. (1997, Nucleic Acids Res. 25: 3389-3402). When utilizing BLAST and gapped BLAST programs, the default parameters of the respective programs (e.g., BLASTX and BLASTN) can be used.

The invention also encompasses polynucleotides that hybridize to the polynucleotides depicted in SEQ ID NOS: 3, 4 and/or 5. This polynucleotide may have a maximum length of SEQ ID NOS: 3, 4 and/or 5. A polynucleotide "hybridizes" to another polynucleotide, when a single-stranded form of the polynucleotide can anneal to the other polynucleotide under the appropriate conditions of temperature and solution ionic strength (see Sambrook et al., supra). The conditions of temperature and ionic strength determine the "stringency" of the hybridization. For preliminary screening for homologous nucleic acids, low stringency hybridization conditions, corresponding to a temperature of 42° C., can be used, e.g., 5×SSC, 0.1% SDS, 0.25% milk, and no formamide; or 40% formamide, 5×SSC, 0.5% SDS). "Stringent hybridization conditions" can be found in Current Protocols in Molecular Biology, John Wiley & Sons, N.Y. (1989), 6.3.1-6.3.6. A preferred, non-limiting example of stringent hybridization conditions is hybridization in 6× sodium chloride/sodium citrate (SSC) at about 45° C., followed by one or more washes in 0.2×SSC, 0.1% SDS at 50° C., preferably at 55° C., and more preferably at 60° C. or 65° C.

Hybridization requires that the two nucleic acids contain complementary sequences, although depending on the stringency of the hybridization, mismatches between bases are possible. The appropriate stringency for hybridizing nucleic acids depends on the length of the nucleic acids and the degree of complementation, variables well known in the art. The greater the degree of similarity or complementarity between two nucleotide sequences, the greater the value of $T_m$ for hybrids of nucleic acids having those sequences. The relative stability (corresponding to higher $T_m$) of nucleic acid hybridizations decreases in the following order: RNA:RNA, DNA:RNA, DNA:DNA.

The invention is further directed to a nucleic acid construct comprising the nucleic acid molecules of the present invention. The nucleic acid sequence encoding the desired polypeptide, whether in fused or mature form, and whether or not containing a signal sequence to permit secretion, may be ligated into expression vectors suitable for any convenient host. The vector includes a plasmid, single or double stranded phage, a single or double stranded RNA or DNA viral vector, or artificial chromosome, such as a BAC, PAC, YAC, or MAC.

Polynucleotide and Polypeptide Variants

The invention is directed to both polynucleotide and polypeptide variants. A "variant" refers to a polynucleotide or polypeptide differing from the polynucleotide or polypeptide of the present invention, but retaining essential properties thereof. Generally, variants are overall closely similar and in many regions, identical to the polynucleotide or polypeptide of the present invention.

The variants may contain alterations in the coding regions, non-coding regions, or both. Especially preferred are polynucleotide variants containing alterations which produce silent substitutions, additions, or deletions, but do not alter the properties or activities of the encoded polypeptide. Nucleotide variants produced by silent substitutions due to the degeneracy of the genetic code are preferred. Moreover, variants in which 5-10, 1-5 or 1-2 amino acids are substituted, deleted, or added in any combination are also preferred.

The invention also encompasses allelic variants of said polynucleotides. An allelic variant denotes any of two or more alternative forms of a gene occupying the same chromosomal locus. Allelic variation arises naturally through mutation, and may result in polymorphism within populations and is thought to frequently occur. Gene mutations can be silent (no change in the encoded polypeptide) or may encode polypeptides having altered amino acid sequences. An allelic variant has a high homology to the original gene sequence. An allelic variant of a polypeptide is a polypeptide encoded by an allelic variant of a gene.

The amino acid sequences of the variant polypeptides may differ from the amino acid sequences depicted in SEQ ID NOS:1 or 2 by an insertion or deletion of one or more amino acid residues and/or the substitution of one or more amino acid residues by different amino acid residues. Preferably, amino acid changes are of a minor nature, that is conservative amino acid substitutions that do not significantly affect the folding and/or activity of the protein; small deletions, typically of one to about 30 amino acids; small amino- or carboxyl-terminal extensions, such as an amino-terminal methionine residue; a small linker peptide of up to about 20-25 residues; or a small extension that facilitates purification by changing net charge or another function, such as a poly-histidine tract, an antigenic epitope or a binding domain.

Examples of conservative substitutions are within the group of basic amino acids (arginine, lysine and histidine), acidic amino acids (glutamic acid and aspartic acid), polar amino acids (glutamine and asparagine), hydrophobic amino acids (leucine, isoleucine and valine), aromatic amino acids (phenylalanine, tryptophan and tyrosine), and small amino acids (glycine, alanine, serine, threonine and methionine). Amino acid substitutions which do not generally alter the specific activity are known in the art and are described, for example, by H. Neurath and R. L. Hill, 1979, In, The Proteins, Academic Press, New York. The most commonly occurring exchanges are Ala/Ser, Val/Ile, Asp/Glu, Thr/Ser, Ala/Gly, Ala/Thr, Ser/Asn, Ala/Val, Ser/Gly, Tyr/Phe, Ala/Pro, Lys/Arg, Asp/Asn, Leu/Ile, Leu/Val, as well as these in reverse.

Noncoding Regions

The invention is further directed to polynucleotide fragments containing or hybridizing to noncoding regions of the human resistin and human syntaxin binding protein 2 genes. These include but are not limited to an intron, a 5'-non-coding region, a 3'-non-coding region (see Tables 1-2), as well as transcription factor binding sites (see Table 3).

The invention is further directed to polynucleotide fragments or nucleic acid molecules containing or hybridizing to contiguous exon/intron and intron/exon sequences of human resistin or human syntaxin binding protein 2 genes. These sequences encompass each splice site, where the intron is removed, the exon-intron junction and additionally includes the consensus sequence spanning the exon and intron sequences immediately adjacent to the splice site: The fragments are at least 20 nucleotides in length and in one embodiment contain at least 10 nucleotides of intron sequences. Thus, the invention would encompass a nucleic acid molecule that contains or hybridizes to a polynucleotide fragment that combines contiguous coding and noncoding nucleic acid sequences of SEQ ID NO:3 or 4. Further, the polynucleotide fragments of the present invention may contain more than one exon-intron and/or intron-exon regions.

The polynucleotide fragment may be a short polynucleotide fragment which is between about 8 nucleotides to about 20 or 40 nucleotides in length. Such shorter fragments may be useful for diagnostic purposes. Such short polynucleotide fragments are also preferred with respect to polynucleotides or nucleic acid molecules containing or hybridizing to polynucleotides or nucleic acid molecules containing noncoding regions including but not limited to 5' and 3' noncoding region, intron regions, contiguous exon-intron and intron-exon regions. Alternatively larger fragments, e.g., of about 50, 60, 100, 150, 200, 300, 400, 500, 600, 750, 800, 900, 1000, 1,500, 2000, 3000, 4000, 5000 or about 10000 nucleotides in length may be used.

TABLE 1

Exon/Intron Organization of the Resistin Gene in Genomic SEQ ID NO:3 (Reverse Strand Coding).

| EXON | Nucleotide No. | Amino Acid No. |
|---|---|---|
| Stop Codon | 19611-19613 | |
| 3 | 19614-19742 | 108-66 |
| 2 | 20063-20140 | 65-40 |
| 1 | 20517-20633 | 39-1 |

TABLE 2

Exon/Intron Organization of the Syntax in Binding Protein 2 Gene in Genomic SEQ ID NO:4 (Reverse Strand Coding).

| Exon | Nucleotide No. | Amino Acid No. |
|---|---|---|
| Stop Codon | 8391-8393 | |
| 19 | 8394-8477 | 593-566 |
| 18 | 8691-8849 | 565-513 |
| 17 | 8956-9039 | 512-485 |
| 16 | 9857-9952 | 484-453 |
| 15 | 10895-11005 | 452-416 |
| 14 | 11450-11590 | 415-369 |
| 13 | 12959-13036 | 368-343 |
| 12 | 13153-13221 | 342-320 |
| 11 | 13378-13434 | 319-301 |
| 10 | 13667-13774 | 300-265 |
| 9 | 13870-13998 | 264-222 |
| 8 | 14083-14166 | 221-194 |
| 7 | 14347-14502 | 193-142 |
| 6 | 15204-15302 | 141-109 |
| 5 | 15393-15470 | 108-83 |
| 4 | 16394-16471 | 82-57 |
| 3 | 17102-17182 | 56-30 |
| 2 | 17426-17476 | 29-13 |
| 1 | 19016-19051 | 12-1 |

TABLE 3

NUMBERS OF TRANSCRIPTION FACTOR BINDING SITES ON GENES THAT ENCODE RESISTIN AND SYNTAXIN BINDING PROTEIN 2 (STXBP2).

| BINDING SITES | RESISTIN | STXBP2 |
|---|---|---|
| AP1_C | 6 | 2 |
| AP4_Q5 | 3 | 4 |
| AP4_Q6 | 3 | 4 |
| CAAT_01 | 7 | 4 |
| CREBP1CJUN_01 | 3 | |
| CREB_01 | 2 | |
| DELTAEF1_01 | 12 | 7 |
| GATA_C | | 2 |
| GC_01 | | 2 |
| GKLF_01 | 2 | 2 |
| HFH3_01 | 2 | |
| IK2_01 | 3 | |
| LMO2COM_01 | 5 | 7 |
| LMO2COM_02 | 3 | 4 |
| LYF1_01 | 36 | 14 |
| MYOD_Q6 | 17 | 11 |
| MZF1_01 | 51 | 50 |
| NFAT_Q6 | 3 | |
| NKX25_01 | 30 | 14 |
| NMYC_01 | | 3 |
| PADS_C | 2 | |

TABLE 3-continued

NUMBERS OF TRANSCRIPTION FACTOR BINDING SITES ON GENES THAT ENCODE RESISTIN AND SYNTAXIN BINDING PROTEIN 2 (STXBP2).

| BINDING SITES | RESISTIN | STXBP2 |
|---|---|---|
| S8_01 | | 2 |
| SOX5_01 | 5 | 6 |
| SP1_Q6 | | 3 |
| SREBP1_01 | 2 | |
| TCF11_01 | 17 | 7 |
| USF_01 | 14 | 14 |
| USF_C | 18 | 14 |

In a specific embodiment, such noncoding sequences are expression control sequences. In a more specific embodiment of the invention, the expression control sequences may be operatively linked to a polynucleotide encoding a heterologous polypeptide. Such expression control sequences may be about 50-200 nucleotides in length and specifically about 50, 100, 200, 500, 600, 1000 or 2000 nucleotides in length. The invention is further directed to antisense oligonucleotides and mimetics to these polynucleotide sequences. Antisense technology can be used to control gene expression through triple-helix formation or antisense DNA or RNA, both of which methods are based on binding of a polynucleotide to DNA or RNA. For example, the 5' coding portion of the polynucleotide sequence, which encodes the mature polypeptides of the present invention, is used to design an antisense RNA oligonucleotide of from about 10 to 40 base pairs in length. A DNA oligonucleotide is designed to be complementary to a region of the gene involved in transcription or RNA processing (triple helix (see Lee et al., Nucl. Acids Res., 6: 3073 (1979); Cooney et al, Science, 241: 456 (1988); and Dervan et al., Science, 251: 1360 (1991)), thereby preventing transcription and the production of said polypeptides.

Expression of Polypeptides

Isolated Polynucleotide Sequences

The human chromosome 19 genomic clones of accession numbers AC008763, gi 13699420, last contig (nucleotides 141174-194036) and AC021153, gi 8570249, reverse complement of contig 17 (nucleotides 77433-94571) have been discovered to contain the human resistin and human syntaxin binding protein 2 genes by Genscan analysis (Burge et al., 1997, J. Mol. Biol. 268: 78-94), BLAST2 and TBLASTN analysis (Altschul et al., 1997, Nucl. Acids Res. 25: 3389-3402). The sequences of AC008763, gi 13699420, and AC021153, gi 8570249 are compared to the human resistin and syntaxin cDNA sequences, accession numbers AF352730 (resistin) and AF205952. It has been found that resistin is disposed immediately adjacent to the syntaxin binding protein 2 gene. A composite of these two contigs, corrected for overlapping sequence, is prepared to yield a 64,700 base pair sequence (SEQ ID NO:5). In the latter composite, the resistin gene is disposed in nucleotides 1-38587 (SEQ ID NO:3). The syntaxin binding protein 2 gene is disposed in the last 30943 nucleotides (SEQ ID NO:4).

The cloning of the nucleic acid sequences of the present invention from such genomic DNA can be effected, e.g., by using the well known polymerase chain reaction (PCR) or antibody screening of expression libraries to detect cloned DNA fragments with shared structural features. See, e.g., Innis et al., 1990, *PCR: A Guide to Methods and Application*, Academic Press, New York. Other nucleic acid amplification procedures such as ligase chain reaction (LCR), ligated activated transcription (LAT) and nucleic acid sequence-based amplification (NASBA) or long range PCR may be used. In a specific embodiment, 5'- or 3'-non-coding portions of the gene may be identified by methods including but are not limited to, filter probing, clone enrichment using specific probes and protocols similar or identical to 5'- and 3'-"RACE" protocols which are well known in the art. For instance, a method similar to 5'-RACE is available for generating the missing 5'-end of a desired full-length transcript. (Fromont-Racine et al., 1993, Nucl. Acids Res. 21: 1683-1684).

Once the DNA fragments are generated, identification of the specific DNA fragment containing the desired human resistin and/or syntaxin gene may be accomplished in a number of ways. For example, if an amount of a portion of a human resistin or syntaxin gene or its specific RNA, or a fragment thereof, is available and can be purified and labeled, the generated DNA fragments may be screened by nucleic acid hybridization to the labeled probe (Benton and Davis, 1977, Science 196: 180; Grunstein and Hogness, 1975, Proc. Natl. Acad. Sci. U.S.A. 72: 3961). The present invention provides such nucleic acid probes, which can be conveniently prepared from the specific sequences disclosed herein, e.g., a hybridizable probe having a nucleotide sequence corresponding to at least a 10, and preferably a 15, nucleotide fragment of the sequences depicted in SEQ ID NO:2. Preferably, a fragment is selected that is unique to the polypeptides of the invention. Methods are commonly known in the art for preparing such unique sequences and are reviewed in Stoughton, 2005, Annu. Rev. Biochem. 74: 53-82. Those DNA fragments with substantial homology to the probe will hybridize. As noted above, the greater the degree of homology, the more stringent hybridization conditions can be used. In one embodiment, low stringency hybridization conditions are used to identify a homologous human resistin or syntaxin polynucleotide. However, in a preferred aspect, and as demonstrated experimentally herein, a nucleic acid encoding a polypeptide of the invention will hybridize to a nucleic acid derived from the polynucleotide sequence depicted in SEQ ID NO:2 or a hybridizable fragment thereof, under moderately stringent conditions; more preferably, it will hybridize under high stringency conditions.

Alternatively, the presence of the gene may be detected by assays based on the physical, chemical, or immunological properties of its expressed product. For example, cDNA clones, or DNA clones which hybrid-select the proper mRNAs, can be selected which produce a protein that, e.g., has similar or identical electrophoretic migration, isoelectric focusing behavior, proteolytic digestion maps, or antigenic properties as known for the human resistin or syntaxin polynucleotide.

A gene encoding human resistin or syntaxin polypeptide can also be identified by mRNA selection, i.e., by nucleic acid hybridization followed by in vitro translation. In this procedure, fragments are used to isolate complementary mRNAs by hybridization. Immunoprecipitation analysis or functional assays of the in vitro translation products of the products of the isolated mRNAs identifies the mRNA and, therefore, the complementary DNA fragments, that contain the desired sequences.

Nucleic Acid Constructs

The present invention also relates to nucleic acid constructs comprising a polynucleotide sequence containing the exon/intron segments of the human resistin and/or syntaxin gene operably linked to one or more control sequences which direct the expression of the coding sequence in a suitable host cell under conditions compatible with the control sequences. Expression will be understood to include any step involved in the production of the polypeptide including, but not limited to, transcription, post-transcriptional modification, translation, post-translational modification, and secretion.

"Nucleic acid construct" is defined herein as a nucleic acid molecule, either single- or double-stranded, which is isolated from a naturally occurring gene or which has been modified to contain segments of nucleic acid which are combined and juxtaposed in a manner which would not otherwise exist in nature. The term nucleic acid construct is synonymous with the term expression cassette when the nucleic acid construct contains all the control sequences required for expression of a coding sequence of the present invention. The term "coding sequence" is defined herein as a portion of a nucleic acid sequence which directly specifies the amino acid sequence of its protein product. The boundaries of the coding sequence are generally determined by a ribosome binding site (prokaryotes) or by the ATG start codon (eukaryotes) and a transcription terminator sequence located just downstream of the open reading frame at the 3'-end of the mRNA. A coding sequence can include, but is not limited to, DNA, cDNA, and recombinant nucleic acid sequences.

The isolated polynucleotide of the present invention may be manipulated in a variety of ways to provide for expression of the polypeptide. Manipulation of the nucleic acid sequence prior to its insertion into a vector may be desirable or necessary depending on the expression vector. The techniques for modifying nucleic acid sequences utilizing recombinant DNA methods are well known in the art.

The control sequence may be an appropriate promoter sequence, a nucleic acid sequence which is recognized by a host cell for expression of the nucleic acid sequence. The promoter sequence contains transcriptional control sequences that regulate the expression of the polynucleotide. The promoter may be any nucleic acid sequence that shows transcriptional activity in the host cell of choice including mutant, truncated, and hybrid promoters, and may be obtained from genes encoding extracellular or intracellular polypeptides either homologous or heterologous to the host cell.

The control sequence may also be a suitable transcription terminator sequence, a sequence recognized by a host cell to terminate transcription. The terminator sequence is operably linked to the 3'-terminus of the nucleic acid sequence encoding the polypeptide. Any terminator which is functional in the host cell of choice may be used in the present invention.

The control sequence may also be a suitable leader sequence, a nontranslated region of an mRNA which is important for translation by the host cell. The leader sequence is operably linked to the 5'-terminus of the nucleic acid sequence encoding the polypeptide. Any leader sequence that is functional in the host cell of choice may be used in the present invention.

The control sequence may also be a polyadenylation sequence, a sequence which is operably linked to the 3'-terminus of the nucleic acid sequence and which, when transcribed, is recognized by the host cell as a signal to add polyadenosine residues to transcribed mRNA. Any polyadenylation sequence which is functional in the host cell of choice may be used in the present invention.

The control sequence may also be a signal peptide coding region, which codes for an amino acid sequence linked to the amino terminus of the polypeptide which can direct the encoded polypeptide into the cell's secretory pathway. The 5'-end of the coding sequence of the nucleic acid sequence may inherently contain a signal peptide-coding region naturally linked in translation reading frame with the segment of the coding region which encodes the secreted polypeptide. Alternatively, the 5'-end of the coding sequence may contain a signal peptide coding region which is foreign to the coding sequence. The foreign signal peptide-coding region may be required where the coding sequence does not normally contain a signal peptide-coding region. Alternatively, the foreign signal peptide-coding region may simply replace the natural signal peptide-coding region in order to obtain enhanced secretion of the polypeptide. However, any signal peptide-coding region which directs the expressed polypeptide into the secretory pathway of a host cell of choice may be used in the present invention.

The control sequence may also be a propeptide coding region, which codes for an amino acid sequence positioned at the amino terminus of a polypeptide. The resultant polypeptide is known as a proenzyme or propolypeptide (or a zymogen in some cases). A propolypeptide is generally inactive and can be converted to a mature active polypeptide by catalytic or autocatalytic cleavage of the propeptide from the propolypeptide. The propeptide coding region may be obtained from the *Bacillus subtilis* alkaline protease gene (aprE), the *Bacillus subtilis* neutral protease gene (npr7), the *Saccharomyces cerevisiae* alpha-factor gene, the *Rhizomucor miehei* aspartic proteinase gene, or the *Myceliophthora thermophila* laccase gene (WO 95/33836).

Where both signal peptide and propeptide regions are present at the amino terminus of a polypeptide, the propeptide region is positioned next to the amino terminus of a polypeptide and the signal peptide region is positioned next to the amino terminus of the propeptide region.

It may also be desirable to add regulatory sequences which allow the regulation of the expression of the polypeptide relative to the growth of the host cell. Examples of regulatory systems are those which cause the expression of the gene to be turned on or off in response to a chemical or physical stimulus, including the presence of a regulatory compound. Regulatory systems in prokaryotic systems would include the lac, tac, and trp operator systems. In yeast, the ADH2 system or GAL1 system may be used. In filamentous fungi, the TAKA alpha-amylase promoter, *Aspergillus niger* glucoamylase promoter, and the *Aspergillus oryzae* glucoamylase promoter may be used as regulatory sequences. Other examples of regulatory sequences are those which allow for gene amplification. In eukaryotic systems, these include the dihydrofolate reductase gene which is amplified in the presence of methotrexate, and the metallothionein genes which are amplified with heavy metals. In these cases, the nucleic acid sequence encoding the polypeptide would be operably linked with the regulatory sequence.

Expression Vectors

Both eukaryotic and prokaryotic host systems are presently used in forming recombinant polypeptides. The polypeptide is then isolated from lysed cells or from the culture medium and purified to the extent needed for its intended use. Purification may be by techniques known in the art, for example, differential extraction, salt fractionation, chromatography on ion exchange resins, affinity chromatography, centrifugation, and the like. See, for example, Methods in Enzymology for a variety of methods for purifying proteins. Both prokaryotic and eukaryotic host cells may be used for expression of desired coding sequences when appropriate control sequences, which are compatible with the designated host, are used. Bacterial cells include, but are not limited to, *E. coli, Streptomyces,* and *Salmonella typhimurium.* Expression control sequences for prokaryotes include promoters, optionally containing operator portions, and ribosome binding sites. Transfer vectors compatible with prokaryotic hosts are commonly derived from, for example, pBR322, a plasmid containing operons conferring ampicillin and tetracycline resistance, and the various pUC vectors, which also contain sequences conferring antibiotic resistance markers. These markers may be used to obtain successful transformants by selection. Commonly used prokaryotic control sequences include the Beta-lactamase (penicillinase) and lactose promoter systems, the tryptophan (trp) promoter system and the lambda-derived $P_L$ promoter and N gene ribosome binding site and the hybrid TAC promoter derived from sequences of the trp and lac UV5 promoters. The foregoing systems are particularly compatible with *E. coli*; if desired, other prokaryotic hosts such as strains of *Bacillus* or *Pseudomonas* may be used, with corresponding control sequences.

Eukaryotic cells include, but are not limited to, yeast, insect cells such as *Drosophila*, animal cells such as COS and CHO cells, and plant cells. *Saccharomyces cerevisiae* and *Saccharomyces carlsbergensis* are the most commonly used yeast hosts, and are convenient fungal hosts. Yeast compatible vectors carry markers that permit selection of successful transformants by conferring prototrophy to auxotrophic mutants or resistance to heavy metals on wild-type strains. Yeast compatible vectors may employ the 2 micron origin of replication, the combination of CEN3 and ARS1 or other means for assuring replication, such as sequences which will result in incorporation of an appropriate fragment into the host cell genome. Examples of vectors for expression in yeast e.g., *S. cerevisiae* include pYepSec1 (Baldari, et al., 1987, EMBO J. 6: 229-234; pMFa (Kuijan et al., 1982, Cell 30: 933-943), pJRY88 (Schultz et al., 1987, Gene 54: 113-123), and pYES2 (Invitrogen Corporation, San Diego, Calif.). The nucleic acid molecules can also be expressed in insect cells using, for example, baculovirus expression vectors. Baculovirus vectors available for expression of proteins in cultured insect cells (e.g., Sf 9 cells) include the pAc series (Smith et al., 1983, Mol. Cell. Biol. 3: 2156-2165) and the pVL series (Lucklow et al., 1989, Virology 170: 31-39).

Mammalian cell lines available as hosts for expression are known in the art and include many immortalized cell lines available from the American Type Culture Collection (ATCC), including HeLa cells, Chinese hamster ovary (CHO) cells, baby hamster kidney (BHK) cells, and a number of other cell lines. Suitable promoters for mammalian cells are also known in the art and include viral promoters such as that from Simian Virus 40 (SV40), Rous sarcoma virus (RSV), adenovirus (ADV), and bovine papilloma virus (BPV). Mammalian cells may also require terminator sequences and poly A addition sequences; enhancer sequences which increase expression may also be included, and sequences which cause amplification of the gene may also be desirable. These sequences are known in the art.

It will be understood that not all vectors, expression control sequences and hosts will function equally well to express the polynucleotide sequences of this invention. Neither will all hosts function equally well with the same expression system. However, one skilled in the art will be able to select the proper vectors, expression control sequences, and hosts without undue experimentation to accomplish the desired expression without departing from the scope of this invention. For example, in selecting a vector, the host must be considered because the vector must function in it. The vector's copy number, the ability to control that copy number, and the expression of any other proteins encoded by the vector, such as antibiotic markers, will also be considered.

In selecting an expression control sequence, a variety of factors will normally be considered. These include, for example, the relative strength of the system, its controllability, and its compatibility with the particular DNA sequence or gene to be expressed, particularly as regards potential secondary structures. Suitable unicellular hosts will be selected by consideration of, e.g., their compatibility with the chosen vector, their secretion characteristics, their ability to fold proteins correctly, and their fermentation requirements, as well as the toxicity to the host of the product encoded by the DNA sequences to be expressed, and the ease of purification of the expression products.

Considering these and other factors a person skilled in the art will be able to construct a variety of vector/expression control sequence/host combinations that will express the nucleic acid molecules of this invention on fermentation or in large scale animal culture.

The polypeptides may be detected using methods known in the art that are specific for the polypeptides. These detection methods may include use of specific antibodies, formation of an enzyme product, or disappearance of an enzyme substrate. An enzyme assay may be used to determine the activity of the polypeptide. Resistin can be determined using the immunoassay procedure described by Steppan et al., Nature 409: 307-12, 2001. The human syntaxin binding protein 2 may be detected by its ability to bind to syntaxins 1A, 2 and 3 but not to syntaxin 4 (Katagiri et al., J. Biol. Chem. 270: 4963-6, 1995).

Antibodies

According to the invention, the human resistin or human syntaxin binding protein 2 polypeptides produced according to the method of the present invention may be used as an immunogen to generate any of these antibodies. Such antibodies include but are not limited to polyclonal, monoclonal, chimeric, single chain, Fab fragments, and a Fab expression library.

Various hosts may be used and include but are not limited to goats, rabbits, rats, mice, humans, and others. These hosts may be immunized by injection with the polypeptides of the present invention or any fragment or oligopeptide thereof which has immunogenic properties (e.g., 5-10 peptide fragments with immunogenic properties). Various adjuvants may be used to increase immunological response. Such adjuvants include, but are not limited to, Freund's, mineral gels such as aluminum hydroxide, and surface active substances such as lysolecithin, pluronic polyols, polyanions, peptides, oil emulsions, keyhole limpet hemocyanin, and dinitrophenol. BCG (bacilli Calmette-Guerin) and *Corynebacterium parvum* are especially preferable in humans.

Monoclonal antibodies to the said polypeptides and peptides of the present invention may be prepared using any technique which provides for the production of antibody molecules by continuous cell lines in culture. These include, but are not limited to, the hybridoma technique, the human B-cell hybridoma technique, and the EBV-hybridoma technique. See, e.g., Kohler, et al., 1975, Nature, 256: 495-497; Kozbor et al., 1985, J. Immunol. Methods 81: 31-42; Cote et al., 1983, Proc. Natl. Acad. Sci. USA 80: 2026-2030; Cole et al., 1984, Mol. Cell. Biol. 62: 109-120.

Various immunoassays may be used for screening to identify antibodies having the desired specificity. Numerous protocols for competitive binding or immunoradiometric assays using either polyclonal or monoclonal antibodies with established specificities are well known in the art. Such immunoassays typically involve the measurement of complex formation between the polypeptide(s) of the present invention and its specific antibody.

Antibodies may be conjugated to a solid support suitable for a diagnostic assay (e.g., beads, plates, slides or wells formed from materials such as latex or polystyrene) in accordance with known techniques, such as precipitation. Antibodies may likewise be conjugated to detectable groups such as radiolabels (e.g. $^{35}$S, $^{125}$I, $^{131}$I), enzyme labels (e.g., horseradish peroxidase, alkaline phosphatase), and fluorescent labels (e.g., fluorescein) in accordance with known techniques.

Microarrays and Kits

The microarray generally contains a large number of single-stranded nucleic acid sequences, fixed to a solid support, wherein at least one of which is a nucleic acid hybridizing to at least one 20 (and/or larger) nucleotide fragment unique to a (forward or reverse strand) noncoding region of SEQ ID NO:3 or 4. The fragment may hybridize to the coding and noncoding region. Alternatively larger fragments, e.g., of about 50, 70, 75, 150, 500, 600, 750, 800, 850, 900 or about 950 nucleotides in length may be used. In yet another embodiment, BAC or YAC arrays may be used containing full length cDNA or genomic sequences. The kit may also comprise coding sequences of SEQ ID NO: 3 or 4.

In order to produce oligonucleotides to a known sequence for a microarray or detection kit, the nucleic acid of interest is typically examined using a computer algorithm which starts at the 5' or at the 3' end of the nucleotide sequence. Typical algorithms will then identify oligomers of defined length that are unique to said nucleic acid, have a GC content within a range suitable for hybridization, and lack predicted secondary structure that may interfere with hybridization. In certain situations it may be appropriate to use pairs of oligonucleotides on a microarray or detection kit. The "pairs" will be identical, except for one nucleotide that preferably is located in the center of the sequence. The second oligonucleotide in the pair (mismatched by one) serves as a control. The number of oligonucleotide pairs may range from two to one million. The oligomers may be synthesized at designated areas on a solid support using a light-directed chemical process or prepared elsewhere and then deposited on the solid support. The solid support may be paper, nylon or other type of membrane, filter, chip, glass slide or any other suitable solid support.

The microarrays of the present invention may be used to identify nucleic acids encoding resistin and/or syntaxin.

In another embodiment, the invention is directed to a kit comprising at least one nucleic acid comprising at least 20 nucleotides hybridizing under stringent conditions to a noncoding region of the nucleic acid of the present invention. The kit may also comprise a polynucleotide fragment encompassing the coding region of resistin or syntaxin. In a more specific embodiment, the kit comprises a probe or primer comprising 50, 70, 75, 150, 500, 600, 750, 800, 850, 900 or about 950 nucleotides in length may be used. In yet another embodiment, BAC, PAC or YAC arrays may be used containing full length genomic sequences. The nucleic acid may act as a probe or primer and may be labeled with a detectable label. The detectable label may, for example, be a radioactive label, fluorescer, antibody or enzyme. The kit may further comprise the label. Alternatively, the kit may comprise a microarray. The probes or primers of the present invention may act as a primer to synthesize further nucleic acid probes.

Conditions for incubating a nucleic acid molecule with a test sample vary. Incubation conditions depend on the format employed in the assay, the detection methods employed, and the type and nature of the nucleic acid molecule used in the assay. One skilled in the art will recognize that any one of the commonly available hybridization, amplification or array assay formats can readily be adapted to employ the novel fragments disclosed herein. Examples of such assays can be found in Chard, 1986, An Introduction to Radioimmunoassay and Related Techniques, Elsevier Science Publishers, Amsterdam, The Netherlands; Bullock, G. R. et al., Techniques in Immunocytochemistry, Academic Press, Orlando, Fla. Vol. 1 (1982), Vol. 2 (1983), Vol. 3 (1985); Tinsel, Practice and Theory of Enzyme Immunoassays: Laboratory Techniques in Biochemistry and Molecular Biology, Elsevier Science Publishers, Amsterdam, The Netherlands (1985).

Therapeutic Uses

Antisense Oligonucleotides and Mimetics

The invention is further directed to antisense oligonucleotides and mimetics to these polynucleotide sequences. Antisense technology can be used to control gene expression through triple-helix formation or antisense DNA or RNA, both of which methods are based on binding of a polynucleotide to DNA or RNA. For example, the 5' coding portion of the polynucleotide sequence, which encodes the mature polypeptides of the present invention, is used to design an antisense RNA oligonucleotide of from about 10 to 40 base pairs in length. A DNA oligonucleotide is designed to be complementary to a region of the gene involved in transcription or RNA processing (triple helix (see Lee et al., Nucl. Acids Res., 6: 3073 (1979); Cooney et al, Science, 241: 456 (1988); and Dervan et al., Science, 251: 1360 (1991)), thereby preventing transcription and the production of said polypeptides. As defined herein, a "mimetic" is an oligonucleotide having non-naturally occurring portions which function similarly to naturally occurring oligonucleotides and may include peptide-nucleic acids (PNAs). Modifications may occur at the phosphate linkage (e.g., methylphosphonates, phosphothioates) or sugar linkage, cyclobutyl moieties in place of the pentofuranosyl sugar or at the purine or pyrimidine bases themselves as described in US 2004/0214325.

The antisense oligonucleotides or mimetics of the present invention may be used to decrease levels of a polypeptide. For example, human resistin inhibits actions of insulin. Therefore, the human resistin antisense oligonucleotides of the present invention could be used to treat insulin-resistant forms of type 2 diabetes. Human syntaxin binding protein 2 plays a role in vesicle trafficking, thus its antisense sequences may be used to treat endocrine tumors such as insulinomas from which hormones such as insulin are secreted in health-threatening excess.

The antisense oligonucleotides of the present invention may be formulated into pharmaceutical compositions. These compositions may be administered in a number of ways depending upon whether local or systemic treatment is desired and upon the area to be treated. Administration may be topical (including ophthalmic and to mucous membranes including vaginal and rectal delivery), pulmonary, e.g., by inhalation or insufflation of powders or aerosols, including by nebulizer; intratracheal, intranasal, epidermal and transdermal), oral or parenteral. Parenteral administration includes intravenous, intraarterial, subcutaneous, intraperitoneal or intramuscular injection or infusion; or intracranial, e.g., intrathecal or intraventricular, administration.

Pharmaceutical compositions and formulations for topical administration may include transdermal patches, ointments, lotions, creams, gels, drops, suppositories, sprays, liquids and powders. Conventional pharmaceutical carriers, aqueous, powder or oily bases, thickeners and the like may be necessary or desirable.

Compositions and formulations for oral administration include powders or granules, suspensions or solutions in water or non-aqueous media, capsules, sachets or tablets. Thickeners, flavoring agents, diluents, emulsifiers, dispersing aids or binders may be desirable.

Compositions and formulations for parenteral, intrathecal or intraventricular administration may include sterile aqueous solutions that may also contain buffers, diluents and other suitable additives such as, but not limited to, penetration enhancers, carrier compounds and other pharmaceutically acceptable carriers or excipients.

Pharmaceutical compositions of the present invention include, but are not limited to, solutions, emulsions, and liposome-containing formulations. These compositions may be generated from a variety of components that include, but are not limited to, preformed liquids, self-emulsifying solids and self-emulsifying semisolids.

The pharmaceutical formulations of the present invention, which may conveniently be presented in unit dosage form, may be prepared according to conventional techniques well known in the pharmaceutical industry. Such techniques include the step of bringing into association the active ingredients with the pharmaceutical carrier(s) or excipient(s). In general, the formulations are prepared by uniformly and intimately bringing into association the active ingredients with liquid carriers or finely divided solid carriers or both, and then, if necessary, shaping the product.

The compositions of the present invention may be formulated into any of many possible dosage forms such as, but not limited to, tablets, capsules, liquid syrups, soft gels, suppositories, and enemas. The compositions of the present invention may also be formulated as suspensions in aqueous, non-aqueous or mixed media. Aqueous suspensions may further contain substances that increase the viscosity of the suspension including, for example, sodium carboxymethylcellulose, sorbitol and/or dextran. The suspension may also contain stabilizers.

In one embodiment of the present invention, the pharmaceutical compositions may be formulated and used as foams. Pharmaceutical foams include formulations such as, but not limited to, emulsions, microemulsions, creams, jellies and liposomes. While basically similar in nature these formulations vary in the components and the consistency of the final product. The preparation of such compositions and formulations is generally known to those skilled in the pharmaceutical and formulation arts and may be applied to the formulation of the compositions of the present invention.

The formulation of therapeutic compositions and their subsequent administration is believed to be within the skill of those in the art. Dosing is dependent on severity and responsiveness of the disease state to be treated, with the course of treatment lasting from several days to several months, or until a cure is effected or a diminution of the disease state is achieved. Optimal dosing schedules can be calculated from measurements of drug accumulation in the body of the patient. Persons of ordinary skill can easily determine optimum dosages, dosing methodologies and repetition rates. Optimum dosages may vary depending on the relative potency of individual oligonucleotides, and can generally be estimated based on $EC_{50}$ as found to be effective in in vitro and in vivo animal models.

In general, dosage is from 0.01 ug to 10 g per kg of body weight, and may be given once or more daily, weekly, monthly or yearly, or even once every 2 to 20 years. Persons of ordinary skill in the art can easily estimate repetition rates for dosing based on measured residence times and concentrations of the drug in bodily fluids or tissues. Following successful treatment, it may be desirable to have the patient undergo maintenance therapy to prevent the recurrence of the disease state, wherein the oligonucleotide is administered in maintenance doses, ranging from 0.01 ug to 10 g per kg of body weight, once or more daily, to once every 20 years.

Gene Therapy

As noted above, human resistin inhibits actions of insulin, and human syntaxin binding protein 2 plays a role in secretory vesicle trafficking. Therefore, the human resistin gene may be used to modulate conditions in which insulin is secreted in excess, as in functional insulinomas. The human syntaxin binding protein 2 gene may be used to stimulate secretory vesicle release from hypofunctional endocrine tissues such as the pancreas islet cells in juvenile diabetes.

As described herein, the polynucleotide of the present invention may be introduced into a patient's cells for therapeutic uses. As will be discussed in further detail below, cells can be transfected using any appropriate means, including viral vectors, as shown by the example, chemical transfectants, or physico-mechanical methods such as electroporation and direct diffusion of DNA. See, for example, Wolff, Jon A, et al., "Direct gene transfer into mouse muscle in vivo," Science, 247, 1465-1468, 1990; and Wolff, Jon A, "Human dystrophin expression in mdx mice after intramuscular injection of DNA constructs," Nature, 352, 815-818, 1991. As used herein, vectors are agents that transport the gene into the cell without degradation and include a promoter yielding expression of the gene in the cells into which it is delivered. As will be (1) (2) discussed in further detail below, promoters can be general promoters, yielding expression in a variety of mammalian cells, or cell specific, or even nuclear versus cytoplasmic specific. These are known to those skilled in the art and can be constructed using standard molecular biology protocols. Vectors have been divided into two classes: a) Biological agents derived from viral, bacterial or other sources; b) Chemical physical methods that increase the potential for gene uptake, directly introduce the gene into the nucleus or target the gene to a cell receptor.

Biological Vectors

Viral vectors have higher transaction (ability to introduce genes) abilities than do most chemical or physical methods to introduce genes into cells. Vectors that may be used in the present invention include viruses, such as adenoviruses, adeno associated virus (AAV), vaccinia, herpesviruses, baculoviruses and retroviruses, bacteriophages, cosmids, plasmids, fungal vectors and other recombination vehicles typically used in the art which have been described for expression in a variety of eukaryotic and prokaryotic hosts, and may be used for gene therapy as well as for simple protein expression. Polynucleotides are inserted into vector genomes using methods well known in the art.

Retroviral vectors are the vectors most commonly used in clinical trials, since they carry a larger genetic payload than other viral vectors. However, they are not useful in non-proliferating cells. Adenovirus vectors are relatively stable and easy to work with, have high titers, and can be delivered in aerosol formulation. Pox viral vectors are large and have several sites for inserting genes, they are thermostable and can be stored at room temperature.

Examples of promoters are SP6, T4, T7, SV40 early promoter, cytomegalovirus (CMV) promoter, mouse mammary tumor virus (MMTV) steroid-inducible promoter, Moloney murine leukemia virus (MMLV) promoter, phosphoglycerate kinase (PGK) promoter, and the like. Alternatively, the promoter may be an endogenous adenovirus promoter, for example the E1a promoter or the Ad2 major late promoter (MLP). Similarly, those of ordinary skill in the art can construct adenoviral vectors utilizing endogenous or heterologous poly A addition signals.

Plasmids are not integrated into the genome and the vast majority of them are present only from a few weeks to several months, so they are typically very safe. However, they have lower expression levels than retroviruses and since cells have the ability to identify and eventually shut down foreign gene expression, the continuous release of DNA from the polymer to the target cells substantially increases the duration of functional expression while maintaining the benefit of the safety associated with non-viral transfections.

Chemical/Physical Vectors

Other methods to directly introduce genes into cells or exploit receptors on the surface of cells include the use of liposomes and lipids, ligands for specific cell surface receptors, cell receptors, and calcium phosphate and other chemical mediators, microinjections directly to single cells, electroporation and homologous recombination. Liposomes are commercially available from Gibco BRL, for example, as LIPOFECTIN and LIPOFECTACE, which are formed of cationic lipids such as N-[1-(2,3 dioleyloxy)-propyl]-n,n,n-trimethylammonium chloride (DOTMA) and dimethyl dioctadecylammonium bromide (DDAB). Numerous methods are also published for making liposomes, known to those skilled in the art.

For example, Nucleic acid-Lipid Complexes—Lipid carriers can be associated with naked nucleic acids (e.g., plasmid DNA) to facilitate passage through cellular membranes. Cationic, anionic, or neutral lipids can be used for this purpose. However, cationic lipids are preferred because they have been shown to associate better with DNA that, generally, has a negative charge. Cationic lipids have also been shown to mediate intracellular delivery of plasmid DNA (Feigner and Ringold, Nature 337: 387 (1989)). Intravenous injection of cationic lipid-plasmid complexes into mice has been shown to result in expression of the DNA in lung (Brigham et al., Am. J. Med. Sci. 298: 278 (1989)). See also, Osaka et al., J. Pharm. Sci. 85(6): 612-618 (1996); San et al., Human Gene Therapy 4: 781-788 (1993); Senior et al., Biochemica et Biophysica Acta 1070: 173-179 (1991); Kabanov and Kabanov, Bioconjugate Chem. 6: 7-20 (1995); Remy et al., Bioconjugate Chem. 5: 647-654 (1994); Behr, J-P., Bioconjugate Chem 5: 382-389 (1994); Behr et al., Proc. Natl. Acad. Sci., USA 86: 6982-6986 (1989); and Wyman et al., Biochem. 36: 3008-3017 (1997).

Cationic lipids are known to those of ordinary skill in the art. Representative cationic lipids include those disclosed, for example, in U.S. Pat. No. 5,283,185; and e.g., U.S. Pat. No. 5,767,099. In a preferred embodiment, the cationic lipid is N.sup.4-spermine cholesteryl carbamate (GL-67) disclosed in U.S. Pat. No. 5,767,099. Additional preferred lipids include N4-spermidine cholestryl carbamate (GL-53) and 1-(N4-spermind)-2,3-dilauryl glycerol carbamate (GL-89).

The vectors of the invention may be targeted to specific cells by linking a targeting molecule to the vector. A targeting molecule is any agent that is specific for a cell or tissue type of interest, including for example, a ligand, antibody, sugar, receptor, or other binding molecule.

Invention vectors may be delivered to the target cells in a suitable composition, either alone, or complexed, as provided above, comprising the vector and a suitably acceptable carrier. The vector may be delivered to target cells by methods known in the art, for example, intravenous, intramuscular, intranasal, subcutaneous, intubation, lavage, and the like. The vectors may be delivered via in vivo or ex vivo applications. In vivo applications involve the direct administration of an adenoviral vector of the invention formulated into a composition to the cells of an individual. Ex vivo applications involve the transfer of the adenoviral vector directly to harvested autologous cells which are maintained in vitro, followed by readministration of the transduced cells to a recipient.

In a specific embodiment, the vector is transfected into antigen-presenting cells. Suitable sources of antigen-presenting cells (APCs) include, but are not limited to, whole cells such as dendritic cells or macrophages; purified MHC class 1 molecule complexed to beta2-microglobulin and foster antigen-presenting cells. In a specific embodiment, the vectors of the present invention may be introduced into T cells or B cells using methods known in the art (see, for example, Tsokos and Nepom, 2000, J. Clin. Invest. 106: 181-183).

The invention described and claimed herein is not to be limited in scope by the specific embodiments herein disclosed, since these embodiments are intended as illustrations of several aspects of the invention. Any equivalent embodiments are intended to be within the scope of this invention. Indeed, various modifications of the invention in addition to those shown and described herein will become apparent to those skilled in the art from the foregoing description. Such modifications are also intended to fall within the scope of the appended claims.

Various references are cited herein, the disclosures of which are incorporated by reference in their entireties.

What is claimed is:

1. An isolated genomic nucleic acid molecule, said nucleic acid molecule selected from the group consisting of:

(a) a nucleic acid molecule consisting of a nucleic acid sequence which has at least 99% identity to the nucleic acid molecule of SEQ ID NO: 3 and which encodes a polypeptide having the amino acid sequence of SEQ ID NO: 1, wherein said polypeptide inhibits the action of insulin;

(b) a fragment of the nucleic acid molecule of (a), said fragment comprising at least nucleotides 19611-20633 of SEQ ID NO: 3 and which encodes a polypeptide having the amino acid sequence of SEQ ID NO: 1, wherein said polypeptide inhibits the action of insulin, and;

(c) a nucleic acid molecule that is the full complement of the nucleic acid molecule of (a) or (b).

2. A nucleic acid construct comprising the nucleic acid molecule of claim 1.

3. An expression vector comprising the nucleic acid molecule of claim 1.

4. An isolated recombinant host cell comprising the nucleic acid molecule of claim 1.

5. A method for obtaining a polypeptide which inhibits insulin activity, said method comprising:

(a) culturing the recombinant host cell of claim 4 under conditions that provide for the expression of said polypeptide and (b) recovering said expressed polypeptide.

6. A composition comprising the nucleic acid molecule of claim 1 and a carrier.

7. A kit comprising the nucleic acid molecule of claim 1.

8. The kit according to claim 7, in which the nucleic acid molecule is labeled with a detectable substance.

9. A microarray comprising one or more of the nucleic acid molecules of claim 1.

10. A kit comprising the microarray of claim 9.

11. A method of detecting the presence of a nucleic acid sequence of SEQ ID NO: 3, its complementary sequence or fragment thereof in a sample, said method comprising contacting the sample with the nucleic acid molecule of claim 1 and determining whether the nucleic acid molecule binds to said nucleic acid sequence in the sample.

12. A method of identifying a nucleotide sequence variant of the 5'-noncoding region, 3'-noncoding region or intron region of SEQ ID NO: 3 or its complementary sequence comprising:

(a) isolating genomic DNA from a subject and (b) determining the presence or absence of a nucleotide sequence variation in said genomic DNA by comparing the nucleotide sequence of SEQ ID NO: 3 with the nucleotide sequence of the isolated genomic DNA and establishing if and where a difference occurs between the two nucleic acid sequences thereby identifying a nucleotide sequence variant of SEQ ID NO: 3, or its complement.

13. The method according to claim 12, wherein said variant encodes a protein that inhibits the action of insulin.

14. An isolated nucleic acid molecule consisting of a non-coding region of the nucleic acid molecule of claim 1, which non-coding region is selected from the group consisting of the 5'-noncoding region shown in sequence segment 20633-38587 of SEQ ID NO:3, the 3'-non coding region shown in sequence segment 1-19610 of SEQ ID NO:3 and the intron region shown in sequence segments 20141-20516 and 19743-20062 of SEQ ID NO:3, or a full complement of said isolated nucleic acid molecule.

15. An isolated nucleic acid molecule consisting of a fragment of the nucleic acid molecule of claim 1, said nucleic acid molecule consisting of a nucleic acid sequence selected from the group consisting of:

(a) a sequence of at least 4000 contiguous nucleotides within a region consisting of the sequence of nucleotides from position 20634-38587 of SEQ ID NO:3 and (b) a sequence of a least 600 contiguous nucleotides with the region consisting of the sequence of nucleotides from position 1-19610 of SEQ ID NO:3.

16. An isolated nucleic acid molecule consisting of 20-300 contiguous nucleotides in sequence segments of a non-coding region of the nucleic acid molecule of claim 1, which non-coding region is selected from the group consisting of the 5'-noncoding region shown in sequence segment 20633-38587 of SEQ ID NO:3, the 3'-non coding region shown in sequence segment 1-19610 of SEQ ID NO:3 and the intron region shown in sequence segments 20141-20516 and 19743-20062 of SEQ ID NO:3, or a full complement of said isolated nucleic acid molecule.

* * * * *

SEQUENCE LISTING

```
<160> NUMBER OF SEQ ID NOS: 5

<210> SEQ ID NO 1
<211> LENGTH: 108
<212> TYPE: PRT
<213> ORGANISM: Homo sapiens

<400> SEQUENCE: 1

Met Lys Ala Leu Cys Leu Leu Leu Pro Val Leu Gly Leu Leu Val
1               5                   10                  15

Ser Ser Lys Thr Leu Cys Ser Met Glu Glu Ala Ile Asn Glu Arg Ile
                20                  25                  30

Gln Glu Val Ala Gly Ser Leu Val Phe Arg Ala Ile Ser Ser Ile Gly
                35                  40                  45

Leu Glu Cys Gln Ser Val Thr Ser Arg Gly Asp Leu Ala Thr Cys Pro
        50                  55                  60

Arg Gly Phe Ala Val Thr Gly Cys Thr Cys Gly Ser Ala Cys Gly Ser
65                  70                  75                  80

Trp Asp Val Arg Ala Glu Thr Thr Cys His Cys Gln Cys Ala Gly Met
                85                  90                  95

Asp Trp Thr Gly Ala Arg Cys Cys Arg Val Gln Pro
                100                 105

<210> SEQ ID NO 2
<211> LENGTH: 593
<212> TYPE: PRT
<213> ORGANISM: Homo sapiens

<400> SEQUENCE: 2

Met Ala Pro Ser Gly Leu Lys Ala Val Val Gly Glu Lys Ile Leu Ser
1               5                   10                  15

Gly Val Ile Arg Ser Val Lys Lys Asp Gly Glu Trp Lys Val Leu Ile
                20                  25                  30

Met Asp His Pro Ser Met Arg Ile Leu Ser Ser Cys Cys Lys Met Ser
                35                  40                  45

Asp Ile Leu Ala Glu Gly Ile Thr Ile Val Glu Asp Ile Asn Lys Arg
        50                  55                  60

Arg Glu Pro Ile Pro Ser Leu Glu Ala Ile Tyr Leu Leu Ser Pro Thr
65                  70                  75                  80

Glu Lys Ser Val Gln Ala Leu Ile Lys Asp Phe Gln Gly Thr Pro Thr
                85                  90                  95
```

-continued

```
Phe Thr Tyr Lys Ala Ala His Ile Phe Phe Thr Asp Thr Cys Pro Glu
            100                 105                 110

Pro Leu Phe Ser Glu Leu Gly Arg Ser Arg Leu Ala Lys Val Val Lys
            115                 120                 125

Thr Leu Lys Glu Ile His Leu Ala Phe Leu Pro Tyr Glu Ala Gln Val
            130                 135                 140

Phe Ser Leu Asp Ala Pro His Ser Thr Tyr Asn Leu Tyr Cys Pro Phe
145                 150                 155                 160

Arg Ala Glu Glu Arg Thr Arg Gln Leu Glu Val Leu Ala Gln Gln Ile
                    165                 170                 175

Ala Thr Leu Cys Ala Thr Leu Gln Glu Tyr Pro Ala Ile Arg Tyr Arg
            180                 185                 190

Lys Gly Pro Glu Asp Thr Ala Gln Leu Ala His Ala Val Leu Ala Lys
            195                 200                 205

Leu Asn Ala Phe Lys Ala Asp Thr Pro Ser Leu Gly Glu Gly Pro Glu
            210                 215                 220

Lys Thr Arg Ser Gln Leu Leu Ile Met Asp Arg Ala Ala Asp Pro Val
225                 230                 235                 240

Ser Pro Leu Leu His Glu Leu Thr Phe Gln Ala Met Ala Tyr Asp Leu
                    245                 250                 255

Leu Asp Ile Glu Gln Asp Thr Tyr Arg Tyr Glu Thr Thr Gly Leu Ser
            260                 265                 270

Glu Ala Arg Glu Lys Ala Val Leu Leu Asp Glu Asp Asp Leu Trp
            275                 280                 285

Val Glu Leu Arg His Met His Ile Ala Asp Val Ser Lys Lys Val Thr
            290                 295                 300

Glu Leu Leu Arg Thr Phe Cys Glu Ser Lys Arg Leu Thr Thr Asp Lys
305                 310                 315                 320

Ala Asn Ile Lys Asp Leu Ser Gln Ile Leu Lys Lys Met Pro Gln Tyr
                    325                 330                 335

Gln Lys Glu Leu Asn Lys Tyr Ser Thr His Leu His Leu Ala Asp Asp
            340                 345                 350

Cys Met Lys His Phe Lys Gly Ser Val Glu Lys Leu Cys Ser Val Glu
            355                 360                 365

Gln Asp Leu Ala Met Gly Ser Asp Ala Glu Gly Glu Lys Ile Lys Asp
            370                 375                 380

Ser Met Lys Leu Ile Val Pro Val Leu Leu Asp Ala Ala Val Pro Ala
385                 390                 395                 400

Tyr Asp Lys Ile Arg Val Leu Leu Leu Tyr Ile Leu Leu Arg Asn Gly
                    405                 410                 415

Val Ser Glu Glu Asn Leu Ala Lys Leu Ile Gln His Ala Asn Val Gln
            420                 425                 430

Ala His Ser Ser Leu Ile Arg Asn Leu Glu Gln Leu Gly Gly Thr Val
            435                 440                 445

Thr Asn Pro Gly Gly Ser Gly Thr Ser Ser Arg Leu Glu Pro Arg Glu
            450                 455                 460

Arg Met Glu Pro Thr Tyr Gln Leu Ser Arg Trp Thr Pro Val Ile Lys
465                 470                 475                 480

Asp Val Met Glu Asp Ala Val Glu Asp Arg Leu Asp Arg Asn Leu Trp
                    485                 490                 495

Pro Phe Val Ser Asp Pro Ala Pro Thr Ala Ser Ser Gln Ala Ala Val
            500                 505                 510
```

-continued

```
Ser Ala Arg Phe Gly His Trp His Lys Asn Lys Ala Gly Val Glu Ala
    515                 520                 525

Arg Ala Gly Pro Arg Leu Ile Val Tyr Val Met Gly Gly Val Ala Met
530                 535                 540

Ser Glu Met Arg Ala Ala Tyr Glu Val Thr Arg Ala Thr Glu Gly Lys
545                 550                 555                 560

Trp Glu Val Leu Ile Gly Ser Ser His Ile Leu Thr Pro Thr Arg Phe
                565                 570                 575

Leu Asp Asp Leu Lys Ala Leu Asp Lys Lys Leu Glu Asp Ile Ala Leu
                580                 585                 590

Pro
```

<210> SEQ ID NO 3
<211> LENGTH: 38587
<212> TYPE: DNA
<213> ORGANISM: Homo sapiens

<400> SEQUENCE: 3

| | |
|---|---:|
| gtgcctctag aggatcccca tgcacagatt agaaaggtga gtcttggccg ggcagggtgg | 60 |
| ctcgtgcctg tcatcccagc gctgtaggac gccgaggtgg gtggatcacc tgccaggagt | 120 |
| ttaagaccat cctggtcaac atggcgaaac ccctctctac taaaaataca gaaattagcc | 180 |
| agtcatgatg gcgggcgcct gtaatcccag ctatttgaga ggctgaggtg ggagaatcac | 240 |
| ttgaacccag gaggcggagg ttgcagtgag ctgagatcgc gcactgcact ccagcctggg | 300 |
| cgacagagtg attctgtctc aacaaaataa ataaataaac aaacaaacaa ataaataagg | 360 |
| gtgagtcttg ggctgcaggg tatggggcac caaaatgagg taccggtccc caggcacaga | 420 |
| ctcaggatgg ggaacctggg gtgagaaggg agggtgcaga ctcagagggc tgccgggaac | 480 |
| tgggctcctt ctccccgccc catccctga cccaaagcct tttgctccag caactgggct | 540 |
| ccaggggagc ccaccagccg gagccagggc gaggactgcg tgatgatgcg gggctccggt | 600 |
| cgctggaacg acgccttctg cgaccgtaag ctgggcgcct gggtgtgcga ccggctggcc | 660 |
| acatgcacgc cgccagccag cgaaggttcc gcggagtcca tgggacctga ttcaagacca | 720 |
| gaccctgacg gccgcctgcc caccccctct gcccctctcc actcttgagc atggatacag | 780 |
| ccaggcccag agcaagaccc tgaagacccc caaccacggc ctaaaagcct ctttgtggct | 840 |
| gaaaggtccc tgtgacattt ctgccacccc aaacggaggc agctgacaca tctcccgctc | 900 |
| ctctatggcc ctgccttccc aggagtacac cccaacagca ccctctccag atgggagtgc | 960 |
| ccccaacagc ccctctccca gatgagagta caccccaaca gcaccctctc cagatgagag | 1020 |
| tacacccccaa cagcaccctc tccagatgag agtacacccc aacagcaccc tctccagatg | 1080 |
| cagccccatc tcctcagcac cccaggacct gagtatcccc agctcaggtg gtgagtcctc | 1140 |
| ctgtccagcc tgcatcaata aaatggggca gtgatggcct cccacatttg tccccttctt | 1200 |
| ggaggcctgg ctgggtctgg tctctgggtg tggcacatgg gagctgggaa ttccagagtc | 1260 |
| tgatgcctga gaccaccttt gaaagttggg acatcagatc tttggccggg tgtggtggcc | 1320 |
| catgcctgta attccagcac tttgggaagt caaggcaggc gaatcatctg aggtcaggag | 1380 |
| ttcaagacca gcctggccaa catggcaaaa ccccgtctct attaaaaata caaaaattca | 1440 |
| gccgggcacg gtggctcacg cctgtaatcc cagcactttg ggaggccaag gcaggcggat | 1500 |
| cacaaggtca ggagatcgag accatcctgg ctaacacggt gaaactccgt ctctactaaa | 1560 |
| aatacaaaaa attagccggg cgtggcggcg tgtgcctgta gtcccagctg ctggggaggc | 1620 |

```
tgaggcagga gaatggcgtg aacccgggag gtggagcttg cagtgagccg agattgcgcc    1680
actgcactcc agcctgggcg acagagcgag actccatctc aaaaaaaaaa aaaaaacaaa    1740
aacacaaaaa ttcgctgggc gtggtggtgc acacccgtaa tcctagctac tcaggaggct    1800
gaggcaggag aagtgcttga acctggggagg tggaggttgc aatgatctga gatcacgcca   1860
ctgtgacaga gcgagacccc aactaaataa atttaaaaag aaagaaagaa aattgggagc    1920
aagcagatgt ggtggctcat gcctgtaatc ccagcacttt gggaggctga attgagccga    1980
tcacttgaga ccaggagttc gagaccagcc tggccaacat agtgaaaccc cgtctctact    2040
aaaaaaaaaa tacaaaaatt agccaggcac ggtggcatgt gcctataatc ccagctactc    2100
gggaggctga ggcaggagaa tcacttgaac ctgggaggca gaggttgcag tgagccagga    2160
tcgtgctact gcactccagc ctgggtaaca gagtgagatt gcatgtcaaa aaaaaaaaaa   2220
agaagaaaaa agaaacaaat tgaggagcaa ctgaagtaga attcgatctc ccgttttat    2280 tttttcctgc tctatgacac ggagaatgtg caggacatga agcctctgag gtccaatggc    2340
cccttggaat actgtagggg aaggcggtgg atcaccctga ggccgggagg gcgtgagttg    2400
actcatggaa gtacccagag cagggcttag tacacagaag gcactcagta agtgctggct    2460
ggctggacag gctgatgggg agtgggcccg gtcaaccgga ggccatttcg ggtctggagg    2520
tgttaaccct actcagggtc tgggaggctg aggtggcacc agcctcacgc tcggccaagg    2580
tcgacccatg ccggaggcca cgggagggag gccaggagca cagggtcccc tctccacact    2640
cctctaccag tggctcaggc caacactggg gtcattgcac ctcttccctt tcccctgaca    2700
acacctccag gtccaagacc ataagaaatg ccagtgggct ctgctgtcaa acggcgctca    2760
caatcactca ctgctcaccc cttctgccac tgcctcgact ggagcagtca cctccgcccg    2820
gggctctctc ttcactgccc cctttccaga agtttcctcc agctcagata aaaggccaaa    2880
gccagctgcg cacagtggct catgcctgtc atcccagcgc tttgggaggc tgaggtggga    2940
ggactgcttg agttcaggag tttgaggcca gcctgggcaa catagtgagg ccccatctct    3000
acaaaaaata caaaaactag aggtgtagtg atgggcaact tggtcccagc tgcttgggag    3060
gccgaggtgg gaggattgtg cccctgctct cagcctgggc gacagtgaga acctgtctca    3120
aaaaaaaaga agaagaaaag agaaaaagcc agccaggtgc ggtggctcac gcctgtaatc    3180
ctagcacttt gggaggccaa ggcgggcaga tcacttgagg tcaggagttc cagaccagcc    3240
tggccaacat ggtgaaaccc cgtctccact aaaaatacaa aaattagctg ggtgtggtgg    3300
cggatgccta tagtcccaac tattcaggag gctgaagcag gagaattgct tgaacccagg    3360
aggctgagat ctgagatcgc accactgcac tccagcctgg gcgacagagt gagactccat    3420
ctctaaataa taataataat aataattaat ctgtgtgacc atgggcacat gacttctttt    3480
ggaacctgcc tgtgaaatga gctgatgctg cttgcccagc tcaccaaggg ctggtgcctg    3540
gctcctcctc ctcctcttcc tctcacccac ccacctggag ggtccagggg aagaccttcc    3600
ttgcagccca gagcaccgta agttagagct gctgtgatca gaagctgccg aaccacaggc    3660
tcttctttct cttcatcctc ccttgcccca acccgggcc cagcctcata accctacagc     3720
ttgttcaaac gttttccctt ctcctcaagc ccctaactc accctcggtg gccggtgggg     3780
atggggcgtg ggaacagacc ctgggccctg cactcccagc ttacaaattc ccgcagcccc    3840
tcttcctccc tcccgatttc tctgacatcc ctcacagccc cgcctctgga cagaagaatg    3900
gcccctgccc tggccggccc tggaagcccc tctcgccagg gtctcagagg acctgcctgg    3960
ggctgcttag cccaaagcgt cctgcatttt gctctgaaat ccagcttctc agacaccatg    4020
```

```
ttcccctccc tccgtccccc atccaggact gtggtttctg tgtctgtgca gacgcccaga    4080
cctccctcca gaactccaga ccccaaaccc caagacctgt gcatctgctg ccccctaga     4140 cgcctccccc tcattccaga ttcaggctat catcctgccc aagccctctc ccggcgcctc    4200
cctccacctc caacagccaa cagctattcc aggatcagcc ctggggctat gtgtggtggt    4260
tgctcaatgg tttcattcat cctagagacg ccaccttctc cccagtgtgc tgaagcccac    4320
cctgctcaat gcctcttgct aggatggctg agactgccct gaccaagccc tcagccctgg    4380
tccaccaggc agtccaacag agcatcctaa acaaatctag aggtgacacc gacccctttg    4440
gcccttctca taaccagtga ggggagccca gctgacagtc cctgcagttc ctttttctgaa   4500 cagacctgtc tgttcacatt ctgggggcg gtggaaagga agcagggaag attggatcat     4560
ggttccccca aaaatctgg aagaactttc cttgggggag aggaggagtt atcaggaacc     4620
aagtgtggtg aacaaaaagg gaaaggaaaa ttgcctgagg tgtaatacat tactttttt    4680 ttcttttta agacagggtc tcactctgtt gctcaggctg gagtgccagt ggtgtgatct     4740
tggctcactt caacctccgc ctcccaggtt aagtgatcc cctgccctta gcctcccaag     4800
tagctgggat tacaggtgcc tgccaccacg cccagctaat ttttgtattt ttagtaaaga    4860 tggggttttgc catgttgacc aggttggtct caaacttccg gcctcaagtg atctgcccac   4920
ctcggcctct caaagtgctg ggattacaga cataagtcgc cacgcctggc cttatttcaa    4980 attctttag acaaggtctc actatgttgc ccaggctgga caccaaccc tggcctcaag     5040 cgatccttct gcctcggcct cctgaatagc tgggactcca ggtgtgcacc actgcacccc    5100
acttatttta aaattttttt aacaagggaa atgtgtttgt atcatcctgg actttaaaat    5160
taactttaaa gtattgacca gactggccaa cacagtgaaa cctcatctct actaaaaata    5220
caaaaaatta ggtagctggg actacaggaa tgcacctcca tgcccagcta atttttgtat    5280
ttttagtaga gacagggttt caccatattg gccaggctgg ctcgaactcc tgacctcgtg    5340
atccgcctgc ctcggcctcc caaagtgctg ggattatagg cgtgagccac cgcgcctgac    5400 cttttttgttt tttagatgga gtttcgctct tgttgcccag gctggagtgc aatggtgcaa    5460
tctcggctca ctgcaaccct cacctcccgg gttggagcga ttctcctgcc tcagcctccc    5520
aagtagctgg gattacaggc atgtgccacc acacccggct aatgttttct attttagta    5580 gagacggggt tttgccatgt tagccaggct ggtctcgaac tcctgacttc aggtgatcca    5640
cctgcctcag cctcccaaag tgctgggatt acaggcgtga ccaccgcac gtggcccctc    5700 ctggtgattc tgatacccta aagcctgcat ctcaatctaa ggtccccagg aatcccctgg    5760
gggcctcgct aaaatgcacc ctcagattca gcagctctgg ggtgggcctg agactgcatt    5820
atggaccaac tcccagttga tgctgctact gctgatctac agaacacact ttgatttggc    5880
tcacgcctgt aaccccagca cttacggagg ccaaggtgga aggattgctt gaggccaaga    5940
gtttgagacc agcctgggca acctaataag agccccatc tctacaaaaa tttttaaaa    6000 attagctggg catggctggg cgccatggct cacgcctgta atcccagcac tttgggaagc    6060
cgaggtgggc agatcacgag gtgaggagat cgagaccatc ctggctaaca tggtgaaacc    6120
ccgtctctac taaaaatacg aaaaattagc caggtgtggt ggtgggcacc tgtagttcca    6180
gctactcggg aggctgggc aggagaatga catgaaccg ggaggcggag cttgcagtga      6240
gccgaagccg agatgctgcc actgcactcc agcctgggcg acagaacaaa accctgtctc    6300
tgaaaaatat aataaatgag ggaagaaggc aaacaatctc cctctgcctg ttttctaggc    6360
```

```
acacggtgac acccactcct ttacatgttg tctgtggttg cattcagtac atcagcggag    6420
taatggggca agagcacatg gcggcacagc agtggctcac gcctgtaatc ccagcacttt    6480
gggaggctga agtgggcgga tcacctgaga tgaggagttc gagaccagcc tgaccaacat    6540
ggtgaaaccc catctctact aaaaatacaa aaattagccg ggtgtggtgg gaggcacctg    6600
taatcccagc tacttgggaa gctgaggcag gagaatcacg tgaacccaag gtggaggttt    6660
gcagtgaggt gagatggtgc cactgcactc cagcctgggc gacagagcaa gactctatct    6720
caacaaataa aaaaaataat aataaagacc acatggcata aaatattgcc catctggcac    6780
tttgcgcagt ttgcccaccc ccagtctaaa ggcgtctgtc tcagcctgat gcgtctccca    6840 ggacccatg cccctccag cctgcagaca gcctccaacc gtgattccag aacctgccag     6900
catttcccac caactccttt tgccgggttt atttctcccc accactcctg gtctcactca    6960 acccccaac cctatggcca gacccgcccc cactctactg taaacacatt cggacctggc     7020
ctccctcccc agcctgggc agggctgtgg ctcaaggtac tgagtggatc taaggccgcc    7080
acacaagaca caagacacac gtggggaggg gctctctgta tcctttatct ccggcagggt    7140
cagcggccct ccagggcccg gtctcgagcg atgactgcct cctcgaactt gatcatgagc    7200
gtggtgccct tgtgccagtg cgccgtgacc ttggcaggga agccgctgtg tgtgagcacc    7260
gcctccacga tgcccgccgt gaagctggcg cagttgagcg tgctgttctc cttgggcacg    7320
gagatgtagg tgttgatgag cggctcgcgc tcgatgatgt agaaggtgcg cgcgtcatcg    7380
ttggcctgct ccagcttgtc cgcctccttg ccgaagagcg ccttccacac ggcgcccttg    7440
acgaagagca acgcgcctag caccttggtc tcacgccggg caccctttc gcgcgccacc     7500 agcgcatcca gcacgcgcgc gcccacctgg cggcccagcg cggccaggcg cgactgcagc    7560
tcggccacgg agaagacgcg gctctggcag tgctgtacca gctcggagaa cagcagtgcg    7620
aaggcgctca ggctcacctc ggtgcgcggc gcgccagcg cgcgctccag cagcgccgac     7680
ttcccgcgcg tgaagcgcgc ctccatgccg ccgccaccct gcggggagac caggaagtgc    7740
aggtgtcagg ggcaatggga aggggagcag gccggggagga aggaggggag aaccgcgagg    7800
ggccctggga caccctcgac ccatgccact gttgtgtgct ccagtgccga cttcccactt    7860
gcaaagagat gcgcgtaaaa cacgcctcga ttcacgtaa ccagataaat caagggaggg     7920
gggagtctta taccctcggc aggcagcggg ctagcggag tggggacaag gtgggaggag     7980
agacacgagg gggaacagaa gaggaggccg aaaccaccca accctcgggc atgcagacgg    8040
ttcaattgcg aaagcgcctt cctgcccgct ccgccaccta caggagtaac tagaaaacta    8100
gtgtatgggg ggaggggcgt cagatctagg gcagggaggt gacaaagatg aggcaccacg    8160
aggggatatg ggcagtcgct cctgcccgc cctgcgctcc agcacagacg accctcggga     8220
actttcctgc cggcccctg cggaaagcca gagtaaaggg ggtggagggt gggagtgggg     8280
taggagcgtg tcaagaccaa aagccaggag ggttgggggc tttaacaggg gggatccgtg    8340
gggccaggca ggaggggcgg gtaacccca acccaagcc ctcaggcagg cagctccgat     8400
gtgtcacgca ggaacccttc gtcctttgag acgcggatgg gcctgggttc tgaaggctgg    8460 gaggagggc ccagaggtgt tgggagcctc ccaccccgt gctctccaga aaggaagctg      8520
gatgctgagc aactgtggtc ctcccatcag ctgtcggtgc gggagaggg agatgggta     8580 gggggctcct gaagagaaat ggggtgggga gcggcgccg agacgggatc ggaggggcag    8640
ctgagaaccc gccccacca tgcatgggga ggtgtgtgga tgctaagccg accccaacga    8700
ggtctgcgtg ggaggtggga gaaccagcgg ggaggggtgt cccaggggct ccgggccgcc    8760
```

```
cccgccccag catgcagatc cgtccgtggc gagggccctg ggcgcgcgag atgggagagg    8820
gatcgttaag accccaccac cgggctgcga tgggggctga agtgagctga actgccgtag    8880
ggtcagggcc ccgcgaccct cgccccgtac ctctacactg gggagaaacc caccctcctc    8940
gcagcctcct gagggggggcc gaagcgagcg ggctcgggat cgcggacgcc gagacccag    9000
cccgggaccc acacgcccgc ggggaagggg ccggggagcg gacgaggccc ggcgcgggca    9060
gggggtggg tagggtctca ccaggaaccg cagcagtctg ctcggccgag ctgctttacg     9120
gcgccgtaaa aggcgctgcg tgcgcaggcg ctcgacgggc caggcgtgtg ggcggggcgc    9180
gcgcagcggt gcctgagagc ggccgcaggg gggcgcgcga gtccgcggag ccggacccag    9240
ggacgtggcc cacggccgtg atggctgctc cgcgcgtggc cagggtctcg ctggctctgg    9300
gtggcccacg ctggagggga cgcttgcagg cctagtcacc tgctcagggc gcacgtatga    9360
caatgggcca atgtataccc ttgcacatgg acacacctgt tggcttttcc aggcactcct    9420
atgtccttgg ggatgggttc aattgtctca agtgcatcca tgtggcccgc ggtggctccc    9480
gcctgtaacc ccagcatttt cggaggcgga ggtgggagaa tcacttgagg ccaggagttt    9540
gagaccagcc tggacaacat agctagactc ccacttcttt aaaaaaaatt agccaggtgt    9600
ggtggtgtga acctgtaatc ccatctactc gggaggcgga ggcaagagga tcgcctgagc    9660
ccaggaggtc gaggctgcaa tgagtcatga tcgtaccact gccctccagc ctgggtgata    9720
gagcgagacc ctgtctcaaa aaaacaaaaa caaacaacaa caacaacaaa tcaagtgcat    9780
gcatgagcgg tggacatagt accttagggt catgtacact catggataca tgctcaatgg    9840
catagataca ctcacgggca caattacaca cgtgggtaca cgcttagggc ttgtatatat    9900
ccgtggtccc aggtacactc agggagatgt tgtatgctca ggggcaccca ctctgggaca    9960
cagggaagac acagggaatg agttactcat tcacagatgc acaggtactc acgcagggca   10020
ctcagtctcg cccaccctgg tgccccgggg tcattgtcac gtgcagactc tccctctccc   10080
caggtcccaa aaccccctccc cttgcccccag taacaggtcc catagcgacg ctgttttccc   10140
ttgactttat ttatcttcat aagtcacaaa atgtgagtgc agagataaat gtctgtgtgc   10200
atgtgccctg agcacacagg gtggcataac tcggcacact cataatgaca cagccgttca   10260
cccagccaca gatagtgaca gggcacacat ggcgacaccc acatgtacgg agataaatct   10320
cccccaccat gacatgggta gacagaaaac acgccgcagt atactctagt atgtttacac   10380
aaacagggag acaggcccgt gcaatgcatg tcaccaacac ccacactcag agtgacatct   10440
gctggaggtg ctcagacaca gccacccacc gtgacatgcc gagactcaca tatgtcacat   10500
gacacaggca tgcatgccac attcactgtg actctcagtc ctattcattc atcacctttc   10560
tgggagatac actgaaatgt ccacccttg caaaatgcac acacacgcgc acgcacacac    10620
gcacatacac gaacacacgc gcacacacgc acacacgc cgcaggtgt acacacacac      10680
gagcaactcc gagacactca ttcaccatga ctcgaggttt ttctatacgt gggacgaggg   10740
gcaggttcac actaggctgg ggggggggg tcatttcccg tcttcgttgg caggtgcagc    10800
cccatcttcc aagttgtggc tttggctgcc acaatgtcct ctcatttatt gaggtgagga   10860
ctctggggat ggggagagac ccacagtgag gcagatcccg cccctgggag aggagctggg   10920
gctaaatctg aagccccacc caccctcctc cacctcctgt cggggcgcca acttacgtgg   10980
cattttctgc agcacctcca agattttctg taccttttgtg tcaatgttt ttatgcctag   11040
ggggcgggga gggttgggtg ggaacagata agtcaagctg cggtggagcc tcaaacaaag   11100
```

```
cccccacctt ccttggaagc acccccctg ccccacaccc acctgggat acagcagagc    11160
ccatggattt ggggttccca ggagcctttc aatacccaca gagcaaccca gatggtaaca   11220
cccatcgccc ctccacaact tgagctttgg gagggtagga cccggctt  ctcctcccct    11280
gaatcccctg ccccagctc agctccgggc attggtgaca aataaccccc atagaaggcg    11340
agactacaca ggcacctgct aatgtcgtct ctaatctatc aatcttgctc ctgaccatgg   11400
tgatgctctg ctgaacggaa tcccagcctc tcttctgtct ctcttcgcat gcttgtacgg   11460
agtttgagac tgagggcatg aaacaggggt gtctgtgcat ccatccctct ccagaccccc   11520
accatgaccc cacgggtctc cctcagaccc tccgctcacc attccaaagc tcccttttaa   11580
agcccagcag ctccttggac atctcagcat ctgttcagga ggggcaggaa aatccttgaa   11640
gcacccaggg agagagagag agaaggacaa gggagaaagt ctaggccccc cagcaccctc   11700
ctcccaagaa gtactcactc ttcaccatga tgaaggctga caggatgatg cagaggacaa   11760
aggccagggc caggaggatg tacaggctca ggatggctct gtacaaccag cagggaccct   11820
gggtggagtc tgagggcggc ctgcactggg ctgggactgg agcaaagagg cagcaaagtg   11880
accttgaggg gccagcacca ccactcaaac catcctcact gtctctaaca ccatggacac   11940
ctcgctcctc tcaaaaccat cagcagctgt ggtcatgcag cttgtcatca tcgtcaacaa   12000
cactgccacc accagccacc ctcagcgatc taacaccgtc accatcacag accccctctc   12060
cagcattccc caacattgtc atcatcaaca gacctcatta gcacgtcaac agctgtcacc   12120
tcttccttcc ccatcgcttc ctcccttcca cgcagcccg  ggggccctgc agttgccgc    12180
ccacctgccc cttcccaagg tgatgggatg tgagcaggtg ggtgtctgct caccttggct   12240
cgtgggtcgt gaatgaccac cctttgcatg gtcctgattt ttgaaggcca aggtgatatt   12300
ctcatagtct gggtcatggg cacctgggag gggttggaga tctgctcaga gctctgtggt   12360
gtggagagtg gatccgggat cttgttttac ccaaccctt  gcactcaata aattgtaggg   12420
ggtgaaagat aaggagtgag aagctaaaat ctgctttttg gttaagtgga gcgggtgtgt   12480
gagagtttga gtgatcacac cacacacaca tccacacaca catccacaca tcttggaggg   12540
gaaggagccc ccggccccca cctttgaccc cttacctctc ccatctgaac tctccttctt   12600
tttttatttt tatttttttac agacagagtc tccctatgtt gcccaggcca gtctccacct   12660
ccagggctca cgcaatcctc ccgcctcagc ctcccaaagt gctaggatta cagacatgag   12720
caaaagcccc cggcccccca atctctcctt cttaaccct  ccttccacc tcgagttccc    12780
taaccttgat tcttggctga acccccgtg tccttgtccc tgaaggctgg tgcttgcatc    12840
ttgacttcct ggtgcttgta gatttcctcc acttccatgg tccccagccc gcaaatttgt   12900
ccatacacgt ccccgcccac cggaaggtgt gggcagatga ggaaatctgg aggtgggggg   12960
aagaaagagg gggagcagcc tcctcttttc agggatccac gactctcgca ccctggggca   13020
ccctcattcc tgcccgatc aagaggctct gggagccaa gaggtctcag gaaggaccaa     13080
gaagaaaaac ctctagaccg ggagatggaa ttcgacactc ggaaatgtta caggaagctg   13140
tggtctctgt gtgtgtctgt gtctacctgg atggacctca ccctcctacc tcctctccat   13200
ttcaaaagag aagctgtgac acctcagtgt cccaactttt cgcgtaagag caaccaggct   13260
tggagacagg acccctgggt cccccacac  cttcctccct ccagcctcag ctccacccct   13320
cagctccacc cccaagaagt tcttctactt ctacaagtcc ccgtggagga aaagcacaga   13380
tgtgaggcaa cggaactaa  ccactggaac gccacaccca catctgggac tgaggacaga   13440
cccacatcct tccctccctc cccaaatccc ctgcttttat acaaccctgg aggaggctgg   13500
```

```
gtgcggtggc tcacgcctgt aatcccagca ctctgggagg ctgaggtggg tggatcatct   13560
gaggtcagga gtttgaaacc agcctggcta acatggtgaa accccgtctc tactaaaaat   13620
acaaaaatta gctgggcgtg gtggcgagcg cctgtaatcc tagctactca ggaggctgag   13680
gcaggagaat cgcttaaacc tgggaggcgg aggctgcagt gagcggagat cacaccattg   13740
cactccagaa tgggtgacaa gagggaaact ctgtctcaaa aaagacccct ggaggaacag   13800
tttcctctgc acctggaaac tccaggtttc tcattctcat ccatccatct gcttatctac   13860
ccagatactc tctctcacac atgtacacac acaggtctgc acacggacac acatcacaaa   13920
ctcatttgca tactatttgc attgtgacac tcagaaaaat agacacaagc atgcgttcac   13980
atgcccgcac tctgtctaga aggtgtctta gttcactttg tgtttatctg atcttgaaaa   14040
ctggggttac aaaaggcaca aagtagctgg gtatggtggc tcgctctgta gtcccagcta   14100
cccaggaggc tgaggtagga ggatcatttg aggccaggag tttgagacca gcgtgagcaa   14160
catagcaaga ccctgtctct ttaaatgttt tttaataatt ttttttgag acagggtttc   14220 actctgttgc ccaggccggg gtgcagcagc gtgatcatgg ctcactgcag cttgacctc   14280 cctggctcaa gtaatccttc gtcctcggct tcccgagtag ctgaaattac aggtgggcac   14340
gacttcacct ggctaatttt tctccttttt tgagatggag ttttgtgctt gtcacccagg   14400
ctggagtgca atgacgctat ctcagctcac tgcaacctcc gcatcccagg ttcaagtcat   14460
tctcctgcct cagcctccca gtagctggga ttacaggca tgcaccacca ccccgggcta   14520
attttgtatt tttagtagag acggggtttc cccatgttgg tcaggctggt ctcgaactcc   14580
tgacttcacg tgatctaccc gccttggcct cccaaagtgc tgggattaca agcatcagcc   14640
accgtggccc agtctaattt tcttattttt ttgtagagat gagggtctca atatgccgtc   14700
caggctggtc ttgatctcct gggttcaact gatcctccag ccttggtctc ccaaagtgct   14760
gggattacag gcatacatt ttatttttat tttttctgg ccaggtgtgg tggctcacgc   14820
ctgtaatcac agcactttgg gagtctgagg cgggcggatc acctgaggtc aggagttaga   14880
gacaccagcc tgaccaatat gataaaaccc tgtctctact aaaaatgcaa aaattaactg   14940
ggcgtggtgg caggcgcctg taatctcagc cactcgggag gctgagacag gagaatcact   15000
tgaacccggg aggtggaggt tgcagtgagc cgagatcgcg ccattgcact ccagcctggg   15060
caacaagagc aaaactccgt caaaaaaaa aaaaaaaaa gaaaaagaa gaaagaagaa   15120 agaaggaagg aaggaagaag aaaagaagaa aaaacaagta taagactgtc ttatgtgcag   15180
aaagtgatga tgttttggtt aaaaatatgt ggttaaattt cagacaactt gaatgttgag   15240
aaatgagcgt cgagatctgg tgaggataaa gttctgtttc ctaaaatatt gccaaatcct   15300
gtgtctccaa gaaagatcaa tttgataatg acttcatgcc agctgctcca tttggtctta   15360
gaaagaagtc agttactgag ctataggacc gccttctaat ggagcagacg gaccaattgg   15420
atgtgggctc tgccttgatg gacaggcaca gggggtggag ccacagcgtt gcacatttcc   15480
cgggcttggg tggggctgag acgcggctcc aggctctgga cttcctttga gaaaaaggtc   15540
acgctaaacc agaggcccac aagcaatcat gtcatgtggg aaacatctgc aaagctgcct   15600
gaccagcacc cgtcccttc atagggtaac attctcaatt ttcttttaag aaagaaaatg   15660
tgtgctagat ccagcaaacc ataagctagg gattgggtta cagtggacaa atgatccaga   15720
cccagccaac cagagtctaa gattgggcag agaggcgggc atttgagcaa gatccagcca   15780
atgaaacgct ggtctgggat ttttattggt ttaaccacgg gggaaaaagc attctctttt   15840
```

```
tttccagcc ctcactaggg ctgccacaat gggaggatgt aatgggagct gtgacaggga    15900
agaatttact tgagagcaaa ggcagtgctg agaaaatcag acccgagagg aagtctgggt    15960
cctggagaca tcatttgaga ccctggttcc aagccatacc tgaacctgtt gttctaaccc    16020
tgggcttgtc agttacacaa acaagaaact tccttttagt tttgcccaag ctagtttgaa    16080
gtggggtctg ttgtacttgc aagcagaaga atcttgcctt ggctggtctc tgtggcccac    16140
gcctgtaatc ccagcacttt ggaaggccga ggcaggtgaa tcacttaagg tcaggaattt    16200
gagaccagcc tggccaaaat ggcgaaatcc ccgtgtctac taaaaataca aaaattagcc    16260
aggagtggtg gtgggcgcct gcaatcccaa ctactcagga ggctgaagca ggagaatcac    16320
ttgaacctgg aggtggaggt tgcagtgagc tgagatcgtg ccactgcact ccagcctgga    16380
caacagagtg agactccatc tcaaaaagga agaagaagaa ggaggaggag gagaaggatg    16440
aggaggagga aggagggagt gaggagggag gagggaggag gatatcttgc ctaccacagg    16500
ggatctaggc attagctatt gaggaaattg aggctctaat agggggtttg cctgtccaca    16560
tcacctgggc agatatgacc tccaagtctg cactctgggg caggagaatg tctatgttgg    16620
aattgaggaa cctgaagaga gccctcttag gtttcagata caggactatt ggatgggggt    16680
ggagacaaat agttctgggg acaatggagc atccccgccc ccaacacaca cacacagcag    16740 taagggggcag ggacacacac aaggcactag actcaccctc tctggccctg gccatgcttc    16800
taactcagtg gtcctgccct accccatga ccactgtgga gtcaggagag agggtctggg    16860
aagggaatcc ctgggctgga gtctgggtgg ggtccctggc accagaagtg gttgtaatct    16920
ctgctcatgg ccaccagcat cagacagggg gctgggacca tcacaggggg tgggtggcag    16980
tgggaggaga gtccaaaaca tcctgcaaac cagaacctca ctctatcatc tgttgtccag    17040
gtgtgacatt tgagtctggg atcccttca agactaggtc ctaggaattc tgaagtctgt    17100
ggtgggaaat cagggactgg atggcaagac tcctgggtca ggcttcctgt agaactggac    17160
cccgaatcac ctgaatttgt gccccaggga gctgaggcgg gggatgctga ggcttttgcc    17220
cactagaaca ggggtcccca gccaccgggc attgggaacg gggcctcaca gcaggaggtg    17280
agtggtgggc gagcgagaga agcttcatct gtatttacag ccactcccca tcattcgcat    17340
taccacctga gctccacctc ctgtcagacc agcagcagca ttagattctc ataggagcaa    17400
gaatcccatc gtgaactgcg catttgaggg atgtagcttt ctcacttctt ataagaatca    17460
aatgcctggt aatctgtcgc tgtctcccat caccctcagc tgggaccatc tagttgcagg    17520
aacacaagct cagggctccc accgattcca cattatggtg agttgtagaa ttattttatt    17580
ctatattaca atgtcataat aataaaaata aagtgaataa taaatgtaat gcgcttgaat    17640
cacccagaaa ccatccccgc tccccccta ccccatacac acaccaactg tcttccatga    17700
aaacagtctc tggtgccaaa aaggttgggg atcgctgcac tagggtatca gatacttatc    17760
caggtgcagt ggggactaga gtcagaaatg caagagtctg cctggagcat gtgtgtgttt    17820
gtgtcctgca tcatctctgc ccaccatagt caaatctgcg attctccgtg cattggccgg    17880
gggggtggtg cctttctgtg tccaagagtg tctagggggca catgggtgtg tctgtggatg    17940
tggtgtctcc atgtggccgt ggtaggtggg ttgtgtactc tgtgtgtgca cgtggctgtg    18000
tatagctgtg tgtgcatgtg cagtatgtgc acgtcggtgc tgtatctaag tgcacatgtg    18060
gctactgatc aacagacatt tactgaacgt ctactgtgtt ccatgctcta ttctaaaccc    18120
tgggggcgct gggtgcagtg gctcatgcct gtaatcccag cactttggaa ggccgaggtg    18180
ggtggatcac ctgaggtcag gagtttgaga ctagcctggc caacatggtg aaaccccgctc    18240
```

```
tctactaaaa atacaaatta gctgggcatg gtggtgggca cctgtaatct cagctacttg   18300
agaggctaag gcaggaatat cacttgaacc caggaggcag aggttgcagt gagccgagat   18360
tgtgccactg cactccagcc tgggcgccag agtaagacct tgtctcgaaa ataaaaatta   18420
aaaaataggc caggcgcggt ggctcatgca tgtaatccca gcactttggg aggctgaggc   18480
gggtgaatcg cttgaggcca ggagctcaag accaacctag ccaacatggt gaaactcctt   18540
ctctactaaa aatacaaaaa ttagccaggt atggtggcga gcgcctgtag tcccagctac   18600
gtgggaggct gaggcaggag aatcgcttga acccaggagg cagaggttgc ggtgagccga   18660
gattgcacca ctgcactcca gcctgggcaa cagagcgaga ccctgtctca aaaaaaaaa   18720 aagaaagaaa gaaagaaaag agaagagggg agaggagggg aggggagggg agggggagggg   18780 aggggagggg aagggaaggg aagaaacgaa accctggggg ggatctagga gcagacaagt   18840
cccctgctct gtgttttcat aatctagtat ccaggaaggg gtaagcaccc tgcgtgtatc   18900
tggttgtaac taactactca caactgcact tgcctgtgtg aaaacgtgag cttgtgatga   18960
tgcgtgacgt caggtaggcg tccctgactc tccgtaaccc aactttgcct gtgccttggg   19020
gattcctcct tgcaggtagg aagtgagggg tacaggttcc agctctgggc tgagacatga   19080
ttcagggttc caccctgacc tggggctcct ggagtcttgg ggccctggag ggtcccgtcc   19140
actgcccaga ctgacccagg tcctcgatga agcctcatta tgaggactgg gggaaaagga   19200
cccagccact tcctggggag gtcggagacc ccagggtgag cgtcaaggta gcctcaaaga   19260
tgagacgtca cctcttgaag gcagccatga gccttgggtg gggacgtcac tagaggaagt   19320
tcaggcccta ttttcggagg aagcagttgg agaccccata ggaggaaggg cgatggggca   19380
gtagaaagtc gcggtgtccc cgccccctcc agcagctacg cgccccactc tcttggagac   19440
gctagatcag tccctccggg cctactaaag aaaccacgca gggctcagat ccgctccatc   19500
atcatcatca tcatcatcat catcatctcc aggtttattt ccagctcccc cgcaacccct   19560
ccggacctgg agccgcctcc gcccgcgctg tgcacgcgct gcgcgcgacc tcagggctgc   19620
acacgacagc agccgcgctcc ggtccagtcc atgcccgcgc actggcagtg acatgtggtc   19680
tcggcgcgca catcccacga gccacaggcg gagccacaag tgcagccggt gacggcgaag   19740
cctgcagccc ggaacacagg agcgtggact ctgagctggg aggctgaggg tgggagcggg   19800
aggggggtgg ggagcgcgga ggggggttgg ggggcgggg gtgggacgg ggacggctgg   19860 aggctccaac cactgaatgg gcactggagg caggagtga gggtgacac cagtgtccag   19920 atggtgggcg gagaaggctg ggagtcagga ccaagatcct aggggagtag aggctggaca   19980
cggggaacgt ggcggggagg gggcattccc aggggacttg gaacagaaat gggcgcctgg   20040
acaacagtct cctgcactca cctcgggggc aagtagccag gtcccccctg gaggtgacgc   20100
tctggcactc caggccaatg ctgcttattg ccctaaatac tgggggcag gaggaaagga   20160 gacaggggga gctgtgagac caaacggtcc ctccccatc ctccctagc cctgttggtt   20220 tggagctagg tccctgtggg cataggagct cactggcctc caggaccctg tcttgagttg   20280
ggtgttttgg agtaagggaa ggtttggagt gagagcgggg attgggttg gagccgtgga   20340 taaggtgggg acagtcggag gggttgggag tggagttggg gttgaattta tgatctggtt   20400
ggatttgagg atgagatttg gtgagcgctg gggctgggtt ggagtcaggt ctgtgccagg   20460
gatcagtgag gtctctgaga ccttgggga gcttgcccaa gtggggggtc ctcacttagg   20520
gagccggcga cctcctggat cctctcattg atggcttctt ccatggagca cagggtcttg   20580
```

```
ctagacacca acagcccag gacagggagg aggaggagac agagagcttt catcctgcag    20640
gcgctgaaag agggaaccaa gagacccaca gctggatcag ccctgccctg tggggaagat   20700
ccggcccatg gagggagtag gatctgcccc tggacctgga cccctgtccc ccatgtggg    20760
ggacagggat ggaggctcag ccttgacccc agcctccccg ctggtgccat ggcaagcgca   20820
ggagcagctg tcacttaccc tctcggtggg ctcagctaac caaatccggc acacgaattc   20880
ctgcaccgca gctcttttctt tgaggcctct tggggtgggg cttcctggct tggctaataa  20940
gtccctgggc ccccaaccct ccggtcccac atccggggcc aagaggaagc ccctgagcag   21000
acagtaaggg ctggaggagg aagggagcct tcccacttcc aacagggcct ccgtcttcat   21060
gtccagagac tggtcaggag gtggtgcccc agggataatg ccaggggctg tggtctgagg   21120
aacaggtaga caagcagagt tttgcatgca agggtggctg atgcaaacat gacaaaatta   21180
atgcctcttg ctaggcatgg tgcggacaag cacttgtagt cccagctact aaggaggctg   21240
acgtgagaga attgcttgag cccgggagtt cgaagctaca gtgacttatg atcacagcac   21300
tgcactccag tctgggcaac agagcaagac cacttctcta aaatagtaat aataattatg   21360
tctctgggtg agaatgacat accacattca tacccaaatg cccatgagca atagaactgg   21420
taaataaaat catggtttat ggccggtggc tcacgcctgt aatcccagca ctttgggagg   21480
ccaaggcggg cggatcactt gaggtcagga gcttgagacc aacctggcca acatgatgaa   21540
accctgtctc cattagacat acaaaaatta actgggcgtg gtggcgtgtg cctgtaatcc   21600
cagctacttg ggaggctgag gtgggagaat cacttgaacc cgggatgtgg aggttgcagt   21660
gcactgagat cgtgcccctg cactccatcc tggatgacta gcttgggcac catagcaaga   21720
ctccatctca aaagaagaa agaaaaatca tggtttattc catcaatggc atcacctgca    21780
acagaagttg gaaagccatt gctcatgggc caagtccagc tcatgtttct tcttggacca   21840
cccatgagct tggaatggtt attacatttt tatttgttct ttgtttcag tacaacgggc    21900
cttttgtggt aaaatacata taacatacaa cttaccatta taacttactt ttttctttttt 21960
tgagacggaa tcttgctctg tcgcccaggc tggagtgcag tggcgcgatc tcggctcact   22020
acaagctccg cctcctgggt tcacgccatt ctcctgcttc agcctcccaa gtagctggga   22080
ctacaggcgc ctgccaccac gcccagctaa ttttttgtat ttttttttttt ttagtagaga  22140
tggagtttca ccgtgttagc caggatggtc tcgatcccct gaccttgtga tctgcccgcc   22200
ttggcctccc aaagtgctgg gattacaggc gtgaaccacc gtgccgggcc ttttttttt    22260
ttttttgag acgggtctt gctatgttgc ccaagctagt gtcagactcc tggcttcaag     22320
taatcctccc accttggact ccccagtagc tgaagctaca ggtatgcacc atcttgttcc   22380
attttaacca ttgcttttgt ttgttctttt gtttcagagt ctcactcagt tgctcaggct   22440
ggagtacagt ggctcaatct tggctcactg caacctccac ctcctgggtt caagcaattc   22500
tcctgcctca gcctcccgag tagctgggat tacaggcgtg caccaccatg cccggctaat   22560
tttttgtatt tttagtagag atggggtttc accatgttgg ccaggctggt ctcaaattcc   22620
tgacctcaag tgatccaccc gcctcagcct cccaaagtgc cgggattaca ggtgtgagcc   22680
accatgccca gctattttta accattttttc agagcacaat tctgtggcaa taagcacatt  22740
catgttgtta tgtagccacc actgccgtcc atctccagaa cttctcctc tttcaaact     22800
gaaactctgt ccccatgaaa cactcactcc ctatccctct ccccagcccc tggcaccctc   22860
catcttgctt tctgcctcta tggatctgat gactctaggg acctcctagg agtgaatca    22920
cacagtgttt gtccttttgt atctgcttat ttcactgagc ataatatccc caaggttcat   22980
```

```
ccctgctgta gcctgagtca gaactgtttt cctttccatg gctgtatcac attcccttgt     23040
gtggatgaac cacgttgtgt ttattccttc atccatcgat ggacacttgg gttgcttcca     23100
gcttttgttt tgtttttttg tttgtttgtt tgttttttgtt agttcacgtc ttttgtgggt    23160
tttctttctt ttttgagatg gagtctcact ctgttgccct ggctggagtg cagtggcacg     23220
atctcggctc actgcaagct ccgcctcccg ggttcactcc attctcctgc ctcagcctcc     23280
cgagtagctg ggactatagg cgcccgccac catgcccagc taatttttttt gtatttttag    23340
tagagacggg gtttcaccat gttagccagg atggtctcga tctcctgacc ttgtgatccg     23400
cccgtctcgg cctcccaaag tgctgggatt acaggtgtaa gccactgcgc ctggccgtct     23460
tttgttaatt catacagtta tttgtcttct ggtttgttga agcagtaagt cagacaacat     23520
ttgccacaat aatgtctgtc aaagtggctt gccataaaca ctgcagcacc acattcatca     23580
gaagggcaac ctcgacgaag gtgactaatt ttgccattct catccacctt ataatatttc     23640
aggacagcca gcttcacctt ctttctcttg tgcttattcg tcttgcaggt aagacttctt     23700
cttctggccg ggctcagtgg ctcaggcctg taatcccagc actttgggag gccgaggcag     23760
gtggatcacg aggtcaggag ttcaagacca gcctggccaa catggtgaaa tcctgtctct     23820
actaaaaata caaaaattag ctgggcgtgg tggcacgtgc ctgtaatccc agctactcgg     23880
gaggctgagg caggagaatt gcttgaactg ggacccggga ggcagaggtt gcagtgagcc     23940
gagattgcac cactgcactc cagcctgagc tacagagcga gactccatct caaaaaaaat    24000
aaaaaaaaga cttcttcctt tccttagcac caccacgaat tctcaataca agatgaagag     24060
gagactccctt ttgaatgttg tagtcagaca gagtacgccc atcttccagt gcttgtcttt    24120
gctgatcagg aggaattctt tctttaccct ggatcttggc ctttacattt tctaccatat     24180
ctgagggttc agcctcgagg gtggtggtct tccctgtaag ggttttcagg aaaatctaca     24240
ttttggtggc ggctccacca cagatggcgg atctaaaagg ttttttgtttt ttgttttttt    24300
gagacagagt ttcgctcttg tcacccaggc tggagtgcaa gtggcacgat cttggctcac     24360
tgcaacctct gactcctggg tttaagtgat tatcctgcct cggcctccga gtagccagga    24420
ttacaggcat gtgccaccac cacacctggc taattttttt ttcttttgta tttttagtag     24480
agatggggtt ttgccatgtt ggccaggctg gtctcaaact cctgatctgg agtgatccgc     24540
ctgcctcggc ctcccaaagt cctgggatta caggtgtgag ccactgtgcc tggcctgctt    24600
ctgccttttg gctattgtga ataatgctgc tctgaacata gatgtgcaaa tatctgtttg     24660
cagctcctgc tttcaattct tctgggcgta tgtccaggag tagtgctgcc tgatcatatg     24720
gtaattctat gtttaacttt ttgaggcact gccaattttc acattttaa accatagga     24780
aaaaaagtt gttttttttt taaaaagac acagtctggc tctgttttcc acgctggagt      24840
gcaatggtgc aatcatagct cactgcagcc tcaaactcct gggctcaagc aatcccccc      24900
tcatcagcct cttgagtagg tgggactacg gcatgtgtca ccacacctaa ctaattttttt    24960
taatttttttt gtagaggtgg ggtctcactc tattgcccag gctggtctca aactcctggc     25020
ctcaaaagat cctgccacct tagcttccca aagcactgag attacaggca tgagccactg     25080
tgcctagcca aaaatatttt gtaatgttta gtgaaaatag aaatcatata aaattcaaat     25140
tcatataatt ttcataaaaa gtccataaag aaaattttct taaaacattg tcagctgggt     25200
gcggtggctc atgcctgtaa tcacagcact tgggaggct aaggcgggtg gatcacctga      25260
ggtcaggagt tcaagaccag cctggccaat gtggtgaaac cccatcacta cttacaatac     25320
```

-continued

```
aaaattagcc gggtgtggtg gcacgcgact gtaatcccag ctacttgaga ggccgaggca   25380
ggagaattgc ttgaacccgg gaggtggagg ttgcagtgag tcaagatggt gcccttgcac   25440
tccagcctgg caacaagag cgaaactctg tctcaaaaaa aaaaaaatt gccaagctca    25500 gtggcaggca cctgtcatcc tagctacttg agagaccaaa gcaggaggat tgtttgagcc   25560
caggagtttg agggcagcct gagcaacata gtgagatcct gtccctacaa acacacacac   25620
acagtttgct accccctttt ttttgagagg gagactcgct cttgtcaccc aggctggagt   25680
gcagtggcac gaccttggct caccgcaacc tctgcctccc gggttaaagc gattctcctg   25740
cctcagcctc ccgagtagct gggattatag gcaggtgcgc caccatgtcc ggctaatttt   25800 tgtatttta gtagagatgg gatttcgcca tgttagccag gctggcttcg atctcctgat    25860
ctcaagtgat ccgcccgcct tggcctccca gagtgctgag actataggca tgagccactg   25920
cacctggccc cattttttaa tatatcatca gtgactgcta tcacatgtcc atggcagagc   25980
tcagcagctg tagagtggtt ggacagtagg gcccccaaag ctgagaatgt ttactatctg   26040
actcgttaca gaaaacattt ttttgtaccc ctggtatgtg gtgatgagtg agaatgagac   26100
aactgtccat ggattacagc tacacccaac catgtggctg attctcacga acatatgtta   26160
gcatagaagc cagaccccaa aaagaacata ccatacaaat ccatttatta aaaaaaagg   26220 gggccgggcg cggtggctcc tgcctgtaat cccagcactt tgggaggcca aggcaggcgg   26280
atcacaaggt caggagatca agaccatcct ggctaacacg gtgaaacccc atctctacta   26340
aaaatccaaa aaaattagcc gggcgtggtg gcaggcacct gcagtcccag ctcctcggga   26400
ggctgaggca ggagaacggt gtgaacccgg gaggcggagc ttgcagtgag ccgagatggc   26460
gccactgcac tccagcctgg gcgacagagc aagactccgt ctcaaaaaaa aaaaaaata   26520 cctaaaaata caaaaattag ccaggtgtag cggcaggtgc ctgtaatccc agctactcgg   26580
gatgctgagg gaggagaatc gcttgaacca agaggtggag gttgcagtga gctgaaatca   26640
tgctactgca ctccagcctg gcaacagag agagactccg tctcacaata atgataataa   26700
taataaatga aatacaaaca aaactaattt atgctgtcgg aaatgacgat ggaagagtcc   26760
tggggaatca gagatagtgg tgataaaagc ataccaggaa ggcccctagt gagggggaa   26820 ttttgtaaaa gttttcagct gtaactctca tttgcacaat tttctctatg tatttatatt   26880
tcaatcaaca tgatgcatgt gtattaaagc cctgtgtaaa tgcaacggtg cacacaggtt   26940
caaagcgcag gcaatattta ttgagcaact attatgttcc atatgctgtg ttaaacacca   27000
tgcatacact aagaagcaga gggatgctgc ccttgcccgg gacgagttgg cccttgtcag   27060
tcagggaaag gcagacacca acagaacagc aataaaaagg ccgggcaatg gccaggcgc    27120 ggtggctcat gcttgtaatc ccagcctttt gggaggccga ggcgggtgga tcacctgagg   27180
tcgggagttc gagaccagcg tgaccaacat ggagaaaccc cttttctact aaaaacacaa   27240
aattagccag gcgtggtggc acaccaggtg ggtagctgta atcctagtta ctcgggaggc   27300
tgaggcagga gaattgcttg aacccgggag gcggaggttg tggtgagcca aggttgtgcc   27360
attgctttcc agcctgggca acaaaagca aaactccatc tcaaaaaaaa aaaaaaagt    27420 ccgggcgcca tggctcacac ctgtaatccc agtgctttag gagaccgagg tgggtggatc   27480
acttgagccc aggagttcaa gaccagcctg gccaacacag tgagaccctc cctctgtaca   27540
aaacgtaaga aaacattagg cagggatggt ggtggcttcc tgtagtccca gctactcagg   27600
aggctgagac agaagtaccg cttgagtcca ggagttggag actgcagtga gctatgatcg   27660
caccactgca ctccagcctg gacaacagag caagaccca tctctaaaaa aagaaaaca    27720
```

```
aaaaaacaac aacaaaaaac accaatagaa tgctcaatca gccatcagcc tcaaggaccc   27780
ttccatctcc caaggagagg aacccttttc cgtgagaacc tctgacctaa aaatcaaccc   27840
cacatggggg aatccagaaa gtattttggg gggaggaaaa gatgtttgaa gggagggtgg   27900
aggatgcaga agggttaacc aggagaggca gttagggagg gccttctggg tggagggaga   27960
ggactgcatg ttccaaggac ctgaggcaga atggagtgtg tgtatttaga ggaactgaaa   28020
gcaaatttgt gggacagggg atctagaggg gaaaagtgaa ttccacaggc tccctgtctc   28080
ttctggtcct agcaggaact ttcaagtccg ttttgtcca gatatttccc catgctcaag    28140
tcccagctca tcctgcctcc ttgaagacat gacttctgtc tcttcttgag ctactctttg   28200
acacaccctg gacaaagggt agcttgaaaa gagacagaaa ccatgttatt gccaggtgca   28260
gtggctcacg cctgtcatcc ttgtgctttg ggaggctgag gcaggaggat cgcttgaggc   28320
caggagcttg agaccagcct ggacaacata acaagacccc atctctacaa agataaaagg   28380 gaaaagccg ggcgcagtgg ttcacgcctg taatcccagc actttgggag gccaaggtgg    28440
gcagatcacc tgaggtcagg agttcgagac cagcctggcc aacatggcga accccgtctc   28500
ctactaaaaa tacaaaaatt agatgggcgt ggtggcgggc acctgtaatc ccagctactc   28560
gggaggctga ggcaggaaaa tcacttgaac ccaggaggtg gaggttgcag tgagctgaga   28620
ttgcaccact gcactccagc ctgggcgaca gagtgagcct ggtctcaat caatcaatca    28680 atcaatcaat ggaaaaaat tagctgggtg tggtggtcca tgctggtagt cccagctact    28740
gaggaggctg gggtgtgagg atcacttgag cccaggaagg ctgagactgc aatgagctat   28800
gatggcatca ctgcactcca gcctggacaa caaagcaaga tcccgtctca aaaaaaaga    28860 agaaaaagaa aaatcatttt tgagagctc tgattttcaa acctttgtt ctcagaactc     28920 ttcgggtaaa acctttttgaa cgacacaaaa ggagtgggca gctgtgatga cagattgagg   28980
agaaagcagg gtaggcatgg aacctctagg gttccctagg gacccagttt gaaaactctt   29040
ggttcagtag caggaaaagg caatatgccc cttaattctc ttctaaaaca taaaatcctt   29100
taacttcctc tgatttctac cagtaaaact gagctctact gacctcaatt ttgtaccaaa   29160
tgctatctaa taaaatccca gaaacagtga ttttgaaaa atccattttg ttgatgtgta    29220
atttacatac agtagaatgt gcctatctta tgtgtttggt ttcatgcatt gttttctttt   29280
ttcaactttt taaattttt tttttttttg agacagggtc tcactctgtt gcccaggttg    29340
gcgtgcagtg gcacaatctc ggctcactgc aaccttcgcc tctcgggttc aagcaattct   29400
cctgcctcag cctcctgagt aggtgggacc acaggcacgc gccactacac ccagctaatt   29460
tttgtatttt tagtagagac agggtttctc catgttggcc aggttggtct cgaactcttg   29520
acctcaagtg atccacccac ttcggcctcc caaagtgctg ggaccacagg cacacaccac   29580
cacgcccaac taattttgt atttttcata gagatgggt ttcaccatgt tgcccaggct    29640
ggtctcaaac tcctggcctc aagtgatctg cctgccttgg cctcccaaag tgctggaatt   29700
acaggcataa gccaccatgg ccagccctct ttatcaactt ttatttattt tttcatttt    29760 ttgagacgga gtctcgctct gttgcccaaa ctggagtgca gcggtgcgac tcagctcac    29820 tgcaacctcc gcctcccggg ttcaagcgat tctcctgcat cagcctccca agtagctggg   29880
attacaggtg cccgccacca cgcccatcta atttttgtat ttttagtgga gacggggttt   29940
caccatgttg cccaggctgg tctcgaactc ctggcctcaa agcgacctgc cgccttggc   30000 ctcccaaagt gctgggatta cagttgtgag ccgccgcgcc cgggaccctc tttatcaact   30060
```

```
tttatttttag attcagggga tacctgtgcc agtctcctac ctgagtatat tgcatgatgc   30120
tgaggtttgg ggtatgagcg actctgtcac ccagatggtg agcacagcac tcaacagtta   30180
gattttcaac cctcatgccc cttttcctca cccctccctg gcaatcccca ctgttcatta   30240
ttgccacctt tatgtccatg agtacctgaa gtttagatcc cacttataag tgagaacagg   30300
cagtctttgg tctgctgtta ctgagtttga tgcattttga caaatgtgtc tacctgcctg   30360
ctgcacgttt tggttttccc aagaattatt ttctaaaaat cagttttat taaggtggca   30420 tttatataca ctaaaattct gcacacgatc ttgtaaccat caccaccaaa tacgtattta   30480
tttatttatt attatttttt agagatggcg tctcactctg tctcgatctc ccacgccggg   30540
gtgcagtggt gccatcagag ctcactgcat cctccaactc ctgggctcaa gcgatcctcc   30600
tgcctcagcc tcctgagtag ctaggactac aggcacccac caccacccac agttaattga   30660
aaaaattgat tcttctttgt agagacaggg tctcatatgt tgccaggatc cttggtcttt   30720
gacctcccaa agtgcagaga ttacaggcat gcaccactaa tgccgggcca aatacttgta   30780
atttaaatta tcgctgggct gggcacggtg gctcacgcct gtaacccagc actttgggag   30840
gccgaggggg gaagttcacc tgaggtcagg agttccagac cagcctggcc aacatgctga   30900
aaccctgtct caactaaaaa tacaaaaatc agccggacat tgtggcagac gcctgtaatc   30960
ccagctaatc gggaggctaa gacaggagaa tcgcttgaac ccgggaggca gaggttgcag   31020
tgagccgaga tcgcaccatt gtgctccaac ctgggcaaca agagcgaaac tccatctcaa   31080
aaaataataa taaataaat tatagttgga aaaaaggggt ttcctaaaga cccaagggaa   31140
atggcctctt tgttcctgaa gccacagaga ggatttttct gctccccaca actagttttc   31200
cttgtgaaaa ttcataattg ctaccagctt gttctcctct ctgtcactat acatctgtcc   31260
ttgaagcctt atttgaacaa agagttctgg tatcactcgg atgcctagaa actgttgccg   31320
ttctgtgaaa ccgaccacca gaggaaaccc atgcttctca ttggctgcct tactaagatg   31380
gtgacttgtt gccctggtga caagttgcaa tgacaggtgg ctctgccaaa tcagaacaca   31440
gtgatacttg cttcccctcc cgggtgaagg atggaaaata aaagtaaaag ccttggcggc   31500
tgtcaggctt ctttaccaaa gagctggaga gcactccttg gccccattta tgcaaacact   31560
tcccatctac agatgatcca gcttcggagt gggagtctaa gcagctgcca ggaccaccgc   31620
ttggcagagg acaggctggg ggctctggca tgacctgctg gggccaggct gtgacttgga   31680
gcaagaggta gcaagaacct cgaggcagtg aacatcaaaa gagagatttc cggggctaaa   31740
caccctaggt ttttccttcc tcctgaaccc taaccctaac cctctcggct cactgcaacc   31800
tccacctccc gagtgcaagc aattctcatg cctcagcctc ccgagtagct gggatcacag   31860
gcgtgcgcca ccacgcccgg ctaactttgt atttttatta gagacggggg tttctccacg   31920
ttggtcaggc tggtgtcaaa ctctcgaact caggtgatct gcccgccttg gcctccaaaa   31980
gtgctgggat tacaggcgtg cgccaccgtg cccagcttat ttttgtattt ttagtagagg   32040
tggggtttca ccctgttggc caggctggtc ttgaactcct gaactcaagt gatctgcctg   32100
cctcagcctg ccaaaatgct ggggttacag gcgccaggcc aagtatctta ttttaaaagg   32160
ttacaaagaa tatagatgtg gataaaataa agtttctttt gcattaccac tttcctgcaa   32220
gaaatgaggg ggaggggctt atgaaacaac tcacaccccc ccaattgagg aactgtagat   32280
gaaagggaag gtgctgacag gcccgtctgg ccacggtttc ctggaataaa actgagccac   32340
acacctccac aaatcccag cctccggcaa gtacccaga agtactcaca ctccaccacc   32400
ttctgtgatc gcaacagccc tacgcaacat tacagagggc aaaacccacg ctggggaagg   32460
```

```
cggggctact gtcaaaaggt caccagggcc aggcacagtg gctcacgcct ataatcccag   32520
ctccttggga gaccaaggca ggaggatccg ttgagctcaa gagtttgagt tcagcctggg   32580
caacacagga aaaccccgt ctttacaaaa acttttaaa aattagctgg gtgtggtggc    32640
atgcccgtgt aatcccagcc actacttagg aggccgaagg gggaggatct attgcttcag   32700
cccgggagtt tgtggctgca gtgagctatg attgcaccac tgcactccag cctaagtgac   32760
agacagagac tcttaaaaaa aaaaaaaaa gggcagggca cggtggctta tgtctgtaat    32820
cctagcactt tgggaggccg aggcgggcag atcatctggc gtcaggagtt cgaggccaac   32880
ctggccaata tggtgaaacc ctgtctctac caaaagtaca aaacttagct gggtgtgatg   32940
gtgggcacct gtaatcccag ctactcggga ggctgaggtg ggagaatcgc ttgaatctgg   33000
gaggtggagt ttgcagtgag ccaagattgc gccactgcac tccagcctgg gtgacagaat   33060
gagactctgt ctcaaaaaaa aaaaaaaaa gtggggcacc tatattccca gcactttggg    33120
aagctgaggc aggaggatgg cttgaggcca aaaattcaaa acccggcctg gcaacatag    33180 caagacccca tctctatgaa aaaaaaaaa aaaagtcac caggccagct agcctagatt    33240
tcagagccag aatttgtctg atgccattgt ctttactttt tcttttcctt tttttttttt   33300
ttgagacaga gtctcactct gtcacccaag ctgcagggca gtgggacaat ctcagctcac   33360
tgcaacctct gcctcccagg ctcaagcgat tctcctgcct cagcctcctg agtagctggg   33420
attacagaca tccaccacca tttccagcta attttgtat ttttagtaga ggtgaggttt     33480 caccttttg gtcaggctgg tctccaactc ccaagctcag gtgatctgcc cacctcagcc    33540
tcccaaagtg ctgggattac agttgcgagc caccacgcct ggactgctct tcattctttt   33600
ttcagaactt tcccagctgc caacagagac agaaactgaa tcatctcaga agtgaatgaa   33660
ggaggctgag ggcgggtgga ctgcttgatt aggagttcga gatttgccta ggcaacatgg   33720
aaaaagcctg tctctgctaa aaatacaaaa attagccggg cgtggtggca catgcctgta   33780
atgccagctg cttgggaggc tgaggcagga gaatcacttg aacccgggag gcagaggctg   33840
cagcgagccg agatcgcgcc actgcactcc agcctaggta acagggcgag actccgcctc   33900
aaaaaaaaaa gaagggaatg aaggacaccc aaaatggagc ctctgtctgc cagggctttg   33960
ctatcctggc ctgcctatcc cagccctgga cacctcatct ctgatcccac cagagcggaa   34020
ccttcccatt cgcagggcca tttccttacc cagaaacctt ttcacaatgt tcttggcagc   34080
agctgttggt caactgtgtt ttaaggtttt tgagcaactt tacagaaaat aaaagggaag   34140
ctaccctcaa tgtctgggtc tccccctggg tggcctctct ttgtcacctt actcatttcc   34200
acgagatttc cttgcttcgt tgagttacat cacctccttt tcctgtctgg gtccaggacg   34260
cctcctctgc aggtctccag cactgattcc tttgtccccg atttctctgc tagggtcgct   34320
ggcttcacca tccaccacc actgctgctg gcccagcccg cagctttaat ttctctggac   34380
cctcacgttt ttgttatttg tgttttttt ggagatgagg tcttgctctg tcacccaggc    34440
tggagtgcag tggtgcaatc acagctcact gtagcctcca cctcccagac tcaagtgatc   34500
ttcctgcctc agcctcccaa gtagctgggt gtgtgccacc aggtgcagct acattttttg   34560
tagaggcagg ggtcttgcta tattgcccag gctggtctca aactcccagc tttagatgat   34620
cctttcacct cggcctccca gagtgctggg attaccagca tgagccactg cacccgtcct   34680
ctcatgtatt ttttattaat cgatttatct atttacttat tttgagacag agtcttgctg   34740
taccacccag gctggagtgc agtggcatga tctcggccca ctgcaacctc cactccctgg   34800
```

```
gttcaagtga ttctcctgcc tcagcctccc gagtagctgg gattacaggt gcccgccacc   34860
atgcctggct aattttttgta tttttagtag tgacgaggtt tcaccgtgtt ggccaggctg   34920
gtctcgaatt cctgacctca ggtgatccac ccaactcggc ctcccaaagt gctgggatta   34980
caggcgtgag ccaccgcact cggcctccct catgtatttt taagcggaac aggttcaaga   35040
tcacaaatgt tttcctctca ctctttcaat gagtttctat tctagaatct cctgcacgcc   35100
acaggaagga gaactctcac cctgtaatgc acataaatac atgagatcac cattgttctc   35160
acccagtaat cagaatcgtt agtgataatt agtaataaat ttattttttac tatatctaat   35220
aaattagata gtaattacta tggcagccaa tcgttcctgg gtgctcccta gatgcttcca   35280
agggagccac acgtgaccct cagggctgtg cccattccag gctcttctgc tgagctcatg   35340
taaccgcttg cctcaaggca ttccacaaat aatacataag tcaatgtatc acgttgtcac   35400
tttctgtaca aaccagctag ttccggaggg aagcagaaag ccttttttcag aagaaccaca   35460
gctaattcca gtagcaggaa tgataaagtt ggacataatc ctcaagagag taatgaatca   35520
aaaatggatg gcgggccagg cacggtggct gatgcctgta atcccagcac tttaggagga   35580
tgaggcaggt gaatcatttg aggtcaggag ttcaagacca gcttggccac catggtgaga   35640
ccccgtctct actaaaaata caaaaattag ccggcatgg tggctcatgc ttgtagtccc   35700
agcttcttgg gaggctgagg caggagaatt gattgaaccc tggaggtgga gattgcagtg   35760
agccaagatt gcatcactgc actccagcct gggcaacaag agcgaaactc tatctcaaaa   35820
acaaacaaac aaacaataac aacaacaaaa ttgatggctg ctaatgactt tttttctttt   35880
ctttcctttt ttattttttat tttttatgag acagggtctc actctatcgc ccaaactgga   35940
gtgcagtgcc gagatcataa ctcagtgcag cctcaacctc ttggactcaa gtgatcttcc   36000
cacctcagcc tcccatgtag ctgggactac aagcaattgc tgccacatct ggctaattat   36060
tttattttgt tgtatttttat ttatttattt tttgagacag agtcttactc tgtcacccag   36120
gctggagtgc aatggcatga tctcagctca ctgcaacctc cgcctcctgg attcaagtta   36180
ttctcctacc tcagcttcct gagtagctgg gataacaggt gtgcaccacc acgcctggtt   36240
aattttttggt tttttggtag agacgggggtt tcatcatgtt ggccaggctg gtcttgaact   36300
cctgacctca gtgatccgc ccatctcagc ctcccaaagt gctgggatta caggtatgag   36360
ccaccgtgcc cggtctttat tttatttttta gtagagacag ggttttgcta tgttgcccag   36420
gctggtctca aactcctggg cctaagtgat cctcctgcct tggcctccca aagtgctggg   36480
aactacaggc gtgagccact gggcccagct cctgttaaca tctttatgtg gagagttact   36540
ggggaccagg gacattcccc aaacccaccc atcaatcgta gtgacatgac gttatggacc   36600
ccctgatgtg atgtaccagg aagtacccgg ccctaccagc atgatattat tctggctgca   36660
actgacccctt attccaatag agcatgtggt tctaagccat ttatagggta aacattgggg   36720
cagggatggg gagagaggaa gcaacctgcc aaatccagaa tgaggatcat tcctcggtac   36780
cagaagagaa ccagaaagaa agcaccctaa gtggggatac cacaaggaag taaagcaggg   36840
gcctctccca gctggggaag ggaaggagga aggagtacaa tagcttgcaa ggcacagcat   36900
tgcggatgat gggaatagca ggtgcaaagg ttctgggca gggacagtgt ggtgtgtttg   36960
aagaacagca gccaggttca ccatgagatg ggaaatggac ttggggggaag ggatctcaaa   37020
ggataatttt tttttttttt ttgagacagg gtttcgctct tgttgcccag gctggagtgc   37080
agtggcatga tggctcactg caacctctgc cttccggttt caagcgattc tcctgcctca   37140
gcctcccgag tagctgggat tacaggcgcc caccaccacg cccggctaat ttttgtattt   37200
```

```
ttagtagaga cagggtttca ccatgttggc tagactggtc ttgaactcct gacctcgtga    37260
tccgcccgcc tcggcctccc aaagtgctgg gattacagac gtgagccacc gcgcccggcc    37320
ccccaacttt ttttttgttt ttaacacaac ttctcgcttt ctcacccagg ctggagggca    37380
gaggcacaat catagctcac tgcagcctcg aactcctagg ctccagcgat cctcacagga    37440
gggttttgag gatctgcata aagcgtgcag agggagcttg acttcgtgct cgttaggacc    37500
cgatattgtc agctgccgcc gcccacaggg acacataaat atttgtagac tcaatatttg    37560
cctttagtgt gaagacattg catcacctgg gtataagtaa ggagcagagg cagaggcggt    37620
ttaagcaaca gacttttgtc tccgctgaga accacggaat aaccccctgac ctacttcccc    37680 gtcgtgtcta attcgggtca cctcatctcc agttacagac gcggaagatc aaagaaaccg    37740
ggaaattgcg ccgcagcgcc ccctggcgtt cgcagcgcgt gcctacacaa gccactcccg    37800
gcgcaaaact gcggcttccc aggaaattga gtttaaatgt ttttttttct tttttcttaa    37860
tctagaaaag atcatttatt gtatcaagta actacccagt taggcgtgaa tacatttttaa    37920 aattttatt aaaacgagta ttggccgggc gcggtggctc actcctgtaa tcccagcact    37980 tgggaggcc aaggcaggtg gatcacggcg tcaggagttc gagaccatcc cggccaacat    38040
ggtgaaaccc cgtctctact aaaaatacaa aaattagctg ggcgtggtgg cacgcacctg    38100
tagtcccagc tactcgggag gctgagacag aagaatcggt tgaaccgggg aggcggaggt    38160
tgcagtgagc tgagatcatg ccactgcact ccagcctggg cgacggagcg agactccatc    38220
tccaaaaaat aaataaataa ataaatataa tataatataa aataaaataa aaagagtatt    38280
gtagagattg gctgggcaca gtggctcaca cctctaattc ctgcatttttg ggaggctgag    38340 gtgggaggtc ttcagcccag gagttagaga ccagcctggc caacatggca aaaccccatc    38400
tctactaaaa gtacaaaaat tcgctgggca tggtgtcgca cgtctgtgat cccagctttt    38460
tgggaggctg aggcaggaga atcgcttgaa cccaggaggc agaggttaca gtgaatcgag    38520
atcgcaccac tgcactccag cctgggcaac agagtgagac cttgtctcaa aaatacatat    38580
atttagg                                                             38587

<210> SEQ ID NO 4
<211> LENGTH: 30943
<212> TYPE: DNA
<213> ORGANISM: Homo sapiens

<400> SEQUENCE: 4
gggcgtggtg gcacatgcct gtaatgccag ctgcttggga ggctgaggca ggagaatcac      60
ttgaacccgg gaggcagagg ctgcagcgag ccgagatcgc gccactgcac tccagcctag     120
gtaacagggc gagactccgc ctcaaaaaaa aagaaggga atgaaggaca cccaaaatgg     180
agcctctgtc tgccagggct ttgctatcct ggcctgccta tcccagccct ggacacctca     240
tctctgatcc caccagagcg gaaccttccc attcgcaggg ccatttcctt acccagaaac     300
cttttcacaa tgttcttggc agcagctgtt ggtcaactgt gttttaaggt ttttgagcaa     360
ctttacagaa aataaaaggg aagctaccct caatgtctgg gtctcccct gggtggcctc     420 tctttgtcac cttactcatt tccacgagat ttccttgctt cgttgagtta catcacctcc     480
ttttcctgtc tgggtccagg acgcctcctc tgcaggtctc cagcactgat tcctttgtcc     540 ccgattctc tgctagggtc gctggcttca ccatccccacc accactgctg ctggcccagc     600
ccgcagcttt aatttctctg gaccctcacg ttttttgttat ttgtgttttt tttggagatg     660
```

-continued

```
aggtcttgct ctgtcaccca ggctggagtg cagtggtgca atcacagctc actgtagcct      720
ccacctccca gactcaagtg atcttcctgc ctcagcctcc caagtagctg ggtgtgtgcc      780
accaggtgca gctacatttt ttgtagaggc aggggtcttg ctatattgcc caggctggtc      840
tcaaactccc agctttagat gatcctttca cctcggcctc ccagagtgct gggattacca      900
gcatgagcca ctgcacccgt cctctcatgt attttttatt aatcgattta tctatttact      960
tattttgaga cagagtcttg ctgtaccacc caggctggag tgcagtggca tgatctcggc     1020
ccactgcaac ctccactccc tgggttcaag tgattctcct gcctcagcct cccgagtagc     1080
tgggattaca ggtgcccgcc accatgcctg gctaattttt gtattttttag tagtgacgag     1140 gtttcaccgt gttggccagg ctggtctcga attcctgacc tcaggtgatc cacccaactc     1200
ggcctcccaa agtgctggga ttacaggcgt gagccaccgc actcggcctc cctcatgtat     1260
ttttaagcgg aacaggttca agatcacaaa tgttttcctc tcactctttc aatgagtttc     1320
tattctagaa tctcctgcac gccacaggaa ggagaactct caccctgtaa tgcacataaa     1380
tacatgagat caccattgtt ctcacccagt aatcagaatc gttagtgata attagtaata     1440
aatttatttt tactatatct aataaattag atagtaatta ctatggcagc caatcgttcc     1500
tgggtgctcc ctagatgctt ccaagggagc cacacgtgac cctcagggct gtgcccattc     1560
caggctcttc tgctgagctc atgtaaccgc ttgcctcaag gcattccaca ataatacat     1620 aagtcaatgt atcacgttgt cactttctgt acaaaccagc tagttccgga gggaagcaga     1680
aagccttttt cagaagaacc acagctaatt ccagtagcag gaatgataaa gttggacata     1740
atcctcaaga gagtaatgaa tcaaaaatgg atggcgggcc aggcacggtg gctgatgcct     1800
gtaatcccag cactttagga ggatgaggca ggtgaatcat ttgaggtcag gagttcaaga     1860
ccagcttggc caccatggtg agaccccgtc tctactaaaa atacaaaaat tagcctggca     1920
tggtggctca tgcttgtagt cccagcttct tgggaggctg aggcaggaga attgattgaa     1980
ccctggaggt ggagattgca gtgagccaag attgcatcac tgcactccag cctgggcaac     2040
aagagcgaaa ctctatctca aaaacaaaca aacaaacaat aacaacaaca aaattgatgg     2100
ctgctaatga ctttttttct tttctttcct tttttatttt tatttttat gagacagggt     2160 ctcactctat cgcccaaact ggagtgcagt gccgagatca taactcagtg cagcctcaac     2220
ctcttggact caagtgatct tcccacctca gcctcccatg tagctgggac tacaagcaat     2280
tgctgccaca tctggctaat tattttattt tgttgtattt tatttattta ttttttgaga     2340
cagagtctta ctctgtcacc caggctggag tgcaatggca tgatctcagc tcactgcaac     2400
ctccgcctcc tggattcaag ttattctcct acctcagctt cctgagtagc tgggataaca     2460
ggtgtgcacc accacgcctg gttaattttt ggttttttgg tagagacggg gtttcatcat     2520
gttggccagg ctggtcttga actcctgacc tcaagtgatc cgcccatctc agcctcccaa     2580
agtgctggga ttacaggtat gagccaccgt gcccggtctt tattttattt ttagtagaga     2640
cagggttttg ctatgttgcc caggctggtc tcaaactcct gggcctaagt gatcctcctg     2700
ccttggcctc ccaaagtgct gggaactaca ggcgtgagcc actgggccca gctcctgtta     2760
acatctttat gtggagagtt actggggacc agggacattc cccaaaccca cccatcaatc     2820
gtagtgacat gacgttatgg accccctgat gtgatgtacc aggaagtacc cggccctacc     2880
agcatgatat tattctggct gcaactgacc cttattccaa tagagcatgt ggttctaagc     2940
catttatagg gtaaacattg gggcagggat ggggagagag gaagcaacct gccaaatcca     3000
gaatgaggat cattcctcgg taccagaaga gaaccagaaa gaaagcaccc taagtgggga     3060
```

```
taccacaagg aagtaaagca gggggcctctc ccagctgggg aagggaagga ggaaggagta   3120
caatagcttg caaggcacag cattgcggat gatgggaata gcaggtgcaa aggttctggg   3180
gcagggacag tgtggtgtgt ttgaagaaca gcagccaggt tcaccatgag atgggaaatg   3240
gacttggggg aagggatctc aaaggataat tttttttttt tttttgagac agggtttcgc   3300
tcttgttgcc caggctggag tgcagtggca tgatggctca ctgcaacctc tgccttccgg   3360
tttcaagcga ttctcctgcc tcagcctccc gagtagctgg gattacaggc gcccaccacc   3420
acgcccggct aattttttgta ttttttagtag agacagggtt tcaccatgtt ggctagactg   3480
gtcttgaact cctgacctcg tgatccgccc gcctcggcct cccaaagtgc tgggattaca   3540
gacgtgagcc accgcgcccg gccccccaac ttttttttttg ttttttaacac aacttctcgc   3600 tttctcaccc aggctggagg gcagaggcac aatcatagct cactgcagcc tcgaactcct   3660
aggctccagc gatcctcaca ggagggtttt gaggatctgc ataaagcgtg cagagggagc   3720
ttgacttcgt gctcgttagg acccgatatt gtcagctgcc gccgcccaca gggacacata   3780
aatatttgta gactcaatat ttgcctttag tgtgaagaca ttgcatcacc tgggtataag   3840
taaggagcag aggcagaggc ggtttaagca acagacttttt gtctccgctg agaaccacgg   3900 aataaccct gacctacttc cccgtcgtgt ctaattcggg tcacctcatc tccagttaca   3960
gacgcggaag atcaaagaaa ccgggaaatt gcgccgcagc gcccctggc gttcgcagcg   4020 cgtgcctaca caagccactc ccggcgcaaa actgcggctt cccaggaaat tgagtttaaa   4080
tgtttttttt tctttttttct taatctagaa aagatcattt attgtatcaa gtaactaccc   4140
agttaggcgt gaatacattt taaaattttt attaaaacga gtattggccg ggcgcggtgg   4200
ctcactcctg taatcccagc actttgggag gccaaggcag gtggatcacg cgtcaggag    4260 ttcgagacca tcccggccaa catggtgaaa ccccgtctct actaaaaata caaaaattag   4320
ctgggcgtgg tggcacgcac ctgtagtccc agctactcgg gaggctgaga cagaagaatc   4380
ggttgaaccg gggaggcgga ggttgcagtg agctgagatc atgccactgc actccagcct   4440
gggcgacgga gcgagactcc atctccaaaa aataaataaa taaataaata taaatataata   4500 taaaataaaa taaaaagagt attgtagaga ttggctgggc acagtggctc acacctctaa   4560
ttcctgcatt tgggaggct gaggtgggag gtcttcagcc caggagttag agaccagcct   4620
ggccaacatg gcaaaacccc atctctacta aaagtacaaa aattcgctgg gcatggtgtc   4680
gcacgtctgt gatcccagct ttttgggagg ctgaggcagg agaatcgctt gaacccagga   4740
ggcagaggtt acagtgaatc gagatcgcac cactgcactc cagcctgggc aacagagtga   4800
gaccttgtct caaaaataca tatatttagg aatttgctat gttgcccagg ctggcctcaa   4860
actcctggcc tcaagcaatc ctcccacctc gccctcccaa agtgctggga ttgcaggcgt   4920
gagccactgt gcccgacctt gagcttaagt tttaaacatt aaaaccacct ccctcccact   4980
ccctgcacct cccgtaagtt aaaacgcgtc cctgctgagg ccctgcaaag gcatatccag   5040
ggcaggcgga cccagggggt ccacagccga cccactttct tccccacacc tcatcccctt   5100
cacaactctc ctcatccatc tccctgccct ggtgggagat tccgataaat cctaattgtg   5160
gaactgctga atcagagggg gctgcatttt ccttagcccc cacctgcaaa ttgtgtgtgc   5220 agttttttctg ggatgagtgt ccttagattt ccctgaattc tcaaaaggat ctgtgacctc   5280
aaaatcagga gagaggccgg gcacggtggc tcacgcctgt catcccagta ctttgggagg   5340
ccgaggtggg cagatcgctt gagcccagga gaccagcctg gcaacatag ccagacccag   5400
```

```
tctctacaaa aaattaaaag attaactggg cttggtgatg tgcactcatg gtcccagcta   5460
ctcaggaggc tgaggtggga ggatcgcttg agcacaggcg gtaagagagg ctctacctct   5520
gaagaggatg cttccccacc ctctgccccc tccccaggca cccactccag cagtgagaat   5580
ttcactgcca acatgagaca tgggtcccta cctgtcccaa ctcagaccct gtctatgatg   5640
tcctatggcc tcagcaggga ccaaaaccct caccatggcc tcaccagaac ctccacgtgg   5700
ttctcagatt gggttgcagg tcagtaccct ccccctccagc tcctcagggg cctcctgcat   5760
tctctggcct tggcttctgc tctgccctcc cctcccttcc cttcgccccc ttcattttca   5820
ttctctatgc aaatgctgcc tcctctagga agccttccct gattgccccc agtctgggtg   5880
gattagatgt gatatgggct cccacagccc cttttgcctc agattactca tgtggctggc   5940
tgtatatctg tgcccagag aggtttcttt tccttttttct tttttttttt tttttttgag   6000
atagggtgtc accttgccac ccaggctgga gtgcagtggc atgatcatag ctcattgcag   6060
tctcaacctc ccgggctcaa gcaatccttc cacctgaaag tcctgagcag ctgggactac   6120
aggcgtgtgc catcacgtgc ctgactaatt tttcttattt tttgtagaga tggggtcttg   6180
ctatgttgcc caggctggtc ttaaactcct agcctcaagc gatctcccac ctcagtctcc   6240
tgagtaaact ggaccccagg tgcaagacac catgcccata aaaaatttt aaaaaattt    6300
aattttaaaa ttttttgta gagataggat cgtgttatgc cgcccaggct ggtctcaaac   6360
tcctgggccc aagcgatcct cccacctagg cctcccaaag cactgggatt acaggtgtaa   6420
gctacctcgc ccggcctctc ctgttctatt ggtgctgtga gattcacacc tcacttgagt   6480
gctatgggct gaactgtgtc ctctccacaa atgtctatgc tgaagtcctg ccccgcaact   6540
gcctcagaaa gtgactatac ttggagatag aatctttaaa gaataatta agtaaaaatg   6600
aggtcatatg cgtgggccct aatccaacat gaccagtttc cttgtaagaa gagcagatta   6660
ggacacagac atgcactggg gcgggggggag gagactgtgt gaacacacag ggaaaacaca   6720
gctgtctaca aggaaaggag agaagcttca gaaggagtca cacctgtgga catcttcatc   6780
ttggacttcc agtctctaga aacagaagac tataaatgtg tttgctttga dacagagtct   6840
tgctctgttg cccaggctgg agtgcaacgg tgcgatctca gctcactaca acctccgcct   6900
cccgaaggag gcgtagtgta attctcctgc ctcagcctcc caagtagctg gtaccacagg   6960
tgtccaccac cacacctggc taattttgt atttttagta gagacaaggt ttcaccatgt   7020
tggccaggct tgtcttgaac tcctgacctc aggtgatcca cctgcctcag cctctcaaag   7080
tgctgggatt atagttttgt ttttgagatg gaggtctcgc ttttgtcacc caaggctgga   7140
gtgcactggc acgtcttggg ctcactgcaa cctctgcctc ccaggctcaa atgatcctcc   7200
cacctcagcc tcctgagtag ctgggaccac ggtgcacacc actacattca gctaattcta   7260
ttttttgta gacacaggat ctcactatgt tgcccaggct agtcttgaac tcctggcctc   7320
aagtgatcaa cctgccttgg cctcccaatg tgcgactaca ggcatgagcc acggtgcctg   7380
gcaatttctg ttaagtcacc tagtctgtgg tactttgtta tgacagccct agcaaacaga   7440
tacacccacc gaaggccctg ataagtcctg cagtcaggag tctctgtgaa ccccgtgggg   7500
ctgggaggag aaagcaggga gcgtttgctg tgtgcctcac atgaatacag cagaagctga   7560
acacaactcc tggcatcgta tgcctacagg tcccccttgga acagttctag ggggggttgga   7620
gttccagggt ccattctgct taataacaat attaacggag cagccaaaat ggttccagtg   7680
aaaatggggt agcagcagct gtcatgcttg cacgccacca gccttcctgc gctatctctg   7740
ttctctcctc tgcaaagcag ctgctatttt gggctccctg ttttagatt gggaaccccg    7800
```

```
gaagttggtc agggcctcac cgctagaata tcttagagct gatattcaaa tgagagtcca   7860 atttttttt ttttgagacg gagtctcgct ttgttgccca ggttggagtg caaaggggca   7920
atctcggctc actgcagcct ccacatcctg ggttcaagtg attctcctgc ctcagcctcc   7980
caagtagctg ggactacagg tgcacaccac cacacccagc tagttgtttt gtatttctag   8040
tagagatggg ttttcaccat gttggccagg ctggtcttga agtcctgacc tcaagtgatc   8100
ctcccgcctt ggcctcccaa agtgctggga ttacaggcgt gagccaccgt gccctgccaa   8160
aagtccaagt tcttaacctc catgagggct gagatgccc tcaggggcag ggagaggcta   8220
attctccttc tgagaggata taggggttg gtggggcctg gggcacaggc ctggctcagc   8280
acaactccca gggactccct tgataagaag gtgaggtagg cactggctgg cagagcgacg   8340
ggaagagttt atttctctgg aaagggaggg gtaggggcg gggccagggg tcagggcagg   8400
gcaatgtcct ccagcttctt gtccagtgcc ttcaggtcat ccaggaagcg ggtcggggtg   8460
aggatgtgtg aggagcctgt gcaggggcag aggtttgggg aagatgttgg ggggcgctgc   8520
cttcgtcttt gacaggctcc cggtcccggc tggtgtgggg ctgtccctgt ccctcagcaa   8580
accaggtccc tgactccaag gactctggag tccagacacc tagaaggtac aagcccaggc   8640
cccgggaacc caagccccag accccagggt cccagtcctg gtgacttacc aatgagcacc   8700
tcccacttgc cctcggtggc cctggtcacc tcgtaggcgg ccctcatctc tgacatggcc   8760
acaccgccca tgacatacac gatgagccgg gggcccgccc gggcttctat gccagccttg   8820
ttcttgtgcc agtgaccgaa gcgggcactg tgcaggggcag gggcagaaag tccaggcagg   8880
aggccctcac cgccgccagg ccgcccacct aacacagacc caggcgtggg cggggcggc   8940 cccgggcct cacctgacag cggcctggga gctggccgtg gggcggggt cggatacgaa   9000 gggccacagg ttcctgtcca gccggtcctc cacggcgtcc tggcggccga gaggcaggtt   9060
aggggaggaa ccccaggcat ggggtccggg gtcaggagtg cccccacgg ggtattcagg   9120 ggccaagatc ctggcagaca ggaaccagca tctccacctc ctgcctctgg gggacccagg   9180
agtctaggcc tctagtccat tggggaccta gaaatctaga tccataactc actggggacc   9240
cacgaatcta attccataac tccttgggta cccagaagtc taaacccaca gttcctcggc   9300
aacccagtag tctgggcctc caggcccttg ggaccatca gtcaataccc ccagcccttt   9360
ggggaaccca gtgtctgggc tctcagcccc tcagagcccc agaagtccag gtattcaagg   9420
tccatgggga tgaggaggcc caggtctctg gcccccacgc agaaagaggg gccggggctc   9480
ttagagggac aaggaggaag ccaggaagcc gccccaggcc cattgccatt ggatggtgct   9540
gccctgggat cctgggaagg ccagggctgg ggctcagggg cactcctgcg gacaggggaa   9600
acagactaga gagatatagc ggaggcagcc ggcaggtggg gaggaagtga ggctccccag   9660
cacaggcccc gctgtcaccc caattcctca gctgcgggct tggcgtgccc ccctcagcag   9720
agcagatcgg tgccaaggga atgccagcaa tgagcatttt cccctaagcc ctgaggctta   9780
gcacctcagc aggagggagg ctgagccgcc agccgatgcg gagggctggc ccccacccctg   9840 acctgccacc cagtacctcc attacatcct tgatgaccgg ggtccagcgg gacagctgat   9900
aggtgggctc catgcgttct ctcggctcca gccggctgga ggtccccgag ccctacaggg   9960
agggcaggga gggcagcagg gggattgagg ggaaggaggc tggtcacaga ggggctgcgc   10020
ctggtgtggc tggtagggtg ggggatggca ggcaaagatg gggaagtgga acagagagcg   10080
agagagagcg agagacagca agaaagcgag agagagaaac agtgagccag agagagacgg   10140
```

```
agagagaaag ccaaagggag agagagcgag ccagagaaag acaaagacag aggcagagat   10200
aggcaaagag ataagaagca gtgagacaaa gtatgaaggc aaagagagag acaagagatg   10260
aagcaggaaa cagagagagg aagatgggga cagaaggggg acggagaggg gaggggagca   10320
agacagagaa cagagagaaa ggggaaggca gagagaaggg tgagagagag agatatggag   10380
aaacagtgca cagcgagatg gatgaggat ggggagaga tggggacggg gtgagggcac     10440
cctggagggg gacgcacagg gccagagaga gacaggagag gctgacccaa gagtcaagca   10500
cacacatggc tgtgtgtggg tgctggatgg gtgcggggga ccctcagaga cccctgggag   10560
cccagataga caatgtggtg tagccccat gctggggacc ctactccctg cctctagcac    10620
tcagaccacc cgctcccaac tgcaccactg ccaggaccag cctggcagcg accatgtctc   10680
acttcccctg cctattgtgt aagctgggac tgggagaggc cccagtgtcc tctgggcccc   10740
agaccagacc cgaaacactg cttttggcct cccagcaacc acaccacgcc aggaaccaca   10800
ccgtgcctgt gcaccaatgg ccctctgcct tgcagagccc cggctgtgat ccgcacccctc  10860
tcccagggtc cccccatgcc cgctcctggc gtaccccggg gttggtgaca gtgcctccca   10920
gctgctccag gttacggatg aggctgctgt gcgcctgtac attggcatgc tggatcagct   10980
tggccaggtt ctcctcactc acacctgggg gacgggaatg ggcagggtgg aggcggcggc   11040
caggtgagct cccaggttta ggggagtttg ggtgggctg aggagctccc aggactctga    11100
tgagagaacc ttgcagtggg gagggcctca gtaccctgtg ctagtgtgag caagagtggg   11160
aaacctggag gggtagatc aggggctcct ccagatgagc tgagggagcc ccacatctat    11220
aggaatcaca gatgtgaggg tttctacgtt agcagggagc cctcacctca gtggaggaat   11280
ccccaagcca atggaggagg gttcccgggt ccagaggggt agctgtgggg gttggtgagc   11340
ccggtgagtg caaatgaccc aaggagagct gtggggttca gcagttccca ggatcgtggg   11400
agacgctggc aaatggggac gttccaactc cctgcagccc ccaccacca ttccgaagga    11460
ggatgtagag cagcaggacc cggatcttgt cgtaggcggg caccgccgcg tccagcagca   11520
ccggaacgat cagcttcatg gagtccttga tcttctcccc ctctgcgtcg agcccatgg    11580
ccaggtcctg cgggcatggg gtcagccgtc caccggccgc tatgtgtcag ggaagggggat  11640
gggagaggcg ggccaaggac atccccagga tcctcggcaa gaggacattt gggtcctacc   11700
tcatctcagc accaggtctc tcaaggtccc accctgtcc agggacagtc tctccacagg    11760
ccctgctcct cacccaggtc ccacctttcc agtgccccac ccactacac acaggtcaca    11820
ccactatcct gagactacct ctccaaggct ccaccctca cccaggtccc agctctccaa    11880
ggctccaccc ctcacccagg tcccagctct ccgaggctcc accctcacc caggtcccac    11940
ctctccgagg ttccacccct cacccaggtc ccacctctcc gaggtccac acctcaccca    12000
ggtcccacct ctccgaggct ccaccccta cccaggtccc acctctccaa ggctccaccc    12060
ctcacccaag tccacctct ccaaggctcc accctcacc caggtcccag ctctccaagg    12120
ctccacccct cacccaggtc ccacctctcc aaggctccac ccctcaccca ggtcccacct   12180
ctccgaggtt ccacccctca cccaggtccc acctctccaa ggcccgtgc ctcacccaga    12240
tcccacctct ccatggctct acctgtctcc cagctcctac ctctccaagg cccacccct    12300
cactcaggtc ccacctctcc aaggctccgc ccctctccca ggtcccacct ctcttaaggc   12360
tccacccctc tccaggtcc caccctcca aggttccacc cctcatccag gtcccacctc    12420
tccaaggttc caccctcac ccaggtccca cctctccaag gctccgcccc tcacccaggt    12480
cccacctctc caaggctccg ccctctccc agggcccacc tctccaaggc tccattcctc    12540
```

```
tcccaggtcc cacctctcca aggctctgcc cctcacccag gtcccacctc tccaaggctc   12600
cattcctctc ccaggtcgca cctctccaag gccctgccta cctctccaag gtcccaccca   12660
cctatgaata ggccacattc ctgtcctggg accacctgtc caaggctctg cccctcaccc   12720
aagtctgacc tctccaagcc ccatccacct atgcacaggc cacaccctca tcctaggacc   12780
gtttctccac aagacccact ccttccccac caggtcccac ctctctccaa ggcccctcca   12840
cctctccaca gccctgccc ctcccccaga acccccatc tctacagttc agcccctccc   12900
caataccccg ccttggcagg accatcaccc ctgcccccg caagccctgc ccacctgct   12960
ccacactaca cagcttctcc accgagccct tgaagtgctt catacaatca tctgctagat   13020
gcaggtgcgt agaatactgc agggtgcagg gtggggttg ggggataaca aaggctgagt   13080
caaggcagaa cgcagacaga gcatggggtt gaggggccga ggtgtcccg ctccctgccc   13140
acccgagcac accttattca gctccttctg gtactgcggc atctttttca ggatctggga   13200
taggtctttg atgttcgcct ggggaagtag ggggaagagg gtagggattg gggggcgaag   13260
ccaggcagtg cccacctggg tctcagtcca ggctcgaaat ccaggctgtg gccctgcgcc   13320
catggggagg ggggcttcct tccaccagcg cctttggtga cctgggtccg ccctacctt   13380
gtccgtggtc agcctcttgc tctcacagaa ggtcctcagg agtccgtga ccttcctggc   13440
catgagggtg ggcgggggtg agagtgaggg gagaggagcc acaggccatg ggtgagccca   13500
ctcagggggg acaggagag gtggggtgaa attggaggcc agtctggagt cacacgaggg   13560
gtgctcatga gggccaaaga cttggcagca gccaggatc ccaaggccgc taccaggccc   13620
acagtgggcg gtggggggg gatccggtcc ccgtgtgcac gcacttggac acatctgcga   13680
tatgcatgtg gcgaagctcc acccacaagt catcgtcctc gtccagcaag acggccttct   13740
cccgcgcctc gctcagcccg gtggtctcat acctggggag gaaggaggga gcctggggt   13800
caggggagct gaggactggg gaaccaggtc agtggcaagg gtggggacgg gttccaagtc   13860
tgcagacctg tatgtgtcct gctctatgtc cagcagatca tacgccatgg cctggaacgt   13920
gagctcatgc agtagtgggg acacggggtc agctgcccgg tccattatca gcagctggga   13980
gcgggttttc tctgggccct ggggtggggt ttagggcagg aatgaggcac tgaccctgag   14040
ccggttgggg ctgcccctca cctcccaagc acgcccctc acctcgccca gactgggagt   14100
gtctgccttg aaggcgttca gcttggccag gacggcgtgg gccaactggg ctgtgtcctc   14160
tgggcccctg gcggggaggt cagacacggg ggacatcatc aggggatggg gtcaaggatg   14220
ggtttgaagg tgagagtcag gggccagggt agggccgggg ctggggtcac aagagaggtt   14280
aaaggttagg tgttgcacgc ggttaagggg ggtcggcat cggggtgggg ctgggtgggg   14340
tccccacttg cggtagcgga tggccgggta ctcctgcagg gtggcgcaca gcgtggcaat   14400
ctgctgggcc agcacctcga gctgccgcgt gcgctcctct gcccggaagg ggcagtagag   14460
gttgtaggtg ctgtggggag catcgaggga gaacacctgg gcgaggaggg gacagaagca   14520
ccagggttgc cgctgcaggt gcacacctgc cccgcttccc gctgccgcca cctgcacctc   14580
ctgggagccg tccctggtcc ctgaagcctg ctttgccgaa ttggaggcag gcccaggtca   14640
accctaaacc catgcctgca ggagtcagtg gataaatacc ccagcccgtg tcccttaagc   14700
tggctggaca acccgcggt gcgctctacg ctgcccctg caagggccta gtgggataga   14760
actcaaggca agagtccctt ggactctgtg gtgacctccc cttttaaaa ttttactttta   14820
tgtatgttttt tgagacagga tctcgctctg tcgcccaggc tggagggcag cagtgcaatc   14880
```

```
atagctcact gcagcctcga cctcccgggc tcaagcgact ctcccacccc agccccatga   14940
gtagctagga ctacaggtgc acgccaccac gccaagctaa tttctttctt tttcttttt    15000
taagagacgg ggtcttgctc tgtacccagg ctggtctcaa actcctggcc ccaagtgatc   15060
ctcctgccct ggcctcccac agcgctggga ttacaggtat gagccactgc gcccagcctc   15120
agtgtctgtt tctgagggaa caggggacat ttggtcacaa accccacccc cctgcccagg   15180
atgagcccgg gccgtacctg ggcctcgtag gggaggaagg caaggtgaat ctccttcaac   15240
gtcttcacca cctttgccag acgagagcgg cctagctcac tgaacagggg ctcggggcag   15300
gctggggtga ggcaggagtg gggcatcagg ccagagcagc ccccacacct ccttgcccca   15360
cccaccaaca ccctaggctc tcctcactca ctgtcggtga agaagatatg ggccgctttg   15420
taggtgaaag tcgggtccc ctggaagtct ttgatcaggg cctgaaccga ctggggaagg    15480
tggatcactc tctgggcctg agcctgcaca cctaggctca ttggctgcct aggcctccca   15540
gccaccccc atctgccacc atgtgcaaac atggacggac gggacatgt atatgtgcaa    15600
atgcacacta gtgtcgcacc cacatgggca cacgcgcaca cacacagatg cacgcacgca   15660
cacacacata cacacgcatg cacacatgca cacacacaca gatgcacaca cacatacaca   15720
catgcacaca cagagatgca cacacataca tacacacatg cacacacaca gatgcgcgcg   15780
cacacataca tacacacata tacacacatg cagacactga tgcgcacaca cacgcataca   15840
cacatgcaca gacgcataca cacgcata cacacgcaca cacagatgca cacacataca    15900
tagacacatg cacacagatg cacatacata tacgcata cacacatgca cacacagata    15960
cacacagacg cacacacaga cgcagacaca tacatacaca cgcatacaca catgcacaca   16020
gacagacgca cacacacaca tacagatgca cacagatgca cacacacata catacacacg   16080
catacacaca tgcacagaca caaatgcaca cacagaccca cagacacaca cgcatacaca   16140
catacacaca aatgcacaca cagacgcaca cacatgcaca tgcacacaga cacatacata   16200
gacacacatg caaacacgca cacacatgca tacacagatg cacacacaca tgcacacaca   16260
tgcacacaca tacacatgga cacatgcaca cgtatacaca tgcacacatg caatcacatg   16320
catgcagaca tacacacaca tgcacatgta cacgcatgca cgcgcataca cacacgctca   16380
ctcatgtagg caccttctcc gtggggctca gcaaataaat ggcctccaga ctgggaatgg   16440
gttcccgccg tttgttgatg tcttcaacaa ctagtaggaa cagaggaagg gacacaggtg   16500
ggtggcatcc aggcagggcc acgtggggag tctcaggtgt ggggggttgg aggcttgggg   16560
aggaggggtg gatgcttagg agggactgca ggagaaaccc acttagggac caccagctaa   16620
gagccacacg acagggttct gcaggggttg tgcagccaac tgggttcccc aaatttacag   16680
acagggagac tgaggttctg agaggacagg ctccctcagc acctatccct caatggcaaa   16740
gtgactggga caccacctgg ggtcacccat agaaggctct gcattcttgg gaccccacat   16800
ccagagtcca ccctgggagt cccacacagg gctccacgag ggagctgcac ggtcaggaag   16860
gggctgcagc cagggagtgc tgcaggggag gcctgcaatc catgggctcc cgcagtcagc   16920
ttgcaaggtt taagaatgga tttggtcaca tgatccgggc tgtccgtgca gggagctgcg   16980
tacttgggag ttctggacga tttgagggga tcctacactc aagggctgaa ccctgggaga   17040
ggggcacagt caggggttcc cacgctcagg tcccatctca ctggggacgc gttcactcac   17100
tggtgatgcc ctcagccagg atatctgaca ttttgcagca ggaagacaag atgcgcatgc   17160
ttgggtgatc catgataagc acctgtccag atggatggac agatggatgg aggagcaggc   17220
ggaagaggcc acagctggcc ccagaagggg ccaaggcagt gggaggggca gtttcaaggg   17280
```

```
ctggctgggt gggaggaccc agaacccatt cacccaactc cacccatgtg gacaggcagt    17340
tcttgggggt cccacattca gggtcttccc cataggcctg atgatgagct gcctctgggt    17400
acccagccat ctgcctcacc cctaccttcc actccccatc cttcttgaca ctccgaataa    17460
ctccgctcag aatttctgca gggaagggag gggagggtc agaatgctgg ttctctggtc     17520
ccaccactgc cccaagcctt ctcagccttg gggctgaacc cccatcttaa ttcccattta    17580 ctttttttt tttttaaga gaggaggatc tcactctgtc acctaggcta aagtgcagtg      17640
gtgtgatcat aactcactgc ggcctccaac tcctgggctc cagcgatcct cttgcctcag    17700
cctcccgagt agctgggact acaggtgcat gtaccaccca cagctaattt attttattt    17760 ctgtatagat ggggtctcgc tatgttgccc aagctggtct caaacttttg gcctcaagca    17820
gtcctcctgc ctcggcctcc caaagtgctg ggattacagg tgtgagacac ggcacaggaa    17880
tcatttattt ttagccccca gttctgcaaa ttggcttctg gggtcacccc caatttacag    17940
acagggaaac agattcttag gcaacatgta actcacctac gcatcctgag tgtctaagtg    18000
gcagagtgct ggggcaaaag gtgccactcg ataaacatgt tttaggtgaa tgaaaagagg    18060
agaaccggga tcatctacag ctctatctgc ctctagcgcc aggctctcgg cttccccacc    18120
tgctacctca gtattcctg ctgtgagggt ttcagccagt ccccccaacc tggtctaaaa     18180
tgtaggaccc ctggttccca gctctgaggc atgcctagct gaggctatcc cactgacctc    18240
cggtctcagt ttcctcatct gtaaaatgga atcacttttt tctaatctcc cccaattaaa    18300
ggggtttgag ctacagaccg ccctgcctag aggagagagt ggagagaagt aacggggtgg    18360
ccccgcccag ccacgtccac tgtgtcatgt ccactgttat caagacggcc agggcggaag    18420
gagcagctga ggccggaact ccccggggtg gaggaagagg cgccctccac ccttccccca    18480
agaaccgggg ccggtgaggc ctggacgcct gcgtcctcca gctgcaaggc gctcctggaa    18540
atggggcaag gaggaagaca tcccctacac caccccgtgtg gggcctggac acgtcccctg   18600
agcgctcaca gcacctaggg tcgctgacca gagccctagg aggccccaag aatccagccc    18660
ctgaactttg cccggcttaa gagatcctag agtgtgggca tccagctgtg ccctcctccc    18720
ccggcaggca cctaggagg cccaggagtc cgggcccag cctccgccac actctacccg      18780
tcccctttgg gtccccggag tccggccccc caatttttgtt ctgttctggc accggagagc   18840
aggggcgtcc agctgggaac ccgtccccgc ccgccccctc gagggtcagg tgctcggacg    18900
cccagcccgg cccccaactc ccagccgcca tgaaacccag gatcccagag cccgtgcgtc    18960
cccgaccccc gtcccacacc ggacgccaga gccggccccc ggagaggcac tcactttccc    19020
ccaccaccgc cttcagcccc gagggcgcca tcttccccga ggggcgccgc cgccgcttcc    19080
gggtgtgtcc caaggtgggg gcgtggccgc gcgtcaccca cgtggacccc ccccgcgcc    19140 ctgtccccgc cccctgcgca cctggcccct cccgccgtc ggttctcgcc caggcccagg     19200
aagttgagtc cctggcgggg aggacgggca ggtgcgtccg cgctgccgag cacgaagtcg    19260
ctggaggtgc acacctcgac gacacgctca cagatgggag ttcagacaca cacttcctgg    19320
cttgcgtgcg aagcaggatc gcagggcaat aatccctcca tcttcccccgg gaggttctgt   19380 gcctgcaaga tacacggcac ccactcgatg ccacccgggcc gccactgtct gggcctggga   19440
tcttgaccca cttgccttct gtacttcagg gtttagaggc agcagcagca gcagcagccg    19500
tcttggataa ctttttgatgg attcaggagg cctggagacc tcttgtgtgc aggcacctgg   19560
acataatttt cattcagtcc tgcccaatgt tccgacctgg actgcggtgc cgacgaggaa    19620
```

```
accgaggctt agcgggatcc ctaatccaag gccacgacga gtgagcctgc tgggttcaag   19680
ccaggagcct gtccccaggg ggcatttgtc acagccttac cctcttccgg gagggcgcaa   19740
cgcttaccct cgtggaccaa caatcgaatt aacatgctga tacacacatg gggtgagtga   19800
cgccctcaaa tgcttgcaaa cacagacaca cactcggaat tcagaagct gcttctgctg    19860 tgtgtcctgt cgcttggaag gcacagcccc agcagcaccc atacaaaatg aggtctccga   19920
tttaaggtgc gaggtatgtg tgcaaacaga ctcttgctgg tctgagctgg ttccttcgct   19980
cggccgtgtt gatgaaggta ccaagccccc tgccacttac atgggacata gggagtgaat   20040
cagacccgaa ggtctggggg agataggaaa ggatccatgc tgccctaaag gaaataaact   20100
aatgtgacaa caagtgccac agaaggtagg ggtgggaggg gactttactg aggatgaccc   20160
ccgagggcct ctctgaagaa gcagcctttt gacattatcc ctaaatggat tctagaagca   20220
gccacacagc atgtccaggt agagaaggga ggagccccga gcttaagaag gctggagggt   20280 ggggggcagca ggggccagac ttctgtagga caaggtcaga ctgacccatc ccagtgccag   20340
gatgcaggac tttcagtgct aaaaatagga cagtcacagg caaaccagga cggttggcaa   20400
ccgtaggtag gagtttgagc tatttcttcc tttcctttcc ttttcccttc ctttcttcct   20460
tcttctccct cctccccatt tttgtttgtt tttgttttgt aaagagacgg tctcgctct   20520 gttgctcagg ctgagggca gtggcacgat catagctcac tgcagcctcg acttcctgag   20580
ctcaagggat tcttccactt cggccaccca agtagctggg actacaggtg cacgccaccg   20640
tgcccggttg atttttgttgt tgttgttaag agacaggatc tccctatgtt gcccaggctg   20700
gtatcaaact cctgggctca aggatcctc ctgccttggc ctcccaaagt gttaggattt    20760
taggtatgag ccaccgcacg ctgccccttc tccttttgt aacagcttta ctgagatata    20820
attcacatac catacaactc gctgacctaa ggtgcgtaag tcaatggctt tcagtatttt   20880
tggagttgtg tgtccattac cacaatccat tttagaacat ttccacaacc ctaggtgtt    20940 tgggttttgt cttctcaaga gttttgagca ggggaaggcg gggaaccctc cagatcctgg   21000
ggggatggaa gccaggaccg cctccagctt ctcagcctga cccccttgggg ggacagagag  21060 ctgttagggc cagccacccc accactaacc cccaaaagat atgaagtact aatccccaat   21120
accccacaat aggatcttat ttgaaatggg gttagtatag atattagcag tgagcatgag   21180
gtcacactgg agtagagtag gcccctaatg caatatcact ggtgtccttg taagatagtt   21240
atatgtctgc ctggttctgt gtaggtggtt ggggggggtgg ggaaatgggt atatgaagac  21300
tgggacacag agggagaatg ccatgtgacc acggaggcag ggagtgaaga gctgcagtga   21360
caagccaagg acatcaagga cggcaggcca ctgccaaaag ccaggagggg gcaaggaggg   21420
ctcctgagac ctggttttca gagggagcac agctctgcca acaccttcat ttcaggctgt   21480
ggcctctgga acgttggctc aataaatttg ttaaaaaaaa attttaaagg ctcagcatgg   21540
tggctcatgc ctgtaatccc agcactttgg gaggcccagg caggaggatc acatgaaccc   21600
aggagtttga gactagcctg ggcaaaatag tgagacctca tctctatata aaaatatata   21660
acaaaagtca acttatgtgt tttaagccat ctggtctatg acactttgtt ctggcaggcc   21720
taggaaaggg atacacgtac tgaggagggg gacacttcat tggcatagag ggagagagtg   21780
tgaacttggc cttttgtgga acagaggagg ctcgggcaga ggtggtgata gtgcagccca   21840
ttcattctga gatgaaactt ccactggttt ccgtaaaggc gtcttgggga gggaagggaa   21900
ggggatgggg acctcccagt ggtatcccct gcttgggcac tgaggaaaag ccacagtggc   21960
tcgggggaaa aggcagggac gtcctctccc cgcctgcctc tgtccccagg gagtctcgcc   22020
```

-continued

```
tcctgttccc acctggggct agggtgatag aggagaggag atagctcaac ctggcattta    22080
ggtggtgtgg gaacaggaga ccccagactt tcttgttttg gggtctgggg caggcaacca    22140
ggctccaggg acagtgagtt gaaggaaggg tggctgggag accccttgac ttgctgccaa    22200
ggagacagag ctggagctag ggtggccggt ggtgtctgag gcaggtgcag agagggaggg    22260
agggaagggg cctttgactc caacctcctt tttctgtacc gactgcaggt ggcagctgcc    22320
ctttcaggag ccagtggggg aacctgggtg gctgggtggg gacacctgca agtcctccct    22380
aagccagcta ccaccctaca ctgttggcct cccttctcca actgtgggga tgctgctcag    22440
gcctttgtg acatcacacc tgagagtccc tggggtccag tcattgctgc tgggcacagc    22500
gaggtccaag ctcaggtcgc cctgccccct acccaccatg ccagatccag catcgttgtg    22560
ggcaaacaat tatctggatg atctttatgg ggcttaagct tgggtgggag cagatggggc    22620
atgagctggg gatttgggga tgggggggaat ccacacccccc acgtcctgga cgtttaaaag    22680
gccctctctg gcactgggcc ggggcagagg ccagcagaaa agtgactgga gtccagggac    22740
atgatggatc aggaggagaa gacggaggaa ggctcaggcc cctgtgccga ggtgagaggg    22800
ccctgccccc accccacccc cagctcaagg tctcagagcc catgattgac aagactagtt    22860
tgtaggcac ctaattaacg agtgagtctc ctaggacccc ctgacccagt tgtggctgta    22920
gaaaggggct ggtgggcttg ggggtctgag tgccaggccc cagggcagag ggcagggctc    22980
tccgtgtgga cccctattga tgggagatgc tgggacctgg gggtagctcc tgggccatgt    23040
ttccctgatt cgtgtcccag ctcccaggcc acactcatca ggcccaatc taggacggcg    23100
ggacacgcat cggagcctgt ccctttgaagc ggtaccacgt gaagtggcac tgctggccag    23160
ggcccctggg gcggggccg ggattgggaa ggagactcat gtctcattca gaacagctct    23220
gcagagagga tcggcgggga ccatggtgag agctgaggaa gtggggacgg caggccccgg    23280
ggtcagggtg tgagcaagct ggctaggaag tttggggagg gccccaag ctgaagggcc    23340
aaccagactg agcgagtctg tccccaggcg ggctccccag accaggaggg cttcttcaat    23400
ctgctgagcc acgtgcaggg cgaccggatg gagggacagc gctgttcact gcaagccggg    23460
ccgggccaga ccaccaagag ccgtgagcat gggcacgggg gtgctgtcca tggggcgtga    23520
acggggtggg agtgcagggc aagtggtcat ctggagggcc tggggggcacg ggatgtggga    23580
ggtggttgtg caccctgaag catctgtgtg ggggtgaagg ggtagggttg ggggccccca    23640
ctccggctgt gtcctcccaa gtctgtgaac gtccacgcag agagcgaccc cacccccgag    23700
atggacagcc tcatggacat gctggccagt acccagggcc gccgcatgga tgaccaacgt    23760
gtgacagtca gcacgctgcc cgcttccagc ccgtggggtc caaggtaggt gatgttctgg    23820
cgatgtcgag gagaaacccg ccaggcagtg ctctccgatc ctgccctcca ccccagccag    23880
gagggaacag ggcctgcccc atctctgtcc atccgctgcc ctgacttcag atgggaggac    23940
caaggcccag gcagtggcta gaggggccca aggttataca ggggccatgc tagtgtaaga    24000
cccatggctg gaacttgtgg ctcctgcccc caagtctgaa ggttctgggg aggccaaagg    24060
gagaaaatag gaccccttcc taggaaagta tcccagggag gaagtcacgt aagctcacac    24120
ataggatata tacatctgta tactcacatc tgttgacttc acacatacac gaagcttggg    24180
ttctgatcaa gatcccagcg agggcccaa gacctgccac ctcacactca aatgccaccc    24240
taaatgcag atattgaggg taaacataga ccagtgctca caatgaggtg ggacacggtg    24300
gctacctgca ccctctctcc attgttcgcc acctgtggcc ggcactgccc ttgagccctc    24360
```

```
cccctggctg acccctcttc atccacagga cggagcacag aaacgagctg ggaccctcag   24420
tccccaaccc ctgctcaccc ctcaggaccc gaccgctctc ggcttccgtc ggaacagcag   24480
cccccagccc ccgacacaag ccccctgagg gcctgaggca tcctgggtct cactcggccc   24540
ccaaaaactg ataaaagaat aaaacactta aatgaataac aaggaactga gtatatgtat   24600
atttcatcag gggaggggct aggactccca cttggaggcc tcaggagttc tgctgggcgt   24660
cgcgaaggag cttctcctcc cgccgcttcc gtaacctctc tttgaattcc tctatctctt   24720
gaagctaggg gtggagaagc gggtgggaca ggaaggggggg aggggcacac acctcagagc   24780
cgggaccccc ccccccgcc cacctctccc accaccctgc cccagaccac ggcttcaggg   24840
ttcagtgtct tcactggaag ccccctgcca attacaaagg ggtccgcgtg ggatccgctt   24900
cactcttcca ggagaaggca ataaggaaac catctactcc tctgctctcg gttccttact   24960
catggctgag agtaaaatgt ttcttttga gacaaagtct cactctattg cccaggctgg   25020
agtgcagtgg cgtgatcttg gctcactgc aacctccacc tcctgggttc aagtgattct   25080
tctccctcag cctcccaagc agctggaatt ataggcgcct gccaccatgc ctggctaagt   25140
tttgtatttc tgtagacatg gggtttcgcc atgttggcca ggctggtttt gaactcctga   25200
cctcaagtga tctacccacc tcagcctccc atgccctggg attacaagca tgagccactg   25260
cgcctggcct aaaattttca tctaaaaccc atcccggata caagaatcca gcctcctcca   25320
tccctctggc aggaagaaga gatcacttac cttctcaggt ggccacagct ccctctgtaa   25380
ggaaaagtca caaatgggac acgagccaaa ggcctccaga gccccacatc agggcagggt   25440
cggcttatgg gaggcagaca ttagtcccca gcagactgct gccccacacc ctctcccacc   25500
cctggaatga accctcaaac actcctctta tgcccacctt gcgctgtatg acatcgtcct   25560
caaaccactc ggcctgattg gaaacccaga acatagccac agggaaagtg aggtagatta   25620
tcatctggaa tggcagaggg tgggtgaggt gagctccccc caagcaatgt gcagaggctc   25680
ctcagagcct gggggaccca tcctactgca gagtccagaa gcgcctcgtt acggccgacc   25740
caagaatccc agaactccca ccaagggtac agaaacctcg caccctaaaa cctaactcct   25800
ataatccagg aggcctcatt cctgaaagtt ccctctgagc tggagtcttc ctctcaaaca   25860
cagacagaca cacagacgcc ccagctacaa tcaaaagcat ctcctcgaga cctcattacc   25920
catccccact taagatcccg ggagcacccc caaacccagg aggcgtcact cttcaactcc   25980
acttctcgaa gtctaggaat ctccctgtca tagacaccca cccaccacga gcccgagagc   26040
tccccaggga tcttaagtct tccttcttta gagccccctt ctcagctcac ccctctctga   26100
ggtccttcct cggaccagcc ctctcacagc ccccaaaatc agaagcacaa atccgagaac   26160
ccccccagcc cagcgtcccc tctcctggat ttccaaccag aaaggtcctc tcaaatctta   26220
agagctttct ccttggagct ccctcttcct ttgaagtccc cccatttcca acctcatctt   26280
cagatccagg aagatcccct gcccagcctc ccaacccact cctgtgtcca ctgacccgaa   26340
atatctccag cttcaccccc atctcgtttc tcccggtcaa caaagccagt tccgcccaaa   26400
gccgaccctc cagcaagaca gaagctcact ggtgttttgc acgctccatt gctgaagctg   26460
attggccaat gtgtatcctc atggcgcatc ttctggcgcc tctattctgc ttccggtcgc   26520
tggcgtcgtc gaaaagaagt caataacgtg ggcctgtccg tcaaaaatga tttaaccaat   26580
agaaaacggg tctggctcgg aggggcgggc cgtcagtggt agacgtcata agcgcgcgac   26640
tctctcctgt acctgggcat ccagaaaaat ggtggtgatg gcgcgactct cgcggcccga   26700
gcggccggac cttgtcttcg tgagtccaca gaggagccgg gggtggcctg cgttggggca   26760
```

-continued

```
ttgggacctg gacgccgcag gggatcgagg ctgggtcggc aaggagattt aggccgaaac   26820
tgccaggcca aggtctggga accctaatgg gccagagacc ggatcgtcat gtccgcaccg   26880
aactgtccag gagtaaaaat atggtgttgt atcttcgggt ctgagtagaa aaccactgtc   26940
gaagggaagc gtctagcctc ccgaaccagg ggcggaaatg ggggcgtgca gggaatggga   27000
gaggaggaag atcgcataac tgaaccttga gaggtgaaga tcgtgtctg aagtaaaggc    27060 ttgcttacga ggccagggtt ctggtttctg ggatgaaggc ttggttttct ggatagcggt   27120
ctctaggcct ggactgcagc atgacagttt ctggggtggt ggccaggcta aagaaccct    27180 ggtgatgtgg agcttgtcag gcgatggcca gtgaaatact tactctctgg agtagaggcg   27240
tgacatcttc accagattct tggtgtgcag agttaaaggc ttggcttctg gtgtataact   27300
cctcctgtga gataaaggcc tagcttttaa tttctggggc agagttgagc tagacgctgg   27360
ctagtgggat cctgggggcg gggctagtgg cttggaatct ggacctgaga gccctggtgg   27420
ctggggtaaa gatctggtca tctgggcctg gggtggagat gggtcagatg gtgacagtgg   27480
gagtctgagg ggcaaaggcc tggtgtctgg gaagaggcac gttttgaaga agtgggggtct  27540 ggtgtccagg actggcatct gggccagggc cttggtatct aaggagtctg accatctggg   27600
gcagaaagcg agtggtgatg cggactcatt cctggcccag agccctaatg actgagaagt   27660
ctgatgattt gggttcgatt ttgggtagtt gaattctgag gggtaaaggt ctgggccact   27720
gtcttggtgt cggcatctg gtttggtgcc tgggcatctg gtgacctgac ttccttggtg    27780
ggtggtggga tctaggtaaa agtccggagt ttggacctga gccccagcag tgggatggtg   27840
ctgcacacag gctctgaggg taggcctctc ttcttcccat tccctggccc tgcaggagg    27900 aagaggacct cccctatgag gaggaaatca tgcggaacca attctctgtc aaatgctggc   27960
ttcgctacat cgagttcaaa cagggcgccc cgaagcccag gctcaatcag ctatacgagc   28020
gggcactcaa gctgctgccc tgcaggtggg aatggctcca gctgccctgc ccaccagccc   28080
ccaccccacc tggtccagtt ataacaaaac tgccaagtgg gtcccgggtc ccgggtgatt   28140
gcttcgtgtt tcatcactga cctgtacatc ccttgatggg tcagcacacc ttctctgatg   28200
tcccagtctg tccctgtcat tgctgagaca tgtcacccct cccacacccc ttcttcccac   28260
atttgccaac tggggcaggg caaatggttc tgggggtgtc cataaagctg accgatcagc   28320
atctgtcccc tcctattccc cagctacaaa ctctggtacc gatacctgaa ggcgcgtcgg   28380
gcacaggtga agcatcgctg tgtgaccgac cctgcctatg aagatgtcaa caactgtcat   28440
gagagggcct ttgtgttcat gcacaaggtt tggggctcgg cgagggatg aatcgggaag    28500 tggagctcag tccatggtgg tgggtggggc gggacaggg gctgggctca gcatgttagg    28560
gatgggggct tggattcctg ttgcttcttt gcatgggaag ttgggctgga ctcagtcctg   28620
gagctggggg tttctgggtc ccgccgcatt tatgtggtgg ccccaggtgt ggctcagcca   28680
caggacatcg agtgtctgtg gccaggcat ggagtccgtg gcttagcccc agccgcctct    28740
ccccacaccc ccagatgcct cgtctgtggc tagattactg ccagttcctc atggaccagg   28800
ggcgcgtcac acacacccgc cgcaccttcg accgtgccct ccgggcactg cccatcacgc   28860
agcactctcg aatttggccc ctgtatctgc gcttcctgcg ctcacaccca ctgcctgaga   28920
cagctgtgcg aggctatcgg cgcttcctca aggtgagcct agcaggtgcg ctggttcccc   28980
aggttagttt ccagaaacgg cctcactgtg acactagctc cgtgtaggat gtcacccagc   29040
agacgggatg tgggaagagg ctcctggaga tgcatgtgtt ttgttgttgt ccgtgattca   29100
```

```
tgtctttatt ttccaaatag tttgttcaca ctggtttcac attaggcata gcgatgggtg   29160
ctgaggacag tgtgactaag acactccctg cctgcacgga gcttttagtc taactaggaa   29220
gacagatgca tatgagctga tggcatgaac tagagtaaaa ccacagccat gaagagggcc   29280
aggaataagg gtggggagaa gcaggcaggg tggagagtgg aagcaccagc cgggcgggag   29340
tggggcatgg tttgctcaaa cttaaagtat ctgttttatg acgtttggat tctaagctgg   29400
accagtcagg actgaggctg gacccgtggg gcccaggctg gacactatag tcaaggctgg   29460
acccatggga tcaaggctga cccaaggggg ccaaggctag accagtcagg actgaggctg   29520
gactagtgga gccaaggctg gacccattgt gggttggggg tcaattctaa cccaaaagga   29580
ccaaggctgg accattgggg ctgagactgg accaccgcag tcaaggctgt gcccttgcgg   29640
gtcaaggcta acccaaaaag tccacagctg gtctagtcag gactgaggct ggaccagtgg   29700
agccaaggca ggacccacag ggggttgagc ctaacccagt ggggccaagg ctagaccagt   29760
aggaaccggg ctggaccagt ggggctgagg ctggtttgac agggcttgct tttgcccaag   29820
acactcataa atgggtgggg ggggacgccc cgaagccact gaatcgggag gtgggcgtag   29880
ccctgccacc ccactgactg cctgaggggt ggctcggtcc ccagctgagt cctgagagtg   29940
cagaggagta cattgagtac ctcaagtcaa gtgaccggct ggatgaggcc gcccagcgcc   30000
tggccaccgt ggtgaacgac gagcgtttcg tgtctaaggc cggcaagtcc aactaccagg   30060
tgggcctgcc gggagccggc aactgggtgg gagggccacc ccctccatga ctgagcctga   30120
gactctcccc cactgcccca tgccctgcag ctgtggcacg agctgtgcga cctcatctcc   30180
cagaatccgg acaaggtaca gtccctcaat gtggacgcca tcatccgcgg gggcctcacc   30240
cgcttcaccg accagctggg caagctctgg tgttctctcg ccgactacta catccgcagc   30300
ggccatttcg agaaggtgca tgctggcaca cggggctctg ggttcggggc ggggtctccc   30360
tccgacactc ggggacacat gttgacacat gcacagacag aaaacatgcc atttatggct   30420
gggtgtggtg gctcacacct gtcatcccag cactttggga ggccgaggcg gtaggatcac   30480
ttgaggtcag cagttcaaga ccagcctggc caacatggtg aaaccccatc actactaaaa   30540
atacaaaaat tagtcagaca tggtggtgcg cgcctgtaat cccagctact cgggaggctg   30600
aggcaggaga atcgcttgaa cttgggaggt ggaggttgcc gtgagctgcg atcgcgccac   30660
ggaagtccag cctgggtggc agagcgagac tccatctcaa aaaaaaaaaa aaaaaaaaa   30720 agtgccattt ttgacagaca tgcatatccc tgcacgcgat tactatcctg ctgagggtgg   30780
gggagcactc ctgcccgcaa gcacgtcagc cttttggagtt cagccacatt ttgcgttcag   30840
ggtttcaccc tcttggctct gcggcctttg ccccaactaa gggtggtttg ttcttttcatt   30900 tgtaaaaatc agggtgacag tttactgcct tgtcaccaat cag                    30943
```

<210> SEQ ID NO 5
<211> LENGTH: 64700
<212> TYPE: DNA
<213> ORGANISM: Homo sapiens

<400> SEQUENCE: 5

```
gtgcctctag aggatcccca tgcacagatt agaaggtgag tcttggccgg gcagggtggg   60
ctcgtgcctg tcatcccagc gctgtaggac gccgaggtgg gtggatcacc tgccaggagt   120
ttaagaccat cctggtcaac atggcgaaac ccctctctac taaaaataca gaaattagcc   180
agtcatgatg gcgggcgcct gtaatcccag ctatttgaga ggctgaggtg ggagaatcac   240
ttgaacccag gaggcggagg ttgcagtgag ctgagatcgc gcactgcact ccagcctggg   300
```

-continued

```
cgacagagtg attctgtctc aacaaaataa ataaataaac aaacaaacaa ataaataagg    360
gtgagtcttg ggctgcaggg tatggggcac caaaatgagg taccggtccc caggcacaga    420
ctcaggatgg ggaacctggg gtgagaaggg agggtgcaga ctcagagggc tgccgggaac    480
tgggctcctt ctccccgccc catccctga cccaaagcct tttgctccag caactgggct     540
ccaggggagc ccaccagccg gagccagggc gaggactgcg tgatgatgcg gggctccggt    600
cgctggaacg acgccttctg cgaccgtaag ctgggcgcct gggtgtgcga ccggctggcc    660
acatgcacgc cgccagccag cgaaggttcc gcggagtcca tgggacctga ttcaagacca    720
gaccctgacg gccgcctgcc cacccctct gcccctctcc actcttgagc atggatacag     780
ccaggcccag agcaagaccc tgaagacccc caaccacggc ctaaaagcct ctttgtggct    840
gaaaggtccc tgtgacattt tctgccaccc aaacggaggc agctgacaca tctcccgctc    900
ctctatggcc ctgccttccc aggagtacac cccaacagca ccctctccag atgggagtgc    960
ccccaacagc accctctcca gatgagagta caccccaaca gcacctctc cagatgagag    1020
tacaccccaa cagcaccctc tccagatgag agtacacccc aacagcaccc tctccagatg   1080
cagcccatc tcctcagcac cccaggacct gagtatcccc agctcaggtg gtgagtcctc    1140
ctgtccagcc tgcatcaata aaatgggca gtgatggcct cccacatttg tcccttctt     1200
ggaggcctgg ctgggtctgg tctctgggtg tggcacatgg gagctgggaa ttccagagtc   1260
tgatgcctga ccacctttt gaaagttggg acatcagatc tttggccggg tgtggtggcc    1320
catgcctgta attccagcac tttgggaagt caaggcaggc gaatcatctg aggtcaggag   1380
ttcaagacca gcctggccaa catggcaaaa ccccgtctct attaaaaata caaaaattca   1440
gccgggcacg gtggctcacg cctgtaatcc cagcactttg ggaggccaag gcaggcggat   1500
cacaaggtca ggagatcgag accatcctgg ctaacacggt gaaactccgt ctctactaaa   1560
aatacaaaaa attagccggg cgtggcgcg tgtgcctgta gtcccagctg ctggggaggc    1620
tgaggcagga gaatggcgtg aacccgggag gtggagcttg cagtgagccg agattgcgcc   1680
actgcactcc agcctgggcg acagagcgag actccatctc aaaaaaaaaa aaaaacaaa    1740
aacacaaaaa ttcgctgggc gtggtggtgc acacccgtaa tcctagctac tcaggaggct   1800
gaggcaggag aagtgcttga acctgggagg tggaggttgc aatgatctga gatcacgcca   1860
ctgtgacaga gcgagacccc aactaaataa atttaaaaag aaagaaagaa aattgggagc   1920
aagcagatgt ggtggctcat gcctgtaatc ccagcacttt gggaggctga attgagccga   1980
tcacttgaga ccaggagttc gagaccagcc tggccaacat agtgaaaccc cgtctctact   2040
aaaaaaaaaa tacaaaaatt agccaggcac ggtggcatgt gcctataatc ccagctactc   2100
gggaggctga ggcaggagaa tcacttgaac ctgggaggca gaggttgcag tgagccagga   2160
tcgtgctact gcactccagc ctgggtaaca gagtgagatt gcatgtcaaa aaaaaaaaa    2220
agaagaaaaa agaaacaaat tgaggagcaa ctgaagtaga attcgatctc ccgttttat    2280
tttttcctgc tctatgacac ggagaatgtg caggacatga agcctctgag gtccaatggc   2340
cccttggaat actgtagggg aaggcggtgg atcaccctga ggccgggagg gcgtgagttg   2400
actcatggaa gtacccagag cagggcttag tacacagaag gcactcagta agtgctggct   2460
ggctggacag gctgatgggg agtgggcccg gtcaaccgga ggccatttcg ggtctggagg   2520
tgttaaccct actcagggtc tgggaggctg aggtggcacc agcctcacgc tcggccaagg   2580
tcgacccatg ccggaggcca cgggagggag gccaggagca cagggtcccc tctccacact   2640
```

```
cctctaccag tggctcaggc caacactggg gtcattgcac ctcttccctt tcccctgaca   2700
acacctccag gtccaagacc ataagaaatg ccagtgcggg ctgctgtcaa acggcgctca   2760
caatcactca ctgctcaccc cttctgccac tgcctcgact ggagcagtca cctccgcccg   2820
gggctctctc ttcactgccc cctttccaga agtttcctcc agctcagata aaaggccaaa   2880
gccagctgcg cacagtggct catgcctgtc atcccagcgc tttgggaggc tgaggtggga   2940
ggactgcttg agttcaggag tttgaggcca gcctgggcaa catagtgagg ccccatctct   3000
acaaaaaata caaaaactag aggtgtagtg atgggcaact tggtcccagc tgcttgggag   3060
gccgaggtgg gaggattgtg ccctgctct cagcctgggc gacagtgaga acctgtctca   3120
aaaaaaaaga agaagaaaag agaaaaagcc agccaggtgc ggtggctcac gcctgtaatc   3180
ctagcacttt gggaggccaa ggcgggcaga tcacttgagg tcaggagttc cagaccagcc   3240
tggccaacat ggtgaaaccc cgtctccact aaaaatacaa aaattagctg ggtgtggtgg   3300
cggatgccta tagtcccaac tattcaggag gctgaagcag gagaattgct tgaacccagg   3360
aggctgagat ctgagatcgc accactgcac tccagcctgg gcgacagagt gagactccat   3420
ctctaaataa taataataat aataattaat ctgtgtgacc atgggcacat gacttctttt   3480
ggaacctgcc tgtgaaatga gctgatgctg cttgcccagc tcaccaaggg ctggtgcctg   3540
gctcctcctc ctcctcttcc tctcacccac ccacctggag ggtccagggg aagaccttcc   3600
ttgcagccca gagcaccgta agttagagct gctgtgatca aagctgccg aaccacaggc   3660 tcttctttct cttcatcctc ccttgcccca accccgggcc cagcctcata accctacagc   3720
ttgttcaaac gttttcccttt ctcctcaagc cccctaactc accctcggtg gccggtgggg   3780
atggggcgtg ggaacagacc ctgggccctg cactcccagc ttacaaattc ccgcagcccc   3840
tcttcctccc tcccgatttc tctgacatcc ctcacagccc cgcctctgga cagaagaatg   3900 gccctgccc tggccggccc tggaagcccc tctcgccagg gtctcagagg acctgcctgg   3960
ggctgcttag cccaaagcgt cctgcatttt gctctgaaat ccagcttctc agacaccatg   4020
ttcccctccc tccgtccccc atccaggact gtggtttctg tgtctgtgca gacgcccaga   4080
cctccctcca gaactccaga ccccaaaccc caagacctgt gcatctgctg gcccccctaga   4140 cgcctccccc tcattccaga ttcaggctat catcctgccc aagccctctc ccggcgcctc   4200
cctccacctc caacagccaa cagctattcc aggatcagcc ctggggctat gtgtggtggt   4260
tgctcaatgg tttcattcat cctagagacg ccaccttctc cccagtgtgc tgaagcccac   4320
cctgctcaat gcctcttgct aggatggctg agactgccct gaccaagccc tcagccctgg   4380
tccaccaggc agtccaacag agcatcctaa acaaatctag aggtgacacc gaccccttg   4440 gcccttctca taaccagtga ggggagccca gctgacagtc cctgcagttc cttttctgaa   4500
cagacctgtc tgttcacatt ctgggggggcg gtggaaagga agcagggaag attggatcat   4560
ggttccccca aaaatctgg aagaactttc cttggggag aggaggagtt atcaggaacc   4620
aagtgtggtg aacaaaaagg gaaaggaaaa ttgcctgagg tgtaatacat tactttttttt   4680 ttcttttta agacagggtc tcactctgtt gctcaggctg gagtgccagt ggtgtgatct   4740
tggctcactt caacctccgc ctcccaggtt taagtgatcc tcctgcctta gcctcccaag   4800
tagctgggat tacaggtgcc tgccaccacg cccagctaat ttttgtattt ttagtaaaga   4860
tgggttttgc catgttgacc aggttggtct caaacttccg gcctcaagtg atctgcccac   4920
ctcggcctct caaagtgctg ggattacaga cataagtcgc cacgcctggc cttatttcaa   4980 attctttttag acaaggtctc actatgttgc ccaggctgga caccaacccc tggcctcaag   5040
```

```
cgatccttct gcctcggcct cctgaatagc tgggactcca ggtgtgcacc actgcacccc    5100
acttatttta aaatttttt aacaagggaa atgtgtttgt atcatcctgg actttaaaat     5160
taactttaaa gtattgacca gactggccaa cacagtgaaa cctcatctct actaaaaata    5220
caaaaaatta ggtagctggg actacaggaa tgcacctcca tgcccagcta attttttgtat  5280 ttttagtaga cagggtttt caccatattg gccaggctgg ctcgaactcc tgacctcgtg    5340
atccgcctgc ctcggcctcc caaagtgctg ggattatagg cgtgagccac cgcgcctgac   5400 cttttttgttt tttagatgga gtttcgctct tgttgcccag gctggagtgc aatggtgcaa  5460
tctcggctca ctgcaacctc cacctcccgg gttggagcga ttctcctgcc tcagcctccc   5520
aagtagctgg gattacaggc atgtgccacc acacccggct aatgttttct attttttagta  5580 gagacggggt tttgccatgt tagccaggct ggtctcgaac tcctgacttc aggtgatcca   5640
cctgcctcag cctcccaaag tgctgggatt acaggcgtga ccaccgcac gtggcccctc    5700 ctggtgattc tgatacccta agcctgcat ctcaatctaa ggtccccagg aatcccctgg    5760
gggcctcgct aaaatgcacc ctcagattca gcagctctgg ggtgggcctg agactgcatt   5820
atggaccaac tcccagttga tgctgctact gctgatctac agaacacact ttgatttggc   5880
tcacgcctgt aacccagca cttacggagg ccaaggtgga aggattgctt gaggccaaga    5940
gtttgagacc agcctgggca acctaataag agccccatc tctacaaaaa ttttttaaaa    6000
attagctggg catggctggg cgccatggct cacgcctgta atcccagcac tttgggaagc   6060
cgaggtgggc agatcacgag gtgaggagat cgagaccatc ctggctaaca tggtgaaacc   6120
ccgtctctac taaaaatacg aaaaattagc caggtgtggt ggtgggcacc tgtagttcca   6180
gctactcggg aggctgggc aggagaatga catgaacccg ggaggcggag cttgcagtga    6240
gccgaagccg agatgctgcc actgcactcc agcctgggcg acagaacaaa accctgtctc   6300 tgaaaatat aataaatgag ggaagaaggc aaacaatctc cctctgcctg ttttctaggc    6360
acacggtgac acccactcct ttacatgttg tctgtggttg cattcagtac atcagcggag   6420
taatggggca agagcacatg gcggcacagc agtggctcac gcctgtaatc ccagcacttt   6480
gggaggctga agtgggcgga tcacctgaga tgaggagttc gagaccagcc tgaccaacat   6540
ggtgaaaccc catctctact aaaaatacaa aaattagccg ggtgtggtgg aggcacctg    6600 taatcccagc tacttgggaa gctgaggcag gagaatcacg tgaacccaag gtggaggttt   6660
gcagtgaggt gagatggtgc cactgcactc cagcctgggc gacagagcaa gactctatct   6720
caacaaataa aaaaataat aataaagacc acatggcata aaatattgcc catctggcac    6780
tttgcgcagt ttgcccaccc ccagtctaaa ggcgtctgtc tcagcctgat gcgtctccca   6840
ggaccccatg cccctccag cctgcagaca gcctccaacc gtgattccag aacctgccag    6900
catttcccac caactccttt tgccgggttt atttctcccc accactcctg gtctcactca   6960 acccccaac cctatggcca gacccgcccc cactctactg taaacacatt cggacctggc    7020
ctccctcccc agcctgggc agggctgtgg ctcaaggtac tgagtggatc taaggccgcc   7080
acacaagaca caagacacac gtggggaggg gctctctgta tcctttatct ccggcagggt   7140
cagcggccct ccagggcccg gtctcgagcg atgactgcct cctcgaactt gatcatgagc   7200
gtggtgccct tgtgccagtg cgccgtgacc ttggcaggga agccgctgtg tgtgagcacc   7260
gcctccacga tgcccgccgt gaagctggcg cagttgagcg tgctgttctc cttgggcacg   7320
gagatgtagg tgttgatgag cggctcgcgc tcgatgatgt agaaggtgcg cgcgtcatcg   7380
```

```
ttggcctgct ccagcttgtc cgcctccttg ccgaagagcg ccttccacac ggcgcccttg    7440
acgaagagca acgcgcctag caccttggtc tcacgccggg cacccttttc gcgcgccacc    7500
agcgcatcca gcacgcgcgc gcccacctgg cggcccagcg cggccaggcg cgactgcagc    7560
tcggccacgg agaagacgcg gctctggcag tgctgtacca gctcggagaa cagcagtgcg    7620
aaggcgctca ggctcacctc ggtgcgcggc gcgccagcg cgcgctccag cagcgccgac     7680
ttcccgcgcg tgaagcgcgc ctccatgccg ccgccaccct gcggggagac caggaagtgc    7740
aggtgtcagg ggcaatggga aggggagcag gccgggagga aaggagggag aaccgcgagg    7800
ggccctggga cacccctcgac ccatgccact gttgtgtgct ccagtgccga cttcccactt   7860
gcaaagagat gcgcgtaaaa cacgcctcga ttacacgtaa ccagataaat caagggaggg    7920
gggagtctta taccctcggc aggcagcggg ctagcgggag tggggacaag gtgggaggag    7980
agacacgagg gggaacagaa gaggaggccg aaaccaccca accctcgggc atgcagacgg    8040
ttcaattgcg aaagcgcctt cctgcccgct ccgccaccta caggagtaac tagaaaacta    8100
gtgtatgggg ggaggggcgt cagatctagg gcagggaggt gacaaagatg aggcaccacg    8160
aggggatatg ggcagtcgct cctgcccgc cctgcgctcc agcacagacg accctcggga     8220
actttcctgc cggccccctg cggaaagcca gagtaaaggg ggtggagggt gggagtgggg    8280
taggagcgtg tcaagaccaa aagccaggag ggttgggggc tttaacaggg gggatccgtg    8340
gggccaggca ggaggggcgg gtaaccccca accccaagcc ctcaggcagg cagctccgat    8400
gtgtcacgca ggaacccttc gtcctttgag acgcggatgg gcctgggttc tgaaggctgg    8460
gaggaggggc ccagaggtgt tgggagcctc ccacccccgt gctctccaga aaggaagctg    8520
gatgctgagc aactgtggtc ctcccatcag ctgtcggtgc ggggagaggg agatggggta    8580
gggggctcct gaagagaaat ggggtgggga gcgggcgccg agacgggatc ggaggggcag    8640
ctgagaaccc gccccacca tgcatgggga ggtgtgtgga tgctaagccg accccaacga    8700
ggtctgcgtg ggaggtggga gaaccagcgg ggaggggtgt cccaggggct ccgggccgcc    8760
cccgccccag catgcagatc cgtccgtggc gagggccctg ggcgcgcgag atgggagagg    8820
gatcgttaag acccaccac cgggctgcga tgggggctga agtgagctga actgccgtag    8880 ggtcaggggcc ccgcgaccct cgccccgtac ctctacactg gggagaaacc caccctcctc    8940
gcagcctcct gaggggggcc gaagcgagcg ggctcgggat cgcggacgcc gagacccag    9000 cccgggaccc acacgcccgc ggggaagggg ccggggagcg gacgaggccc ggcgcgggca    9060
ggggggtggg tagggtctca ccaggaaccg cagcagtctg ctcggccgag ctgctttacg    9120
gcgccgtaaa aggcgctgcg tgcgcaggcg ctcgacgggc caggcgtgtg ggcggggcgc    9180
gcgcagcggt gcctgagagc ggccgcaggg gggcgcgcga gtccgcggag ccggacccag    9240
ggacgtggcc cacggccgtg atggctgctc cgcgcgtggc cagggtctcg ctggctctgg    9300 gtgggcccacg ctgaggggga cgcttgcagg cctagtcacc tgctcagggc gcacgtatga    9360
caatgggcca atgtataccc ttgcacatgg acacacctgt tggcttttcc aggcactcct    9420
atgtccttgg ggatgggttc aattgtctca agtgcatcca tgtggcccgc ggtggctccc    9480
gcctgtaacc ccagcatttt cggaggcgga ggtgggagaa tcacttgagg ccaggagttt    9540
gagaccagcc tggacaacat agctagactc ccacttcttt aaaaaaaatt agccaggtgt    9600
ggtggtgtga acctgtaatc ccatctactc gggaggcgga ggcaagagga tcgcctgagc    9660
ccaggaggtc gaggctgcaa tgagtcatga tcgtaccact gccctccagc ctgggtgata    9720
gagcgagacc ctgtctcaaa aaaacaaaaa caaacaacaa caacaacaaa tcaagtgcat    9780
```

```
gcatgagcgg tggacatagt accttagggt catgtacact catggataca tgctcaatgg   9840
catagataca ctcacgggca caattacaca cgtgggtaca cgcttagggc ttgtatatat   9900
ccgtggtccc aggtacactc agggagatgt tgtatgctca ggggcaccca ctctgggaca   9960
cagggaagac acagggaatg agttactcat tcacagatgc acaggtactc acgcagggca  10020
ctcagtctcg cccaccctgg tgccccgggg tcattgtcac gtgcagactc tccctctccc  10080
caggtcccaa aaccccctccc cttgccccag taacaggtcc catagcgacg ctgttttccc  10140
ttgactttat ttatcttcat aagtcacaaa atgtgagtgc agagataaat gtctgtgtgc  10200
atgtgccctg agcacacagg gtggcataac tcggcacact cataatgaca cagccgttca  10260
cccagccaca gatagtgaca gggcacacat ggcgacaccc acatgtacgg agataaatct  10320
cccccaccat gacatgggta gacagaaaac acgccgcagt atactctagt atgtttacac  10380
aaacagggag acaggcccgt gcaatgcatg tcaccaacac ccacactcag agtgacatct  10440
gctggaggtg ctcagacaca gccacccacc gtgacatgcc gagactcaca tatgtcacat  10500
gacacaggca tgcatgccac attcactgtg actctcagtc ctattcattc atcacctttc  10560
tgggagatac actgaaatgt ccacccttig caaaatgcac acacgcgc acgcacacac  10620 gcacatacac gaacacacgc gcacacacgc acacacacgc acgcaggtgt acacacacac  10680
gagcaactcc gagacactca ttcaccatga ctcgaggttt ttctatacgt gggacgaggg  10740
gcaggttcac actaggctgg ggggggggg tcatttcccg tcttcgttgg caggtgcagc  10800
cccatcttcc aagttgtggc tttggctgcc acaatgtcct ctcatttatt gaggtgagga  10860
ctctggggat ggggagagac ccacagtgag gcagatcccg cccctgggag aggagctggg  10920
gctaaatctg aagccccacc caccctcctc cacctcctgt cggggcgcca acttacgtgg  10980
cattttctgc agcacctcca agatttctg taccttgtg tcaatgtttt ttatgcctag  11040
ggggcgggga gggttgggtg ggaacagata agtcaagctg cggtggagcc tcaaacaaag  11100 cccccaccit ccttggaagc accccccctg ccccacaccc accctggggt acagcagagc  11160
ccatggattt ggggttccca ggagcctttc aatacccaca gagcaaccca gatggtaaca  11220
cccatcgccc ctccacaact tgagctttgg gagggtagga ccccggcttt ctcctcccct  11280
gaatcccctg cccccagctc agctccgggc attggtgaca aataacccc atagaaggcg  11340 agactacaca ggcacctgct aatgtcgtct ctaatctatc aatcttgctc ctgaccatgg  11400
tgatgctctg ctgaacggaa tcccagcctc tcttctgtct ctcttcgcat gcttgtacgg  11460
agtttgagac tgagggcatg aaacaggggt gtctgtgcat ccatccctct ccagaccccc  11520
accatgaccc cacgggtctc cctcagaccc tccgctcacc attccaaagc tcccttttaa  11580 agccccagcag ctccttggac atctcagcat ctgttcagga ggggcaggaa aatccttgaa  11640
gcacccaggg agagagagag agaaggacaa gggagaaagt ctaggccccc cagcaccctc  11700
ctcccaagaa gtactcactc ttcaccatga tgaaggctga caggatgatg cagaggacaa  11760
aggccagggc caggaggatg tacaggctca ggatggctct gtacaaccag caggggacct  11820
gggtggagtc tgagggcggc ctgcactggg ctggactgg agcaaagagg cagcaaagtg  11880
accttgaggg gccagcacca ccactcaaac catcctcact gtctctaaca ccatggacac  11940
ctcgctcctc tcaaaaccat cagcagctgt ggtcatgcag cttgtcatca tcgtcaacaa  12000
cactgccacc accagccacc ctcagcgatc taacaccgtc accatcacag acccctctc  12060 cagcattccc caacattgtc atcatcaaca gacctcatta gcacgtcaac agctgtcacc  12120
```

```
tcttccttcc ccatcgcttc ctcccttcca cgcagcccg ggggccctgc agttgcccgc    12180
ccacctgccc cttcccaagg tgatgggatg tgagcaggtg ggtgtctgct caccttggct    12240
cgtgggtcgt gaatgaccac cctttgcatg gtcctgattt ttgaaggcca aggtgatatt    12300
ctcatagtct gggtcatggg cacctgggag gggttggaga tctgctcaga gctctgtggt    12360
gtggagagtg gatccgggat cttgttttac ccaacccttt gcactcaata aattgtaggg    12420
ggtgaaagat aaggagtgag aagctaaaat ctgcttttttg gttaagtgga gcgggtgtgt    12480
gagagtttga gtgatcacac cacacacaca tccacacaca catccacaca tcttggaggg    12540
gaaggagccc ccggccccca cctttgaccc cttacctctc ccatctgaac tctccttctt    12600 ttttttatttt tattttttac agacagagtc tccctatgtt gcccaggcca gtctccacct    12660
ccagggctca cgcaatcctc ccgcctcagc ctcccaaagt gctaggatta cagacatgag    12720
caaaagcccc cggccccca atctctcctt cttaacccct ccttccacc tcgagttccc    12780 taaccttgat tcttggctga acccccctgt ttcttgtccc tgaaggctgg tgcttgcatc    12840
ttgacttcct ggtgcttgta gatttcctcc acttccatgg tccccagccc gcaaatttgt    12900
ccatacacgt ccccgcccac cggaaggtgt gggcagatga ggaaatctgg aggtggggg    12960 aagaaagagg gggagcagcc tcctcttttc agggatccac gactctcgca ccctggggca    13020
ccctcattcc tgccccgatc aagaggctct gggagccaa gaggtctcag gaaggaccaa    13080
gaagaaaaac ctctagaccg ggagatggaa ttcgacactc ggaaatgtta caggaagctg    13140
tggtctctgt gtgtgtctgt gtctacctgg atggacctca ccctcctacc tcctctccat    13200
ttcaaaagag aagctgtgac acctcagtgt cccaactttt cgcgtaagag caaccaggct    13260
tggagacagg acccctgggt cccccacac cttcctcct ccagcctcag ctccacccct    13320
cagctccacc cccaagaagt tcttctactt ctacaagtcc ccgtggagga aaagcacaga    13380
tgtgaggcaa cgggaactaa ccactggaac gccacaccca catctgggac tgaggacaga    13440
cccacatcct tccctccctc cccaaatccc ctgcttttat acaaccctgg aggaggctgg    13500
gtgcggtggc tcacgcctgt aatcccagca ctctgggagg ctgaggtggg tggatcatct    13560
gaggtcagga gtttgaaacc agcctggcta acatggtgaa accccgtctc tactaaaaat    13620
acaaaaatta gctgggcgtg gtggcgagcg cctgtaatcc tagctactca ggaggctgag    13680
gcaggagaat cgcttaaacc tgggaggcgg aggctgcagt gagcggagat cacaccattg    13740
cactccagaa tgggtgacaa gagggaaact ctgtctcaaa aaagaaccct ggaggaacag    13800
tttcctctgc acctggaaac tccaggtttc tcattctcat ccatccatct gcttatctac    13860
ccagatactc tctctcacac atgtacacac acaggtctgc acacggacac acatcacaaa    13920
ctcatttgca tactatttgc attgtgacac tcagaaaaat agacacaagc atgcgttcac    13980
atgcccgcac tctgtctaga aggtgtctta gttcactttg tgtttatctg atcttgaaaa    14040
ctggggttac aaaaggcaca aagtagctgg gtatggtggc tcgctctgta gtcccagcta    14100
cccaggaggc tgaggtagga ggatcatttg aggccaggag tttgagacca gcgtgagcaa    14160
catagcaaga ccctgtctct ttaaatgttt tttaataatt ttttttttgag acagggtttc    14220 actctgttgc ccaggccggg gtgcagcagc gtgatcatgg ctcactgcag ctttgacctc    14280
cctggctcaa gtaatccttc gtcctcggct tcccagtag ctgaaattac aggtgggcac    14340
gacttcacct ggctaatttt tctccttttt tgagatggag ttttgtgctt gtcacccagg    14400
ctggagtgca atgacgctat ctcagctcac tgcaacctcc gcatcccagg ttcaagtcat    14460
tctcctgcct cagcctccca agtagctggg attacaggca tgcaccacca cccccggcta    14520
```

```
attttgtatt tttagtagag acggggtttc cccatgttgg tcaggctggt ctcgaactcc    14580
tgacttcacg tgatctaccc gccttggcct cccaaagtgc tgggattaca agcatcagcc    14640
accgtggccc agtctaatt ttcttatttt ttgtagagat gagggtctca atatgccgtc    14700
caggctggtc ttgatctcct gggttcaact gatcctccag ccttggtctc ccaaagtgct    14760
gggattacag gcatacattt ttatttttat ttttttctgg ccaggtgtgg tggctcacgc    14820
ctgtaatcac agcactttgg gagtctgagg cgggcggatc acctgaggtc aggagttaga    14880
gacaccagcc tgaccaatat gataaaaccc tgtctctact aaaaatgcaa aaattaactg    14940
ggcgtggtgg caggcgcctg taatctcagc cactcgggag gctgagacag gagaatcact    15000
tgaacccggg aggtggaggt tgcagtgagc cgagatcgcg ccattgcact ccagcctggg    15060
caacaagagc aaaactccgt caaaaaaaaa aaaaaaaaa gaaaaagaaa gaaagaagaa    15120
agaaggaagg aaggaagaag aaaagaagaa aaacaagta taagactgtc ttatgtgcag    15180
aaagtgatga tgttttggtt aaaaatatgt ggttaaattt cagacaactt gaatgttgag    15240
aaatgagcgt cgagatctgg tgaggataaa gttctgtttc ctaaaatatt gccaaatcct    15300
gtgtctccaa gaaagatcaa tttgataatg acttcatgcc agctgctcca tttggtctta    15360
gaaagaagtc agttactgag ctataggacc gccttctaat ggagcagacg gaccaattgg    15420
atgtgggctc tgccttgatg acaggcaca gggggtggag ccacagcgtt gcacatttcc    15480
cgggcttggg tggggctgag acgcggctcc aggctctgga cttcctttga gaaaaaggtc    15540
acgctaaacc agaggcccac aagcaatcat gtcatgtggg aaacatctgc aaagctgcct    15600
gaccagcacc cgtcccttc ataggtaac attctcaatt ttcttttaag aaagaaaatg    15660
tgtgctagat ccagcaaacc ataagctagg gattggttta cagtggacaa atgatccaga    15720
cccagccaac cagagtctaa gattgggcag agaggcgggc atttgagcaa gatccagcca    15780
atgaaacgct ggtctgggat ttttattggt ttaaccacgg gggaaaaagc attctctttt    15840
ttttccagcc ctcactaggg ctgccacaat gggaggatgt aatgggagct gtgacaggga    15900
agaatttact tgagagcaaa ggcagtgctg agaaaatcag acccgagagg aagtctgggt    15960
cctggagaca tcatttgaga ccctggttcc aagccatacc tgaacctgtt gttctaaccc    16020
tgggcttgtc agttacacaa acaagaaact tcctttttagt tttgcccaag ctagtttgaa    16080
gtggggtctg ttgtacttgc aagcagaaga atcttgcctt ggctggtctc tgtggcccac    16140
gcctgtaatc ccagcacttt ggaaggccga ggcaggtgaa tcacttaagg tcaggaattt    16200
gagaccagcc tggccaaaat ggcgaaatcc ccgtgtctac taaaaataca aaaattagcc    16260
aggagtggtg gtgggcgcct gcaatcccaa ctactcagga ggctgaagca ggagaatcac    16320
ttgaacctgg aggtggaggt tgcagtgagc tgagatcgtg ccactgcact ccagcctgga    16380
caacagagtg agactccatc tcaaaaagga agaagaagaa ggaggaggag gagaaggatg    16440
aggaggagga aggagggagt gaggagggag gagggaggag gatatcttgc ctaccacagg    16500
ggatctaggc attagctatt gaggaaattg aggctctaat agggggtttg cctgtccaca    16560
tcacctgggc agatatgacc tccaagtctg cactctgggg caggagaatg tctatgttgg    16620
aattgaggaa cctgaagaga gccctcttag gtttcagata caggactatt ggatgggggt    16680
ggagacaaat agttctgggg acaatggagc atccccgccc ccaacacaca cacacagcag    16740
taaggggcag ggacacacac aaggcactag actcaccctc tctggccctg gccatgcttc    16800
taactcagtg gtcctgccct accccatga ccactgtgga gtcaggagag agggtctggg    16860
```

```
aagggaatcc ctgggctgga gtctgggtgg ggtccctggc accagaagtg gttgtaatct    16920
ctgctcatgg ccaccagcat cagacagggg gctgggacca tcacagggg tgggtggcag     16980 tgggaggaga gtccaaaaca tcctgcaaac cagaacctca ctctatcatc tgttgtccag    17040
gtgtgacatt tgagtctggg atcccttca agactaggtg ctaggaattc tgaagtctgt    17100
ggtgggaaat cagggactgg atggcaagac tcctgggtca ggcttcctgt agaactggac    17160
cccgaatcac ctgaatttgt gccccaggga gctgaggcgg gggatgctga ggcttttgcc    17220
cactagaaca ggggtcccca gccaccgggc attgggaacg gggcctcaca gcaggaggtg    17280
agtggtgggc gagcgagaga agcttcatct gtatttacag ccactcccca tcattcgcat    17340
taccacctga gctccacctc ctgtcagacc agcagcagca ttagattctc ataggagcaa    17400
gaatcccatc gtgaactgcg catttgaggg atgtagcttt ctcacttctt ataagaatca    17460
aatgcctggt aatctgtcgc tgtctcccat caccctcagc tgggaccatc tagttgcagg    17520
aacacaagct cagggctccc accgattcca cattatggtg agttgtagaa ttattttatt    17580
ctatattaca atgtcataat aataaaaata aagtgaataa taaatgtaat gcgcttgaat    17640
cacccagaaa ccatccccgc tccccccta ccccatacac acaccaactg tcttccatga    17700
aaacagtctc tggtgccaaa aaggttgggg atcgctgcac tagggtatca gatacttatc    17760
caggtgcagt ggggactaga gtcagaaatg caagagtctg cctggagcat gtgtgtgttt    17820
gtgtcctgca tcatctctgc ccaccatagt caaatctgcg attctccgtg cattggccgg    17880
gggggtggtg cctttctgtg tccaagagtg tctaggggca catgggtgtg tctgtggatg    17940
tggtgtctcc atgtggccgt ggtaggtggg ttgtgtactc tgtgtgtgca cgtggctgtg    18000
tatagctgtg tgtgcatgtg cagtatgtgc acgtcggtgc tgtatctaag tgcacatgtg    18060
gctactgatc aacagacatt tactgaacgt ctactgtgtt ccatgctcta ttctaaaccc    18120
tgggggcgct gggtgcagtg gctcatgcct gtaatcccag cactttggaa ggccgaggtg    18180
ggtggatcac ctgaggtcag gagtttgaga ctagcctggc caacatggtg aaacccgctc    18240
tctactaaaa atacaaatta gctgggcatg gtggtgggca cctgtaatct cagctacttg    18300
agaggctaag gcaggaatat cacttgaacc caggaggcag aggttgcagt gagccgagat    18360
tgtgccactg cactccagcc tgggcgccag agtaagacct tgtctcgaaa ataaaaatta    18420
aaaaataggc caggcgcggt ggctcatgca tgtaatccca gcactttggg aggctgaggc    18480
gggtgaatcg cttgaggcca ggagctcaag accaacctag ccaacatggt gaaactcctt    18540
ctctactaaa aatacaaaaa ttagccaggt atggtggcga gcgcctgtag tcccagctac    18600
gtgggaggct gaggcaggag aatcgcttga acccaggagg cagaggttgc ggtgagccga    18660
gattgcacca ctgcactcca gcctgggcaa cagagcgaga ccctgtctca aaaaaaaaaa    18720
aagaaagaaa gaaagaaaag agaagagggg agaggagggg aggggagggg aggggagggg    18780
aggggagggg aagggaaggg aagaaacgaa accctgggg ggatctagga gcagacaagt     18840
cccctgctct gtgttttcat aatctagtat ccaggaaggg gtaagcaccc tgcgtgtatc    18900
tggttgtaac taactactca caactgcact tgcctgtgtg aaaacgtgag cttgtgatga    18960
tgcgtgacgt caggtaggcg tccctgactc tccgtaaccc aactttgcct gtgccttggg    19020
gattcctcct tgcaggtagg aagtgagggg tacaggttcc agctctggc tgagacatga     19080 ttcagggttc caccctgacc tggggctcct ggagtcttgg ggccctggag gtcccgtcc     19140 actgcccaga ctgacccagg tcctcgatga agcctcatta tgaggactgg gggaaaagga    19200
cccagccact tcctggggag gtcggagacc ccaggggtgag cgtcaaggta gcctcaaaga    19260
```

```
tgagacgtca cctcttgaag gcagccatga gccttgggtg gggacgtcac tagaggaagt   19320
tcaggcccta ttttcggagg aagcagttgg agaccccata ggaggaaggg cgatggggca   19380
gtagaaagtc gcggtgtccc cgcccctcc agcagctacg cgccccactc tcttggagac    19440
gctagatcag tccctccggg cctactaaag aaaccacgca gggctcagat ccgctccatc   19500
atcatcatca tcatcatcat catcatctcc aggtttattt ccagctcccc cgcaaccct   19560 ccggacctgg agccgcctcc gcccgcgctg tgcacgcgct gcgcgcgacc tcagggctgc   19620
acacgacagc agcgcgctcc ggtccagtcc atgcccgcgc actggcagtg acatgtggtc   19680
tcggcgcgca catcccacga gccacaggcg gagccacaag tgcagccggt gacggcgaag   19740
cctgcagccc ggaacacagg agcgtggact ctgagctggg aggctgaggg tgggagcggg   19800 agggggtgg ggagcgcgga ggggggttgg ggggcgggg gtggggacgg ggacggctgg    19860
aggctccaac cactgaatgg gcactggagg caggagtga gggtggacac cagtgtccag    19920
atggtgggcg gagaaggctg ggagtcagga ccaagatcct aggggagtag aggctggaca   19980
cggggaacgt ggcggggagg gggcattccc aggggacttg gaacagaaat gggcgcctgg   20040
acaacagtct cctgcactca cctcggggc aagtagccag gtcccctg gaggtgacgc     20100 tctggcactc caggccaatg ctgcttattg ccctaaatac tgggggcag gaggaaagga    20160 gacaggggga gctgtgagac caaacggtcc ctcccccatc ctccctagc cctgttggtt    20220 tggagctagg tccctgtggg cataggagct cactggcctc caggaccctg tcttgagttg   20280
ggtgttttgg agtaagggaa ggtttggagt gagagcgggg attgggttg gagccgtgga    20340 taaggtgggg acagtcggag gggttgggag tggagttggg gttgaattta tgatctggtt   20400
ggatttgagg atgagatttg gtgagcgctg gggctgggtt ggagtcaggt ctgtgccagg   20460
gatcagtgag gtctctgaga cccttgggga gcttgcccaa gtgggggtc ctcacttagg    20520 gagccggcga cctcctggat cctctcattg atggcttctt ccatgagca cagggtcttg    20580 ctagacacca acagcccag acagggagg aggaggagac agagagcttt catcctgcag     20640
gcgctgaaag agggaaccaa gagacccaca gctggatcag ccctgccctg tggggaagat   20700
ccggcccatg gagggagtag gatctgcccc tggacctgga cccctgtccc ccatgtggg    20760 ggacagggat ggaggctcag ccttgacccc agcctccccg ctggtgccat ggcaagcgca   20820
ggagcagctg tcacttaccc tctcggtggg ctcagctaac caaatccggc acacgaattc   20880
ctgcaccgca gctcttttctt tgaggcctct tggggtgggg cttcctggct tggctaataa   20940
gtccctgggc ccccaaccct ccggtcccac atccggggcc aagaggaagc ccctgagcag   21000
acagtaaggg ctggaggagg aagggagcct tcccacttcc aacagggcct ccgtcttcat   21060
gtccagagac tggtcaggag gtggtgcccc agggataatg ccaggggctg tggtctgagg   21120
aacaggtaga caagcagagt tttgcatgca agggtggctg atgcaaacat gacaaaatta   21180
atgcctcttg ctaggcatgg tgcggacaag cacttgtagt cccagctact aaggaggctg   21240
acgtgagaga attgcttgag cccgggagtt cgaagctaca gtgacttatg atcacagcac   21300
tgcactccag tctgggcaac agagcaagac cacttctcta aaatagtaat aataattatg   21360
tctctgggtg agaatgacat accacattca tacccaaatg cccatgagca atagaactgg   21420
taaataaaat catggtttat ggccggtggc tcacgcctgt aatcccagca ctttgggagg   21480
ccaaggcggg cggatcactt gaggtcagga gcttgagacc aacctggcca acatgatgaa   21540
accctgtctc cattagacat acaaaaatta actgggcgtg gtggcgtgtg cctgtaatcc   21600
```

```
cagctacttg ggaggctgag gtgggagaat cacttgaacc cgggatgtgg aggttgcagt   21660
gcactgagat cgtgcccctg cactccatcc tggatgacta gcttgggcac catagcaaga   21720
ctccatctca aaaagaagaa agaaaaatca tggtttattc catcaatggc atcacctgca   21780
acagaagttg gaaagccatt gctcatgggc caagtccagc tcatgtttct tcttggacca   21840
cccatgagct tggaatggtt attacatttt tatttgttct ttgtttccag tacaacgggc   21900
cttttgtggt aaaatacata taacatacaa cttaccatta taacttactt ttttcttttt   21960
tgagacggaa tcttgctctg tcgcccaggc tggagtgcag tggcgcgatc tcggctcact   22020
acaagctccg cctcctgggt tcacgccatt ctcctgcttc agcctcccaa gtagctggga   22080
ctacaggcgc ctgccaccac gcccagctaa ttttttgtat tttttttttt ttagtagaga   22140
tggagtttca ccgtgttagc caggatggtc tcgatcccct gaccttgtga tctgcccgcc   22200
ttggcctccc aaagtgctgg gattacaggc gtgaaccacc gtgcccggcc ttttttttt   22260 ttttttttgag acggggtctt gctatgttgc ccaagctagt gtcagactcc tggcttcaag   22320
taatcctccc accttggact ccccagtagc tgaagctaca ggtatgcacc atcttgttcc   22380
attttaacca ttgcttttgt ttgtttcttt gtttcagagt ctcactcagt tgctcaggct   22440
ggagtacagt ggctcaatct tggctcactg caacctccac ctcctgggtt caagcaattc   22500
tcctgcctca gcctcccgag tagctgggat tacaggcgtg caccaccatg cccggctaat   22560
tttttgtatt tttagtagag atggggtttc accatgttgg ccaggctggt ctcaaattcc   22620
tgacctcaag tgatccaccc gcctcagcct cccaaagtgc cgggattaca ggtgtgagcc   22680
accatgccca gcctatttta accattttc agagcacaat tctgtggcaa taagcacatt   22740
catgttgtta tgtagccacc actgccgtcc atctccagaa ctttctcctc tttccaaact   22800
gaaactctgt ccccatgaaa cactcactcc ctatccctct ccccagcccc tggcaccctc   22860
catcttgctt tctgcctcta tggatctgat gactctaggg acctcctagg agtggaatca   22920
cacagtgttt gtccttttgt atctgcttat ttcactgagc ataatatccc caaggttcat   22980
ccctgctgta gcctgagtca gaactgtttt cctttccatg gctgtatcac attcccttgt   23040
gtggatgaac cacgttgtgt ttattccttc atccatcgat ggacacttgg gttgcttcca   23100
gcttttgttt tgttttttg tttgtttgtt tgttttgtt agttcacgtc ttttgtgggt   23160
tttctttctt ttttgagatg gagtctcact ctgttgccct ggctggagtg cagtggcacg   23220
atctcggctc actgcaagct ccgcctcccg ggttcactcc attctcctgc ctcagcctcc   23280
cgagtagctg ggactatagg cgcccgccac catgcccagc taattttttt gtattttag   23340 tagagacggg gtttcaccat gttagccagg atggtctcga tctcctgacc ttgtgatccg   23400
cccgtctcgg cctcccaaag tgctgggatt acaggtgtaa gccactgcgc ctggccgtct   23460
tttgttaatt catacagtta tttgtcttct ggtttgttga agcagtaagt cagacaacat   23520
ttgccacaat aatgtctgtc aaagtggctt gccataaaca ctgcagcacc acattcatca   23580
gaagggcaac ctcgacgaag gtgactaatt ttgccattct catccaacctt ataatatttc   23640 aggacagcca gcttcacctt cttttctctt tgcttattcg tcttgcaggt aagacttctt   23700
cttctggccg ggctcagtgg ctcaggcctg taatcccagc actttgggag gccgaggcag   23760
gtggatcacg aggtcaggag ttcaagacca gcctggccaa catggtgaaa tcctgtctct   23820
actaaaaata caaaaattag ctgggcgtgg tggcacgtgc ctgtaatccc agctactcgg   23880
gaggctgagg caggagaatt gcttgaactg ggacccggga ggcagaggtt gcagtgagcc   23940
gagattgcac cactgcactc cagcctgagc tacagagcga gactccatct caaaaaaaat   24000
```

```
aaaaaaaaga cttcttcctt tccttagcac caccacgaat tctcaataca agatgaagag    24060
gagactcctt ttgaatgttg tagtcagaca gagtacgccc atcttccagt gcttgtcttt    24120
gctgatcagg aggaattctt tctttaccct ggatcttggc ctttacattt tctaccatat    24180
ctgagggttc agcctcgagg gtggtggtct tccctgtaag ggttttcagg aaaatctaca    24240
ttttggtggc ggctccacca cagatggcgg atctaaaagg tttttgtttt ttgtttttt    24300 gagacagagt ttcgctcttg tcacccaggc tggagtgcaa gtggcacgat cttggctcac    24360
tgcaacctct gactcctggg tttaagtgat tatcctgcct cggcctccga gtagccagga    24420
ttacaggcat gtgccaccac cacacctggc taatttttt ttctttttgta tttttagtag    24480 agatggggtt ttgccatgtt ggccaggctg gtctcaaact cctgatctgg agtgatccgc    24540
ctgcctcggc ctcccaaagt cctgggatta caggtgtgag ccactgtgcc tggcctgctt    24600
ctgccttttg gctattgtga ataatgctgc tctgaacata gatgtgcaaa tatctgtttg    24660
cagctcctgc tttcaattct tctgggcgta tgtccaggag tagtgctgcc tgatcatatg    24720
gtaattctat gtttaacttt ttgaggcact gccaattttc acatttttaa accataggga    24780 aaaaaagtt gttttttttt taaaaaagac acagtctggc tctgttttcc acgctggagt    24840
gcaatggtgc aatcatagct cactgcagcc tcaaactcct gggctcaagc aatcccccc    24900 tcatcagcct cttgagtagg tgggactacg gcatgtgtca ccacacctaa ctaattttt    24960 taatttttt gtagaggtgg ggtctcactc tattgcccag gctggtctca aactcctggc    25020
ctcaaaagat cctgccacct tagcttccca aagcactgag attacaggca tgagccactg    25080
tgcctagcca aaaatatttt gtaatgttta gtgaaaatag aaatcatata aaattcaaat    25140
tcatataatt ttcataaaaa gtccataaag aaaattttct taaaacattg tcagctgggt    25200
gcggtggctc atgcctgtaa tcacagcact tgggaggct aaggcgggtg gatcacctga    25260
ggtcaggagt tcaagaccag cctggccaat gtggtgaaac cccatcacta cttacaatac    25320
aaaattagcc gggtgtggtg gcacgcgact gtaatcccag ctacttgaga ggccgaggca    25380
ggagaattgc ttgaacccgg gaggtggagg ttgcagtgag tcaagatggt gcccttgcac    25440
tccagcctgg gcaacaagag cgaaactctg tctcaaaaaa aaaaaaatt gccaagctca    25500 gtggcaggca cctgtcatcc tagctacttg agagaccaaa gcaggaggat tgtttgagcc    25560
caggagtttg agggcagcct gagcaacata gtgagatcct gtccctacaa acacacac    25620 acagtttgct accccctttt ttttgagagg gagactcgct cttgtcaccc aggctggagt    25680
gcagtggcac gaccttggct caccgcaacc tctgcctccc gggttaaagc gattctcctg    25740
cctcagcctc ccgagtagct gggattatag gcaggtgcgc caccatgtcc ggctaatttt    25800
tgtattttta gtagagatgg gatttcgcca tgttagccag gctggcttcg atctcctgat    25860
ctcaagtgat ccgcccgcct tggcctccca gagtgctgag actataggca tgagccactg    25920
cacctggccc catttttaa tatatcatca gtgactgcta tcacatgtcc atggcagagc    25980
tcagcagctg tagagtggtt ggacagtagg gcccccaaag ctgagaatgt ttactatctg    26040
actcgttaca gaaaacattt ttttgtaccc ctggtatgtg gtgatgagtg agaatgagac    26100
aactgtccat ggattacagc tacacccaac catgtggctg attctcacga acatatgtta    26160
gcatagaagc cagaccccaa aaagaacata ccatacaaat ccatttatta aaaaaaagg    26220 gggccgggcg cggtggctcc tgcctgtaat cccagcactt ggggaggcca aggcaggcgg    26280
atcacaaggt caggagatca agaccatcct ggctaacacg gtgaaacccc atctctacta    26340
```

```
aaaatccaaa aaaattagcc gggcgtggtg gcaggcacct gcagtcccag ctcctcggga   26400
ggctgaggca ggagaacggt gtgaacccgg gaggcggagc ttgcagtgag ccagatggc    26460
gccactgcac tccagcctgg gcgacagagc aagactccgt ctcaaaaaaa aaaaaaaata   26520
cctaaaaata caaaaattag ccaggtgtag cggcaggtgc ctgtaatccc agctactcgg   26580
gatgctgagg gaggagaatc gcttgaacca agaggtggag gttgcagtga gctgaaatca   26640
tgctactgca ctccagcctg gcaacagag agagactccg tctcacaata atgataataa    26700
taataaatga aatacaaaca aaactaattt atgctgtcgg aaatgacgat ggaagagtcc   26760
tggggaatca gagatagtgg tgataaaagc ataccaggaa ggcccctagt gagggggaa    26820
ttttgtaaaa gttttcagct gtaactctca tttgcacaat tttctctatg tatttatatt   26880
tcaatcaaca tgatgcatgt gtattaaagc cctgtgtaaa tgcaacggtg cacacaggtt   26940
caaagcgcag gcaatattta ttgagcaact attatgttcc atatgctgtg ttaaacacca   27000
tgcatacact aagaagcaga gggatgctgc ccttgcccgg gacgagttgg cccttgtcag   27060
tcagggaaag gcagacacca acagaacagc aataaaaagg ccgggcaatg gccaggcgc    27120
ggtggctcat gcttgtaatc ccagcctttt gggaggccga ggcgggtgga tcacctgagg   27180
tcgggagttc gagaccagcg tgaccaacat ggagaaaccc cttttctact aaaaacacaa   27240
aattagccag gcgtggtggc acaccaggtg ggtagctgta atcctagtta ctcgggaggc   27300
tgaggcagga gaattgcttg aacccgggag gcggaggttg tggtgagcca aggttgtgcc   27360
attgctttcc agcctgggca acaaaaagca aaactccatc tcaaaaaaaa aaaaaaagt    27420
ccgggcgcca tggctcacac ctgtaatccc agtgctttag gagaccgagg tgggtggatc   27480
acttgagccc aggagttcaa gaccagcctg ccaacacag tgagaccctc cctctgtaca    27540
aaacgtaaga aaacattagg cagggatggt ggtggcttcc tgtagtccca gctactcagg   27600
aggctgagac agaagtaccg cttgagtcca ggagttggag actgcagtga gctatgatcg   27660
caccactgca ctccagcctg gacaacagag caagacccca tctctaaaaa aagaaaaca    27720
aaaaaacaac aacaaaaaac accaatagaa tgctcaatca gccatcagcc tcaaggaccc   27780
ttccatctcc caaggagagg aacccttttc cgtgagaacc tctgacctaa aaatcaaccc   27840
cacatggggg aatccagaaa gtattttggg gggaggaaaa gatgtttgaa gggagggtgg   27900
aggatgcaga agggttaacc aggagaggca gttagggagg gccttctggg tggagggaga   27960
ggactgcatg ttccaaggac ctgaggcaga atggagtgtg tgtatttaga ggaactgaaa   28020
gcaaatttgt gggacagggg atctagaggg gaaaagtgaa ttccacaggc tccctgtctc   28080
ttctggtcct agcaggaact ttcaagtccg ttttttgtcca gatatttccc catgctcaag   28140
tcccagctca tcctgcctcc ttgaagacat gacttctgtc tcttcttgag ctactctttg   28200
acacaccctg acaaagggt agcttgaaaa gagacagaaa ccatgttatt gccaggtgca    28260
gtggctcacg cctgtcatcc ttgtgctttg ggaggctgag gcaggaggat cgcttgaggc   28320
caggagcttg agaccagcct ggacaacata acaagacccc atctctacaa agataaaagg   28380
gaaaaagccg ggcgcagtgg ttcacgcctg taatcccagc actttgggag gccaaggtgg   28440
gcagatcacc tgaggtcagg agttcgagac cagcctggcc aacatggcga aaccccgtct   28500
ctactaaaaa tacaaaaatt agatgggcgt ggtggcgggc acctgtaatc ccagctactc   28560
gggaggctga ggcaggaaaa tcacttgaac ccaggaggtg gaggttgcag tgagctgaga   28620
ttgcaccact gcactccagc ctgggcgaca gagtgagcct tggtctcaat caatcaatca   28680
atcaatcaat ggaaaaaaat tagctgggtg tggtggtcca tgctggtagt cccagctact   28740
```

```
gaggaggctg gggtgtgagg atcacttgag cccaggaagg ctgagactgc aatgagctat    28800
gatggcatca ctgcactcca gcctggacaa caaagcaaga tcccgtctca aaaaaaaga    28860 agaaaaagaa aaatcatttt ttgagagctc tgattttcaa acctttgtt ctcagaactc     28920 ttcgggtaaa accttttgaa cgacacaaaa ggagtgggca gctgtgatga cagattgagg    28980
agaaagcagg gtaggcatgg aacctctagg gttccctagg gacccagttt gaaaactctt    29040
ggttcagtag caggaaaagg caatatgccc cttaattctc ttctaaaaca taaaatcctt    29100
taacttcctc tgatttctac cagtaaaact gagctctact gacctcaatt ttgtaccaaa    29160
tgctatctaa taaaatccca gaaacagtga tttttgaaaa atccattttg ttgatgtgta    29220
atttacatac agtagaatgt gcctatctta tgtgtttggt ttcatgcatt gttttttcttt   29280 ttcaacttt taaattttt ttttttttg agacagggtc tcactctgtt gcccaggttg       29340
gcgtgcagtg gcacaatctc ggctcactgc aaccttcgcc tctcgggttc aagcaattct    29400
cctgcctcag cctcctgagt aggtgggacc acaggcacgc gccactacac ccagctaatt    29460
tttgtatttt tagtagagac agggtttctc catgttggcc aggttggtct cgaactcttg    29520
acctcaagtg atccacccac ttcggcctcc caaagtgctg ggaccacagg cacacaccac    29580
cacgcccaac taattttgt attttcata gagatgggt ttcaccatgt tgcccaggct       29640
ggtctcaaac tcctggcctc aagtgatctg cctgccttgg cctcccaaag tgctggaatt    29700
acaggcataa gccaccatgg ccagccctct ttatcaactt ttatttattt tttcattttt    29760
ttgagacgga gtctcgctct gttgcccaaa ctggagtgca gcggtgcgac ctcagctcac    29820
tgcaacctcc gcctcccggg ttcaagcgat tctcctgcat cagcctccca agtagctggg    29880
attacaggtg cccgccacca cgcccatcta attttgtat ttttagtgga cgggttt       29940 caccatgttg cccaggctgg tctcgaactc ctggcctcaa agcgacctgc ccgccttggc    30000
ctcccaaagt gctgggatta cagttgtgag ccgccgcgcc cgggaccctc tttatcaact    30060 tttatttag attcagggga tacctgtgcc agtctcctac ctgagtatat tgcatgatgc     30120
tgaggtttgg ggtatgagcg actctgtcac ccagatggtg agcacagcac tcaacagtta    30180
gattttcaac cctcatgccc ctttttcctca ccctccctg gcaatcccca ctgttcatta   30240
ttgccacctt tatgtccatg agtacctgaa gtttagatcc cacttataag tgagaacagg    30300
cagtctttgg tctgctgtta ctgagtttga tgcattttga caaatgtgtc tacctgcctg    30360
ctgcacgttt tggttttccc aagaattatt ttctaaaaat cagtttttat taaggtggca    30420
tttatataca ctaaaattct gcacacgatc ttgtaaccat caccaccaaa tacgtattta    30480
tttatttatt attattttt agagatggcg tctcactctg tctcgatctc ccacgccggg    30540
gtgcagtggt gccatcagag ctcactgcat cctccaactc ctgggctcaa gcgatcctcc    30600
tgcctcagcc tcctgagtag ctaggactac aggcacccac caccacccac agttaattga    30660
aaaaattgat tcttctttgt agagacaggg tctcatatgt tgccaggatc cttggtcttt    30720
gacctcccaa agtgcagaga ttacaggcat gcaccactaa tgccgggcca atacttgta     30780 atttaaatta tcgctgggct gggcacggtg gctcacgcct gtaacccagc actttgggag    30840
gccgaggggg gaagttcacc tgaggtcagg agttccagac cagcctggcc aacatgctga    30900
aaccctgtct caactaaaaa tacaaaaatc agccggacat tgtggcagac gcctgtaatc    30960
ccagctaatc gggaggctaa gacaggagaa tcgcttgaac ccgggaggca gaggttgcag    31020
tgagccgaga tcgcaccatt gtgctccaac ctgggcaaca agagcgaaac tccatctcaa    31080
```

```
aaaataataa taaaataaat tatagttgga aaaaaggggt ttcctaaaga cccaagggaa    31140
atggcctctt tgttcctgaa gccacagaga ggattttttct gctccccaca actagttttc   31200
cttgtgaaaa ttcataattg ctaccagctt gttctcctct ctgtcactat acatctgtcc   31260
ttgaagcctt atttgaacaa agagttctgg tatcactcgg atgcctagaa actgttgccg   31320
ttctgtgaaa ccgaccacca gaggaaaccc atgcttctca ttggctgcct tactaagatg   31380
gtgacttgtt gccctggtga caagttgcaa tgacaggtgg ctctgccaaa tcagaacaca   31440
gtgatacttg cttcccctcc cgggtgaagg atggaaaata aagtaaaag ccttggcggc    31500
tgtcaggctt ctttaccaaa gagctggaga gcactccttg gccccattta tgcaaacact   31560
tcccatctac agatgatcca gcttcggagt gggagtctaa gcagctgcca ggaccaccgc   31620
ttggcagagg acaggctggg ggctctggca tgacctgctg gggccaggct gtgacttgga   31680
gcaagaggta gcaagaacct cgaggcagtg aacatcaaaa gagagatttc cggggctaaa   31740
cacccctagg ttttccttcc tcctgaaccc taaccctaac cctctcggct cactgcaacc   31800
tccacctccc gagtgcaagc aattctcatg cctcagcctc ccgagtagct gggatcacag   31860
gcgtgcgcca ccacgcccgg ctaactttgt attttatta gagacggggg tttctccacg    31920
ttggtcaggc tggtgtcaaa ctctcgaact caggtgatct gcccgccttg gcctccaaaa   31980
gtgctgggat tacaggcgtg cgccaccgtg cccagcttat ttttgtattt ttagtagagg   32040
tggggtttca ccctgttggc caggctggtc ttgaactcct gaactcaagt gatctgcctg   32100
cctcagcctg ccaaaatgct ggggttacag gcgccaggcc aagtatctta ttttaaaagg   32160
ttacaaagaa tatagatgtg gataaaataa aagtttcttt gcattaccac tttcctgcaa   32220
gaaatgaggg ggaggggctt atgaaacaac tcacacccc ccaattgagg aactgtagat    32280
gaaagggaag gtgctgacag gcccgtctgg ccacggtttc ctggaataaa actgagccac   32340
acacctccac aaatcccag cctccggcaa gtacccagaa agtactcaca ctccaccacc    32400
ttctgtgatc gcaacagccc tacgcaacat tacagagggc aaaacccacg ctggggaagg   32460
cggggctact gtcaaaaggt caccagggcc aggcacagtg gctcacgcct ataatcccag   32520
ctccttggga gaccaaggca ggaggatccg ttgagctcaa gagtttgagt tcagcctggg   32580
caacacagga aaaccccgt ctttacaaaa acttttttaaa aattagctgg gtgtggtggc    32640
atgcccgtgt aatcccagcc actcttagg aggccgaagg gggaggatct attgcttcag    32700
cccgggagtt gtggctgca gtgagctatg attgcaccac tgcactccag cctaagtgac    32760
agacagagac tcttaaaaaa aaaaaaaaaa gggcagggca cggtggctta tgtctgtaat   32820
cctagcactt tgggaggccg aggcgggcag atcatctggc gtcaggagtt cgaggccaac   32880
ctggccaata tggtgaaacc ctgtctctac caaaagtaca aaacttagct gggtgtgatg   32940
gtgggcacct gtaatcccag ctactcggga ggctgaggtg ggagaatcgc ttgaatctgg   33000
gaggtggagt ttgcagtgag ccaagattgc gccactgcac tccagcctgg gtgacagaat   33060
gagactctgt ctcaaaaaaa aaaaaaaaaa gtggggcacc tatattccca gcactttggg   33120
aagctgaggc aggaggatgg cttgaggcca aaaattcaaa acccggcctg ggcaacatag   33180
caagacccca tctctatgaa aaaaaaaaaa aaaagtcac caggccagct agcctagatt     33240
tcagagccag aatttgtctg atgccattgt ctttactttt tctttttctt ttttttttt    33300
ttgagacaga gtctcactct gtcacccaag ctgcagggca gtgggacaat ctcagctcac   33360
tgcaacctct gcctcccagg ctcaagcgat tctcctgcct cagcctcctg agtagctggg   33420
attacagaca tccaccacca tttccagcta attttgtat ttttagtaga ggtgaggttt    33480
```

```
cacctttttg gtcaggctgg tctccaactc ccaagctcag gtgatctgcc cacctcagcc   33540
tcccaaagtg ctgggattac agttgcgagc caccacgcct ggactgctct tcattctttt   33600
ttcagaactt tcccagctgc caacagagac agaaactgaa tcatctcaga agtgaatgaa   33660
ggaggctgag ggcgggtgga ctgcttgatt aggagttcga gatttgccta ggcaacatgg   33720
aaaaagcctg tctctgctaa aaatacaaaa attagccggg cgtggtggca catgcctgta   33780
atgccagctg cttgggaggc tgaggcagga gaatcacttg aacccgggag gcagaggctg   33840
cagcgagccg agatcgcgcc actgcactcc agcctaggta acagggcgag actccgcctc   33900
aaaaaaaaaa gaagggaatg aaggacaccc aaaatggagc ctctgtctgc cagggctttg   33960
ctatcctggc ctgcctatcc cagccctgga cacctcatct ctgatcccac cagagcggaa   34020
ccttcccatt cgcagggcca tttccttacc cagaaacctt ttcacaatgt tcttggcagc   34080
agctgttggt caactgtgtt ttaaggtttt tgagcaactt tacagaaaat aaaagggaag   34140
ctaccctcaa tgtctgggtc tccccctggg tggcctctct ttgtcacctt actcatttcc   34200
acgagatttc cttgcttcgt tgagttacat cacctccttt tcctgtctgg gtccaggacg   34260
cctcctctgc aggtctccag cactgattcc tttgtccccg atttctctgc tagggtcgct   34320
ggcttcacca tcccaccacc actgctgctg gcccagcccg cagctttaat ttctctggac   34380
cctcacgttt ttgttatttg tgttttttt ggagatgagg tcttgctctg tcacccaggc   34440
tggagtgcag tggtgcaatc acagctcact gtagcctcca cctcccagac tcaagtgatc   34500
ttcctgcctc agcctcccaa gtagctgggt gtgtgccacc aggtgcagct acatttttg   34560
tagaggcagg ggtcttgcta tattgcccag gctggtctca aactcccagc tttagatgat   34620
cctttcacct cggcctccca gagtgctggg attaccagca tgagccactg cacccgtcct   34680
ctcatgtatt ttttattaat cgatttatct atttacttat tttgagacag agtcttgctg   34740
taccacccag gctggagtgc agtggcatga tctcggccca ctgcaacctc cactccctgg   34800
gttcaagtga ttctcctgcc tcagcctccc gagtagctgg gattacaggt gcccgccacc   34860
atgcctggct aatttttgta ttttagtag tgacgaggtt tcaccgtgtt ggccaggctg   34920
gtctcgaatt cctgacctca ggtgatccac ccaactcggc ctcccaaagt gctgggatta   34980
caggcgtgag ccaccgcact cggcctccct catgtatttt taagcggaac aggttcaaga   35040
tcacaaatgt tttcctctca ctctttcaat gagtttctat tctagaatct cctgcacgcc   35100
acaggaagga gaactctcac cctgtaatgc acataaatac atgagatcac cattgttctc   35160
acccagtaat cagaatcgtt agtgataatt agtaataaat ttattttac tatatctaat   35220
aaattagata gtaattacta tggcagccaa tcgttcctgg gtgctcccta gatgcttcca   35280
agggagccac acgtgaccct cagggctgtg cccattccag gctcttctgc tgagctcatg   35340
taaccgcttg cctcaaggca ttccacaaat aatacataag tcaatgtatc acgttgtcac   35400
tttctgtaca aaccagctag ttccggaggg aagcagaaag cctttttcag aagaaccaca   35460
gctaattcca gtagcaggaa tgataaagtt ggacataatc ctcaagagag taatgaatca   35520
aaaatggatg gcgggccagg cacggtggct gatgcctgta atcccagcac tttaggagga   35580
tgaggcaggt gaatcatttg aggtcaggag ttcaagacca gcttggccac catggtgaga   35640
ccccgtctct actaaaaata caaaaattag cctggcatgg tggctcatgc ttgtagtccc   35700
agcttcttgg gaggctgagg caggagaatt gattgaaccc tggaggtgga gattgcagtg   35760
agccaagatt gcatcactgc actccagcct gggcaacaag agcgaaactc tatctcaaaa   35820
```

```
acaaacaaac aaacaataac aacaacaaaa ttgatggctg ctaatgactt ttttctttt    35880
ctttcctttt ttatttttat tttttatgag acagggtctc actctatcgc ccaaactgga   35940
gtgcagtgcc gagatcataa ctcagtgcag cctcaacctc ttggactcaa gtgatcttcc   36000
cacctcagcc tcccatgtag ctgggactac aagcaattgc tgccacatct ggctaattat   36060
tttattttgt tgtatttat ttatttattt tttgagacag agtcttactc tgtcacccag    36120
gctggagtgc aatggcatga tctcagctca ctgcaacctc cgcctcctgg attcaagtta   36180
ttctcctacc tcagcttcct gagtagctgg ataacaggt gtgcaccacc acgcctggtt    36240
aattttggt ttttggtag agacggggtt tcatcatgtt ggccaggctg gtcttgaact     36300
cctgacctca agtgatccgc ccatctcagc ctcccaaagt gctgggatta caggtatgag   36360
ccaccgtgcc cggtctttat tttatttta gtagagacag ggttttgcta tgttgccag     36420
gctggtctca aactcctggg cctaagtgat cctcctgcct tggcctccca aagtgctggg   36480
aactacaggg gtgagccact gggcccagct cctgttaaca tctttatgtg gagagttact   36540
ggggaccagg gacattcccc aaacccaccc atcaatcgta gtgacatgac gttatggacc   36600
ccctgatgtg atgtaccagg aagtacccgg ccctaccagc atgatattat tctggctgca   36660
actgacccctt attccaatag agcatgtggt tctaagccat ttatagggta aacattgggg   36720
cagggatggg gagagaggaa gcaacctgcc aaatccagaa tgaggatcat tcctcggtac   36780
cagaagagaa ccagaaagaa agcaccctaa gtggggatac cacaaggaag taaagcaggg   36840
gcctctccca gctggggaag ggaaggagga aggagtacaa tagcttgcaa ggcacagcat   36900
tgcggatgat gggaatagca ggtgcaaagg ttctggggca gggacagtgt ggtgtgtttg   36960
aagaacagca gccaggttca ccatgagatg ggaaatggac ttgggggaag ggatctcaaa   37020
ggataatttt tttttttt ttgagacagg gtttcgctct tgttgcccag gctggagtgc    37080
agtggcatga tggctcactg caacctctgc cttccggttt caagcgattc tcctgcctca   37140
gcctcccgag tagctgggat tacaggcgcc caccaccacg cccggctaat ttttgtattt   37200
ttagtagaga cagggtttca ccatgttggc tagactggtc ttgaactcct gacctcgtga   37260
tccgcccgcc tcggcctccc aaagtgctgg gattacagac gtgagccacc gcgcccggcc   37320
ccccaacttt tttttgttt ttaacacaac ttctcgcttt ctcacccagg ctggagggca   37380
gaggcacaat catagctcac tgcagcctcg aactcctagg ctccagcgat cctcacagga   37440
gggttttgag gatctgcata aagcgtgcag agggagcttg acttcgtgct cgttaggacc   37500
cgatattgtc agctgccgcc gcccacaggg acacataaat atttgtagac tcaatatttg   37560
cctttagtgt gaagacattg catcacctgg gtataagtaa ggagcagagg cagaggcggt   37620
ttaagcaaca gacttttgtc tccgctgaga accacgaat aaccccctgac ctacttccccc   37680
gtcgtgtcta attcgggtca cctcatctcc agttacagac gcggaagatc aaagaaaccg   37740
ggaaattgcg ccgcagcgcc ccctggcgtt cgcagcgcgt gcctacacaa gccactcccg   37800
gcgcaaaact gcggcttccc aggaaattga gtttaaatgt ttttttttct ttttcttaa    37860
tctagaaaag atcatttatt gtatcaagta actacccagt taggcgtgaa tacattttaa   37920
aattttttatt aaaacgagta ttggccgggc gcggtggctc actcctgtaa tcccagcact   37980
ttgggaggcc aaggcaggtg gatcacgcg tcaggagttc gagaccatcc cggccaacat    38040
ggtgaaaccc cgtctctact aaaaatacaa aaattagctg ggcgtggtgg cacgcacctg   38100
tagtcccagc tactcgggag gctgagacag aagaatcggt tgaaccgggg aggcggaggt   38160
tgcagtgagc tgagatcatg ccactgcact ccagcctggg cgacggagcg agactccatc   38220
```

```
tccaaaaaat aaataaataa ataaatataa tataatataa aataaaataa aaagagtatt    38280
gtagagattg gctgggcaca gtggctcaca cctctaattc ctgcattttg ggaggctgag    38340
gtgggaggtc ttcagcccag gagttagaga ccagcctggc caacatggca aaaccccatc    38400
tctactaaaa gtacaaaaat tcgctgggca tggtgtcgca cgtctgtgat cccagctttt    38460
tgggaggctg aggcaggaga atcgcttgaa cccaggaggc agaggttaca gtgaatcgag    38520
atcgcaccac tgcactccag cctgggcaac agagtgagac cttgtctcaa aaatacatat    38580
atttaggaat ttgctatgtt gcccaggctg gcctcaaact cctggcctca agcaatcctc    38640
ccacctcgcc ctcccaaagt gctgggattg caggcgtgag ccactgtgcc cgaccttgag    38700
cttaagtttt aaacattaaa accacctccc tcccactccc tgcacctccc gtaagttaaa    38760
acgcgtccct gctgaggccc tgcaaaggca tatccagggc aggcggaccc cagggggtcca   38820 cagccgaccc actttcttcc ccacacctca tcccctttcac aactctcctc atccatctcc    38880
ctgccctggt gggagattcc gataaatcct aattgtggaa ctgctgaatc agagggggct    38940
gcattttcct tagcccccac ctgcaaattg tgtgtgcagt ttttctggga tgagtgtcct    39000
tagatttccc tgaattctca aaaggatctg tgacctcaaa atcaggagag aggccgggca    39060
cggtggctca cgcctgtcat cccagtactt tgggaggccg aggtgggcag atcgcttgag    39120
cccaggagac cagcctgggc aacatagcca gacccagtct ctacaaaaaa ttaaaagatt    39180
aactgggctt ggtgatgtgc actcatggtc ccagctactc aggaggctga ggtgggagga    39240
tcgcttgagc acaggcggta agagaggctc tacctctgaa gaggatgctt ccccacccctc   39300 tgcccctcc ccaggcaccc actccagcag tgagaatttc actgccaaca tgagacatgg    39360
gtccctacct gtcccaactc agaccctgtc tatgatgtcc tatggcctca gcagggacca    39420
aaaccctcac catggcctca ccagaacctc cacgtggttc tcagattggg ttgcaggtca    39480
gtaccctccc ctccagctcc tcaggggcct cctgcattct ctggccttgg cttctgctct    39540
gccctcccct cccttcctt cgcccccttc attttcattc tctatgcaaa tgctgcctcc     39600
tctaggaagc cttccctgat tgcccccagt ctgggtggat tagatgtgat atgggctccc    39660
acagcccctt ttgcctcaga ttactcatgt ggctggctgt atatctgtgc cccagagagg    39720
tttcttttcc ttttttcttt ttttttttt tttgagata gggtgtcacc ttgccaccca     39780
ggctggagtg cagtggcatg atcatagctc attgcagtct caacctcccg ggctcaagca    39840
atccttccac ctgaaagtcc tgagcagctg ggactacagg cgtgtgccat cacgtgcctg    39900
actaattttt cttatttttt gtagagatgg ggtcttgcta tgttgcccag gctggtctta    39960
aactcctagc ctcaagcgat ctcccacctc agtctcctga gtaaactgga ccccaggtgc    40020
aagacaccat gcccataaaa aaattttaaa aaaatttaat tttaaaattt ttttgtagag    40080
ataggatcgt gttatgccgc ccaggctggt ctcaaactcc tgggcccaag cgatcctccc    40140
acctaggcct cccaaagcac tgggattaca ggtgtaagct acctcgcccg gcctctcctg    40200
ttctattggt gctgtgagat tcacacctca cttgagtgct atgggctgaa ctgtgtcctc    40260
tccacaaatg tctatgctga agtcctgccc cgcaactgcc tcagaaagtg actatacttg    40320
gagatagaat cttaaagaa ataattaagt aaaaatgagg tcatatgcgt gggccctaat     40380
ccaacatgac cagtttcctt gtaagaagag cagattagga cacagacatg cactgggcg     40440 gggggaggag actgtgtgaa cacacaggga aaacacagct gtctacaagg aaaggagaga    40500
agcttcagaa ggagtcacac ctgtggacat cttcatcttg gacttccagt ctctagaaac    40560
```

```
agaagactat aaatgtgttt gctttgagac agagtcttgc tctgttgccc aggctggagt    40620
gcaacggtgc gatctcagct cactacaacc tccgcctccc gaaggaggcg tagtgtaatt    40680
ctcctgcctc agcctcccaa gtagctggta ccacaggtgt ccaccaccac acctggctaa    40740
tttttgtatt tttagtagag acaaggtttc accatgttgg ccaggcttgt cttgaactcc    40800
tgacctcagg tgatccacct gcctcagcct ctcaaagtgc tgggattata gttttgtttt    40860
tgagatggag gtctcgcttt tgtcacccaa ggctggagtg cactggcacg tcttggctc    40920
actgcaacct ctgcctccca ggctcaaatg atcctcccac ctcagcctcc tgagtagctg    40980
ggaccacggt gcacaccact acattcagct aattctattt ttttgtagac acaggatctc    41040
actatgttgc ccaggctagt cttgaactcc tggcctcaag tgatcaacct gccttggcct    41100
cccaatgtgc gactacaggc atgagccacg gtgcctggca atttctgtta agtcacctag    41160
tctgtggtac tttgttatga cagccctagc aaacagatac acccaccgaa ggccctgata    41220
agtcctgcag tcaggagtct ctgtgaaccc cgtggggctg ggaggagaaa gcagggagcg    41280
tttgctgtgt gcctcacatg aatacagcag aagctgaaca caactcctgg catcgtatgc    41340
ctacaggtcc ccttggaaca gttctagggg ggttggagtt ccagggtcca ttctgcttaa    41400
taacaatatt aacggagcag ccaaaatggt tccagtgaaa atggggtagc agcagctgtc    41460
atgcttgcac gccaccagcc ttcctgcgct atctctgttc tctcctctgc aaagcagctg    41520
ctattttggg ctccctgttt ttagattggg aaccccggaa gttggtcagg gcctcaccgc    41580
tagaatatct tagagctgat attcaaatga gagtccaatt ttttttttt tgagacggag    41640
tctcgctttg ttgcccaggt tggagtgcaa aggggcaatc tcggctcact gcagcctcca    41700
catcctgggt tcaagtgatt ctcctgcctc agcctcccaa gtagctggga ctacaggtgc    41760
acaccaccac acccagctag ttgttttgta tttctagtag agatgggttt tcaccatgtt    41820
ggccaggctg gtcttgaagt cctgacctca agtgatcctc ccgccttggc ctcccaaagt    41880
gctgggatta caggcgtgag ccaccgtgcc ctgccaaaag tccaagttct aacctccat    41940
gagggcttga gatgccctca ggggcaggga gaggctaatt ctccttctga gaggataata    42000
ggggttggtg gggcctgggg cacaggcctg gctcagcaca actcccaggg actcccttga    42060
taagaaggtg aggtaggcac tggctggcag agcgacggga agagtttatt tctctggaaa    42120
gggaggggta ggggcgggg ccaggggtca ggcagggca atgtcctcca gcttcttgtc    42180
cagtgccttc aggtcatcca ggaagcgggt cggggtgagg atgtgtgagg agcctgtgca    42240
ggggcagagg tttggggaag atgttggggg gcgctgcctt cgtctttgac aggctcccgg    42300
tcccggctgg tgtggggctg tccctgtccc tcagcaaacc aggtccctga ctccaaggac    42360
tctggagtcc agacacctag aaggtacaag cccaggcccc gggaacccaa gccccagacc    42420
ccagggtccc agtcctggtg acttaccaat gagcacctcc cacttgccct cggtggccct    42480
ggtcacctcg taggcggccc tcatctctga catggccaca ccgcccatga catacacgat    42540
gagccggggg cccgcccggg cttctatgcc agccttgttc ttgtgccagt gaccgaagcg    42600
ggcactgtgc agggcagggg cagaaagtcc aggcaggagg ccctcaccgc cgccaggccg    42660
cccacctaac acagacccag gcgtgggcgg gggcggcccc ggggcctcac ctgacagcgg    42720
cctgggagct ggccgtgggg gcgggtcgg atacgaaggg ccacaggttc ctgtccagcc    42780
ggtcctccac ggcgtcctgg cggccgagag gcaggttagg ggaggaaccc caggcatggg    42840
gtccggggtc aggagtgccc ccacggggt attcaggggc caagatcctg gcagacagga    42900
accagcatct ccacctcctg cctctggggg acccaggagt ctaggcctct agtccattgg    42960
```

```
ggacctagaa atctagatcc ataactcact ggggacccac gaatctaatt ccataactcc   43020
ttgggtaccc agaagtctaa acccacagtt cctcggcaac ccagtagtct gggcctccag   43080
gcccttgggg accatcagtc aatacccca gccctttggg gaacccagtg tctgggctct   43140
cagcccctca gagccccaga agtccaggta ttcaaggtcc atggggatga ggaggcccag   43200
gtctctggcc cccacgcaga aagaggggcc ggggctctta gagggacaag gaggaagcca   43260
ggaagccgcc ccaggcccat tgccattgga tggtgctgcc ctgggatcct gggaaggcca   43320
gggctggggc tcagggggcac tcctgcggga caggggaaca gactagagag atatagcgga   43380
ggcagccggc aggtggggag gaagtgaggc tccccagcac aggccccgct gtcacccaa   43440 ttcctcagct gcgggcttgg cgtgccccc tcagcagagc agatcggtgc caagggaatg   43500
ccagcaatga gcattttccc ctaagccctg aggcttagca cctcagcagg agggaggctg   43560
agccgccagc cgatgcggag ggctggcccc caccctgacc tgccacccag tacctccatt   43620
acatccttga tgaccggggt ccagcgggac agctgatagg tgggctccat gcgttctctc   43680
ggctccagcc ggctggaggt ccccgagccc tacaggcagg gcaggaggg cagcagggg   43740 attgagggga aggaggctgg tcacagaggg gctgcgcctg gtgtggctgg tagggtgggg   43800
gatggcaggc aaagatgggg aagtggaaca gagagcgaga gagagcgaga gacagcaaga   43860
aagcgagaga gagaaacagt gagccagaga gagacgagag gagaaagcca aagggagaga   43920
gagcgagcca gagaaagaca aagacagagg cagagatagg caaagagata agaagcagtg   43980
agacaaagta tgaaggcaaa gagagagaca agagatgaag caggaaacag agagaggaag   44040
atggggacag aaggggacg gagaggggag gggagcaaga cagagaacag agagaaaggg   44100
gaaggcagag agaagggtga gagagagaga tatgagaaa cagtgcacag cgagatggat   44160
gagggatggg ggagagatgg ggacggggtg agggcaccct ggaggggac gcacagggcc   44220 agagagagac aggagaggct gacccaagag tcaagcacac acatggctgt gtgtgggtgc   44280
tggatgggtg cggggaccc tcagagaccc ctgggagccc agatagacaa tgtggtgtag   44340
cccccatgct ggggacccta ctccctgcct ctagcactca gaccacccgc tcccaactgc   44400
accactgcca ggaccagcct ggcagcgacc atgtctcact tcccctgcct attgtgtaag   44460
ctgggactgg gagaggcccc agtgtcctct gggcccaga ccagaccga aacactgctt   44520 ttggcctccc agcaaccaca ccacgccagg aaccacaccg tgcctgtgca ccaatggccc   44580
tctgccttgc agagccccgg ctgtgatccg caccctctcc cagggtcccc ccatgcccgc   44640
tcctggcgta ccccggggtt ggtgacagtg cctcccagct gctccaggtt acggatgagg   44700
ctgctgtgcg cctgtacatt ggcatgctgg atcagcttgg ccaggttctc ctcactcaca   44760
cctgggggac gggaatgggc agggtggagg cggcggccag gtgagctccc aggtttaggg   44820
gagtttgggg tgggctgagg agctcccagg actctgatga gagaaccttg cagtggggag   44880
ggcctcagta ccctgtgcta gtgtgagcaa gagtgggaaa cctggagggg gtagatcagg   44940
ggctcctcca gatgagctga gggagcccca catctatagg aatcacagat gtgagggttt   45000
ctacgttagc agggagccct cacctcagtg gaggaatccc caagccaatg gaggagggtt   45060
cccgggtcca gaggggtagc tgtgggggtt ggtgagcccg gtgagtgcaa atgacccaag   45120
gagagctgtg gggttcagca gttcccagga tcgtgggaga cgctggcaaa tggggacgtt   45180
ccaactccct gcagccccca cccaccattc cgaaggagga tgtagagcag caggacccgg   45240
atcttgtcgt aggcgggcac cgccgcgtcc agcagcaccg gaacgatcag cttcatggag   45300
```

```
tccttgatct tctcccctc tgcgtcggag cccatggcca ggtcctgcgg gcatggggtc    45360
agccgtccac cggccgctat gtgtcaggga aggggatggg agaggcgggc caaggacatc    45420
cccaggatcc tcggcaagag gacatttggg tcctacctca tctcagcacc aggtctctca    45480
aggtcccacc cctgtccagg gacagtctct ccacaggccc tgctcctcac ccaggtccca    45540
cctttccagt gccccaccca cctacacaca ggtcacacca ctatcctgag actacctctc    45600
caaggctcca cccctcaccc aggtcccagc tctccaaggc tccacccctc acccaggtcc    45660
cagctctccg aggctccacc cctcacccag gtcccacctc tccgaggttc caccctcac    45720 ccaggtccca cctctccgag gttccacacc tcacccaggt cccactctc cgaggctcca    45780 cccctcaccc aggtcccacc tctccaaggc tccacccctc acccaagtcc cacctctcca    45840 aggtccacc cctcacccag gtcccagctc tccaaggctc accctcac ccaggtccca    45900 cctctccaag gctccacccc tcacccaggt cccacctctc cgaggttcca ccctcaccc    45960 aggtccacc tctccaaggc ccgtgcctc acccagatcc cacctctcca tggctctacc    46020
tgtctcccag ctcctacctc tccaaggccc caccctcac tcaggtccca cctctccaag    46080
gctccgcccc tctcccaggt cccacctctc ttaaggctcc accctctcc caggtccac    46140 ccctccaagg ttcaccccct catccaggtc ccacctctcc aaggttccac ccctcaccca    46200
ggtcccacct ctccaaggct ccgcccctca cccaggtccc acctccaa ggctccgcc    46260 ctctcccagg gccacctct ccaaggctcc attcctctcc caggtccac ctctccaagg    46320 ctctgcccct cacccaggtc ccacctctcc aaggctccat tcctctccca ggtcgcacct    46380
ctccaaggcc ctgcctacct ctccaaggtc ccaccacct atgaataggc cacattcctg    46440
tcctgggacc acctgtccaa ggctctgccc ctcacccaag tctgacctct ccaagcccca    46500
tccacctatg cacaggccac accctcatcc taggaccgtt tctccacaag cccactcct    46560 tccccaccag gtcccacctc tctccaaggc ccctccacct ctccacaagc cctgcccctc    46620
ccccagaacc ccccatctct acagttcagc ccctccccaa tacccgcct tggcaggacc    46680 atcacccctg ccccccgcaa gccctgcccc acctgctcca cactacacag cttctccacc    46740
gagcccttga agtgcttcat acaatcatct gctagatgca ggtgcgtaga atactgcagg    46800
gtgcagggtg ggggttgggg gataacaaag gctgagtcaa ggcagaacgc agacagagca    46860
tggggttgag gggccgaggt gtccccgctc cctgcccacc cgagcacacc ttattcagct    46920
ccttctggta ctgcggcatc tttttcagga tctgggatag gtctttgatg ttcgcctggg    46980
gaagtagggg gaagagggta gggattgggg ggcgaagcca ggcagtgccc acctgggtct    47040
cagtccaggc tcgaaatcca ggctgtggcc ctgcgcccat ggggaggggg gcttccttcc    47100
accagcgcct ttggtgacct gggtccgccc taccttgtc cgtggtcagc ctcttgctct    47160
cacagaaggt cctcaggagc tccgtgacct tcctggccat gagggtgggc ggggtgaga    47220 gtgaggggag aggagccaca ggccatgggt gagcccactc aggggggaca gggagaggtg    47280
gggtgaaatt ggaggccagt ctggagtcac acgagggtg ctcatgaggg ccaaagactt    47340
ggcagcagcc agggatccca aggccgctac caggcccaca gtgggcggtg gggggggat    47400 ccggtccccg tgtgcacgca cttggacaca tctgcgatat gcatgtggcg aagctccacc    47460
cacaagtcat cgtcctcgtc cagcaagacg gccttctccc gcgcctcgct cagcccggtg    47520
gtctcatacc tggggaggaa ggagggagcc tggggtcag gggagctgag gactggggaa    47580
ccaggtcagt ggcaagggtg gggacgggtt ccaagtctgc agacctgtat gtgtcctgct    47640
ctatgtccag cagatcatac gccatggcct ggaacgtgag ctcatgcagt agtggggaca    47700
```

```
cggggtcagc tgcccggtcc attatcagca gctgggagcg ggttttctct gggccctggg    47760
gtggggttta gggcaggaat gaggcactga ccctgagccg gttggggctg cccctcacct    47820
cccaagcacg cccctcacc tcgcccagac tgggagtgtc tgccttgaag gcgttcagct    47880
tggccaggac ggcgtgggcc aactgggctg tgtcctctgg gccctggcg gggaggtcag    47940
acacggggga catcatcagg ggatgggtc aaggatgggt ttgaaggtga gagtcagggg    48000
ccagggtagg gccggggctg gggtcacaag agaggttaaa ggttaggtgt tgcacgcggt    48060
taagggggg tcggcatcgg ggtggggctg ggtgggggtcc ccacttgcgg tagcggatgg    48120
ccgggtactc ctgcagggtg gcgcacagcg tggcaatctg ctgggccagc acctcgagct    48180
gccgcgtgcg ctcctctgcc cggaagggggc agtagaggtt gtaggtgctg tggggagcat    48240
cgagggagaa cacctgggcg aggaggggac agaagcacca gggttgccgc tgcaggtgca    48300
cacctgcccc gcttcccgct gccgccacct gcacctcctg ggagccgtcc ctggtccctg    48360
aagcctgctt tgccgaattg gaggcaggcc caggtcaacc ctaaacccat gcctgcagga    48420
gtcagtggat aaataccccca gcccgtgtcc cttaagctgg ctggcaacc ccgcggtgcg    48480
ctctacgctg ccccctgcaa gggcctagtg ggatagaact caaggcaaga gctccttgga    48540
ctctgtgggt acctcccctt tttaaaattt tactttatgt atgttttga gacaggatct    48600
cgctctgtcg cccaggctgg agggcagcag tgcaatcata gctcactgca gcctcgacct    48660
cccgggctca gcgactctc ccaccccagc cccatgagta gctaggacta caggtgcacg    48720
ccaccacgcc aagctaattt cttctttt cttttttaa gagacggggt cttgctctgt    48780
acccaggctg gtctcaaact cctggcccca agtgatcctc ctgccctggc ctcccacagc    48840
gctgggatta caggtatgag ccactgcgcc cagcctcagt gtctgttct gagggaacag    48900
gggacatttg gtcacaaacc ccaccccct gcccaggatg agcccgggcc gtacctgggc    48960
ctcgtagggg aggaaggcaa ggtgaatctc cttcaacgtc ttcaccacct ttgccagacg    49020
agagcggcct agctcactga acaggggctc ggggcaggct ggggtgaggc aggagtgggg    49080
catcaggcca gagcagcccc cacacctcct tgccccaccc accaacaccc taggctctcc    49140
tcactcactg tcggtgaaga agatatgggc cgctttgtag gtgaaagtcg gggtcccctg    49200
gaagtctttg atcagggcct gaaccgactg gggaaggtgg atcactctct gggcctgagc    49260
ctgcacacct aggctcattg gctgcctagg cctcccagcc accccccatc tgccaccatg    49320
tgcaaacatg gacggacggg gacatgtata tgtgcaaatg cacactagtg tcgcacccac    49380
atgggcacac gcgcacacac acagatgcac gcacgcacac acacatacac acgcatgcac    49440
acatgcacac acacacagat gcacacacac atacacacat gcacacacag agatgcacac    49500
acatacatac acacatgcac acacacagat gcgcgcgcac acatacatac acacatatac    49560
acacatgcag acactgatgc gcacacacac gcatacacac atgcacagac gcatacacac    49620
acgcatacac acgcacacac agatgcacac acatacatag acacatgcac acagatgcac    49680
atacatatac acgcatacac acatgcacac acagatacac acagacgcac acacagacgc    49740
agacacatac atacacacgc atacacacat gcacacagac agacgcacac acacacatac    49800
agatgcacac agatgcacac acacatacat acacacgcat acacacatgc acagacacaa    49860
atgcacacac agacccacag acacacacgc atacacacat acacacaaat gcacacacag    49920
acgcacacac atgcacatgc acacagacac atacatagac acacatgcaa acacgcacac    49980
acatgcatac acagatgcac acacacatgc acacacatgc acacacatac acatggacac    50040
```

```
atgcacacgt atacacatgc acacatgcaa tcacatgcat gcagacatac acacacatgc    50100
acatgtacac gcatgcacgc gcatacacac acgctcactc atgtaggcac cttctccgtg    50160
gggctcagca aataaatggc ctccagactg ggaatgggtt cccgccgttt gttgatgtct    50220
tcaacaacta gtaggaacag aggaagggac acaggtgggt ggcatccagg cagggccacg    50280
tggggagtct caggtgtggg gggttggagg cttggggagg aggggtggat gcttaggagg    50340
gactgcagga gaaacccact tagggaccac cagctaagag ccacacgaca gggttctgca    50400
ggggttgtgc agccaactgg gttccccaaa tttacagaca gggagactga ggttctgaga    50460
ggacaggctc cctcagcacc tatccctcaa tggcaaagtg actgggacac cacctggggt    50520
cacccataga aggctctgca ttcttgggac cccacatcca gagtccaccc tgggagtccc    50580
acacagggct ccacgaggga gctgcacggt caggaagggg ctgcagccag ggagtgctgc    50640
aggggaggcc tgcaatccat gggctcccgc agtcagcttg caaggtttaa gaatggattt    50700
ggtcacatga tccgggctgt ccgtgcaggg agctgcgtac ttgggagttc tggacgattt    50760
gaggggatcc tacactcaag ggctgaaccc tgggagaggg gcacagtcag gggttcccac    50820
gctcaggtcc catctcactg gggacgcgtt cactcactgg tgatgccctc agccaggata    50880
tctgacattt tgcagcagga agacaagatg cgcatgcttg ggtgatccat gataagcacc    50940
tgtccagatg gatggacaga tggatggagg agcaggcgga agaggccaca gctggcccca    51000
gaaggggcca aggcagtggg aggggcagtt tcaagggctg gctgggtggg aggacccaga    51060
acccattcac ccaactccac ccatgtggac aggcagttct tggggtccc acattcaggg    51120
tcttccccat aggcctgatg atgagctgcc tctgggtacc cagccatctg cctcacccct    51180
accttccact ccccatcctt cttgacactc cgaataactc cgctcagaat ttctgcaggg    51240
aagggagggg aggggtcaga atgctggttc tctggtccca ccactgcccc aagccttctc    51300
agccttgggg ctgaaccccc atcttaattc ccatttactt tttttttttt tttaagagag    51360
gaggatctca ctctgtcacc taggctaaag tgcagtggtg tgatcataac tcactgcggc    51420
ctccaactcc tgggctccag cgatcctctt gcctcagcct cccgagtagc tgggactaca    51480
ggtgcatgta ccacccacag ctaatttatt tttatttctg tatagatggg gtctcgctat    51540
gttgcccaag ctggtctcaa acttttggcc tcaagcagtc ctcctgcctc ggcctcccaa    51600
agtgctggga ttacaggtgt gagacacggc acaggaatca tttatttta gccccagtt    51660
ctgcaaattg gcttctgggg tcacccccaa tttacagaca gggaaacaga ttcttaggca    51720
acatgtaact cacctacgca tcctgagtgt ctaagtggca gagtgctggg gcaaaaggtg    51780
ccactcgata aacatgtttt aggtgaatga aagaggaga accgggatca tctacagctc    51840
tatctgcctc tagcgccagg ctctcggctt ccccacctgc tacctcaagt attcctgctg    51900
tgagggtttc agccagtccc cccaacctgg tctaaaatgt aggacccctg gttcccagct    51960
ctgaggcatg cctagctgag gctatcccac tgacctccgg tctcagtttc ctcatctgta    52020
aaatggaatc acttttttct aatctccccc aattaaaggg gtttgagcta cagaccgccc    52080
tgcctagagg agagagtgga gagaagtaac ggggtggccc cgcccagcca cgtccactgt    52140
gtcatgtcca ctgttatcaa gacggccagg gcggaaggag cagctgaggc cggaactccc    52200
cggggtggag gaagaggcgc cctccaccct tcccccaaga accggggccg gtgaggcctg    52260
gacgcctgcg tcctccagct gcaaggcgct cctggaaatg gggcaaggag gaagacatcc    52320
cctacaccac ccctgtgggg cctggacacg tcccctgagc gctcacagca cctagggtcg    52380
ctgaccagag ccctaggagg ccccaagaat ccagcccctg aactttgccc ggcttaagag    52440
```

```
atcctagagt gtgggcatcc agctgtgccc tcctccccg  gcaggcaccc taggaggccc   52500
aggagtccgg gccccagcct ccgccacact ctacccgtcc cctttgggtc cccggagtcc   52560 ggcccccaa  ttttgttctg ttctggcacc ggagagcagg ggcgtccagc tgggaacccg   52620
tccccgcccg cccctcgag  ggtcaggtgc tcggacgccc agcccggccc ccaactccca   52680
gccgccatga aacccaggat cccagagccc gtgcgtcccc gaccccgtc  ccacaccgga   52740 cgccagagcc cggccccgga gaggcactca ctttccccca ccaccgcctt cagccccgag   52800
ggcgccatct tccccgaggg gcgccgccgc cgcttccggg tgtgtcccaa ggtgggggcg   52860
tggccgcgcg tcacccacgt ggaccccgcc ccgcgccctg tccccgcccc ctgcgcacct   52920
ggcccctccc cgccgtcggt tctcgcccag gcccaggaag ttgagtccct ggcggggagg   52980
acgggcaggt gcgtccgcgc tgccgagcac gaagtcgctg gaggtgcaca cctcgacgac   53040
acgctcacag atgggagttc agacacacac ttcctggctt gcgtgcgaag caggatcgca   53100
gggcaataat ccctccatct tccccgggag gttctgtgcc tgcaagatac acggcaccca   53160
ctcgatgcca ccgggccgcc actgtctggg cctgggatct tgacccactt gccttctgta   53220
cttcagggtt tagaggcagc agcagcagca gcagccgtct tggataactt ttgatggatt   53280
caggaggcct ggagacctct tgtgtgcagg cacctggaca taattttcat tcagtcctgc   53340
ccaatgttcc gacctggact gcggtgccga cgaggaaacc gaggcttagc gggatccta   53400 atccaaggcc acgacgagtg agcctgctgg gttcaagcca ggagcctgtc ccagggggc   53460 atttgtcaca gccttaccct cttccggag  ggcgcaacgc ttaccctcgt ggaccaacaa   53520
tcgaattaac atgctgatac acacatgggg tgagtgacgc cctcaaatgc ttgcaaacac   53580
agacacacac tcggaatttc agaagctgct tctgctgtgt gtcctgtcgc ttggaaggca   53640
cagccccagc agcacccata caaaatgagg tctccgattt aaggtgcgag gtatgtgtgc   53700
aaacagactc ttgctggtct gagctggttc cttcgctcgg ccgtgttgat gaaggtacca   53760 agcccctgc  cacttacatg ggacataggg agtgaatcag acccgaaggt ctggggaga   53820 taggaaagga tccatgctgc cctaaaggaa ataaactaat gtgacaacaa gtgccacaga   53880
aggtaggggt gggagggac  tttactgagg atgaccccg  agggcctctc tgaagaagca   53940 gcctttgac  attatcccta aatgattct  agaagcagcc acacagcatg tccaggtaga   54000
gaagggagga gccccgagct taagaaggct ggagggtggg ggcagcaggg gccagacttc   54060
tgtaggacaa ggtcagactg acccatccca gtgccaggat gcaggacttt cagtgctaaa   54120
aataggacag tcacaggcaa accaggacgg ttggcaaccg taggtaggag tttgagctat   54180
ttcttccttt cctttccttt tcccttcctt tcttccttct tctccctcct ccccatttt   54240 gtttgttttt gttttgtaaa gagacgggtc tcgctctgtt gctcaggctg gagggcagtg   54300
gcacgatcat agctcactgc agcctcgact tcctgagctc aagggattct tccacttcgg   54360
ccacccaagt agctgggact acaggtgcac gccaccgtgc ccggttgatt ttgttgttgt   54420
tgttaagaga caggatctcc ctatgttgcc caggctggta tcaaactcct gggctcaagg   54480
gatcctcctg ccttggcctc ccaaagtgtt aggattttag gtatgagcca ccgcacgctg   54540
ccccttcctc cttttgtaac agctttactg agatataatt cacataccat acaactcgct   54600
gacctaaggt gcgtaagtca atggctttca gtattttgg  agttgtgtgt ccattaccac   54660
aatccatttt agaacatttc cacaacccct aggtgtttgg gttttgtctt ctcaagagtt   54720
ttgagcaggg gaaggcgggg aaccctccag atcctggggg gatggaagcc aggaccgcct   54780
```

```
ccagcttctc agcctgaccc cttgggggga cagagagctg ttagggccag ccaccccacc   54840
actaaccccc aaaagatatg aagtactaat ccccaatacc ccacaatagg atcttatttg   54900
aaatggggtt agtatagata ttagcagtga gcatgaggtc acactggagt agagtaggcc   54960
cctaatgcaa tatcactggt gtccttgtaa gatagttata tgtctgcctg gttctgtgta   55020
ggtggttggg ggggtgggga aatgggtata tgaagactgg gacacagagg gagaatgcca   55080
tgtgaccacg gaggcaggga gtgaagagct gcagtgacaa gccaaggaca tcaaggacgg   55140
caggccactg ccaaaagcca gggaggggca aggagggctc ctgagacctg gttttcagag   55200
ggagcacagc tctgccaaca ccttcatttc aggctgtggc ctctggaacg ttggctcaat   55260
aaatttgtta aaaaaaaatt ttaaaggctc agcatggtgg ctcatgcctg taatcccagc   55320
actttgggag gccaggcag gaggatcaca tgaacccagg agtttgagac tagcctgggc   55380
aaaatagtga gacctcatct ctatataaaa atatataaca aaagtcaact tatgtgtttt   55440
aagccatctg gtctatgaca ctttgttctg gcaggcctag gaaagggata cacgtactga   55500
ggaggggggac acttcattgg catagaggga gagagtgtga acttggcctt ttgtggaaca   55560
gaggaggctc gggcagaggt ggtgatagtg cagcccattc attctgagat gaaacttcca   55620
ctggtttccg taaaggcgtc ttggggaggg aagggaaggg gatgggggacc tcccagtggt   55680
atccctgct tgggcactga ggggaaagcca cagtggctcg ggggaaaagg cagggacgtc   55740
ctctccccgc ctgcctctgt ccccagggag tctcgcctcc tgttcccacc tggggctagg   55800
gtgatagagg agaggagata gctcaacctg gcatttaggt ggtgtgggaa caggagaccc   55860
cagactttct tgttttgggg tctggggcag gcaaccaggc tccagggaca gtgagttgaa   55920
ggaagggtgg ctgggagacc ccttgacttg ctgccaagga gacagagctg gagctagggt   55980
ggccggtggt gtctgaggca ggtgcagaga gggagggagg gaagggggcct ttgactccaa   56040
cctcctttttt ctgtaccgac tgcaggtggc agctgcccctt tcaggagcca gtgggggaac   56100
ctgggtggct gggtgggggac acctgcaagt cctccctaag ccagctacca ccctacactg   56160
ttggcctccc ttctccaact gtgggatgc tgctcaggcc ttttgtgaca tcacacctga   56220
gagtccctgg ggtccagtca ttgctgctgg gcacagcgag gtccaagctc aggtcgccct   56280
gccccctacc caccatgcca gatccagcat cgttgtgggc aaacaattat ctggatgatc   56340
tttatggggc ttaagcttgg gtgggagcag atggggcatg agctggggat ttggggatgg   56400
ggggaatcca caccccacg tcctggacgt ttaaaaggcc ctctctggca ctgggccggg   56460
gcagaggcca gcagaaaagt gactggagtc cagggacatg atggatcagg aggagaagac   56520
ggaggaaggc tcaggcccct gtgccgaggt gagagggccc tgccccacc ccaccccag   56580
ctcaaggtct cagagcccat gattgacaag actagtttgt agggcaccta attaacgagt   56640
gagtctccta ggacccctg acccagttgt ggctgtagaa agggggtggt gggcttgggg   56700
gtctgagtgc caggccccag ggcagagggc agggctctcc gtgtgacccc ctattgatgg   56760
gagatgctgg gacctggggg tagctcctgg gccatgtttc cctgattcgt gtcccagctc   56820
ccaggccaca ctcatcaggc cccaatctag gacggcggga cacgcatcgg agcctgtccc   56880
ttgaagcggt accacgtgaa gtggcactgc tggccagggc ccctggggcg ggggccggga   56940
ttgggaagga gactcatgtc tcattcagaa cagctctgca gagaggatcg gcggggacca   57000
tggtgagagc tgaggaagtg gggacggcag gccccggggt cagggtgtga gcaagctggc   57060
taggaagttt ggggagggc ccccaagctg aagggccaac cagactgagc gagtctgtcc   57120
ccaggcgggc tccccagacc aggagggctt cttcaatctg ctgagccacg tgcagggcga   57180
```

```
ccggatggag ggacagcgct gttcactgca agccgggccg ggccagacca ccaagagccg   57240
tgagcatggg cacggggagtg ctgtccatgg ggcgtgaacg gggtgggagt gcagggcaag   57300
tggtcatctg gagggcctgg gggcacggga tgtgggaggt ggttgtgcac cctgaagcat   57360
ctgtgtgggg gtgaagggt agggttgggg gcccccactc cggctgtgtc ctcccaagtc   57420
tgtgaacgtc cacgcagaga gcgacccccac ccccgagatg gacagcctca tggacatgct   57480
ggccagtacc cagggccgcc gcatggatga ccaacgtgtg acagtcagca cgctgcccgc   57540
ttccagcccg tggggtccaa ggtaggtgat gttctggcga tgtcgaggag aaacccgcca   57600
ggcagtgctc tccgatcctg ccctccaccc cagccaggag ggaacagggc ctgccccatc   57660
tctgtccatc cgctgccctg acttcagatg ggaggaccaa ggcccaggca gtggctagag   57720
gggcccaagg ttatacaggg gccatgctag tgtaagaccc atggctggaa cttgtggctc   57780
ctgcccccaa gtctgaaggt tctggggagg ccaaagggag aaaataggac cccttcctag   57840
gaaagtatcc caggaggaa gtcacgtaag ctcacacata ggatatatac atctgtatac   57900
tcacatctgt tgacttcaca catacacgaa gcttgggttc tgatcaagat cccagcgagg   57960
gccccaagac ctgccacctc acactcaaat gccaccctaa atggcagata ttgagggtaa   58020
acatagacca gtgctcacaa tgaggtggga cacggtggct acctgcaccc tctctccatt   58080
gttcgccacc tgtggccggc actgcccttg agccctcccc ctggctgacc cctcttcatc   58140
cacaggacgg agcacagaaa cgagctggga ccctcagtcc ccaacccctg ctcaccccct   58200
aggacccgac cgctctcggc ttccgtcgga acagcagccc ccagccccg acacaagccc   58260 cctgagggcc tgaggcatcc tgggtctcac tcggccccca aaaactgata aagaataaa   58320 acacttaaat gaataacaag gaactgagta tatgtatatt tcatcagggg aggggctagg   58380
actcccactt ggaggcctca ggagttctgc tgggcgtcgc gaaggagctt ctcctcccgc   58440
cgcttccgta acctctcttt gaattcctct atctcttgaa gctaggggtg gagaagcggg   58500
tgggacagga aggggggagg ggcacacacc tcagagccgg gacccccccc ccccgcccac   58560
ctctcccacc accctgcccc agaccacggc ttcagggttc agtgtcttca ctggaagccc   58620
cctgccaatt acaaaggggt ccgcgtggga tccgcttcac tcttccagga gaaggcaata   58680
aggaaaccat ctactcctct gctctcggtt ccttactcat ggctgagagt aaaatgtttc   58740
tttttgagac aaagtctcac tctattgccc aggctggagt gcagtggcgt gatcttgggc   58800
tcactgcaac ctccacctcc tgggttcaag tgattcttct ccctcagcct cccaagcagc   58860
tggaattata ggcgcctgcc accatgcctg gctaagtttt gtatttctgt agacatgggg   58920
tttcgccatg ttggccaggc tggttttgaa ctcctgacct caagtgatct acccacctca   58980
gcctcccatg ccctgggatt acaagcatga gccactgcgc ctggcctaaa attttcatct   59040
aaaacccatc ccggatacaa gaatccagcc tcctccatcc ctctggcagg aagaagagat   59100
cacttacctt ctcaggtggc cacagctccc tctgtaagga aaagtcacaa atgggacacg   59160
agccaaaggc ctccagagcc ccacatcagg gcagggtcgg cttatgggag gcagacatta   59220
gtccccagca gactgctgcc ccacaccctc tcccacccct ggaatgaacc ctcaaacact   59280
cctcttatgc ccaccttgcg ctgtatgaca tcgtcctcaa accactcggc ctgattggaa   59340
acccagaaca tagccacagg gaaagtgagg tagattatca tctggaatgg cagagggtgg   59400
gtgaggtgag ctcccccccaa gcaatgtgca gaggctcctc agagcctggg ggacccatcc   59460
tactgcagag tccagaagcg cctcgttacg gccgacccaa gaatcccaga actcccacca   59520
```

```
agggtacaga aacctcgcac cctaaaacct aactcctata atccaggagg cctcattcct   59580
gaaagttccc tctgagctgg agtcttcctc tcaaacacag acagacacac agacgcccca   59640
gctacaatca aaagcatctc ctcgagacct cattacccat ccccacttaa gatcccggga   59700
gcacccccaa acccaggagg cgtcactctt caactccact tctcgaagtc taggaatctc   59760
cctgtcatag acacccaccc accacgagcc cgagagctcc ccaggatct taagtcttcc    59820 ttctttagag ccccctttctc agctcacccc tctctgaggt ccttcctcgg accagccctc   59880
tcacagcccc caaaatcaga agcacaaatc cgagaacccc cccagcccag cgtcccctct   59940
cctggatttc caaccagaaa ggtcctctca aatcttaaga gctttctcct tggagctccc   60000
tcttcctttg aagtcccccc atttccaacc tcatcttcag atccaggaag atccctgcc    60060 cagcctccca acccactcct gtgtccactg acccgaaata tctccagctt caccccatc    60120 tcgtttctcc cggtcaacaa agccagttcc gcccaaagcc gaccctccag caagacagaa   60180
gctcactggt gttttgcacg ctccattgct gaagctgatt ggccaatgtg tatcctcatg   60240
gcgcatcttc tggcgcctct attctgcttc cggtcgctgg cgtcgtcgaa agaagtcaa    60300 taacgtgggc ctgtccgtca aaaatgattt aaccaataga aaacgggtct ggctcggagg   60360
ggcgggccgt cagtggtaga cgtcataagc gcgcgactct ctcctgtacc tgggcatcca   60420
gaaaaatggt ggtgatggcg cgactctcgc ggcccgagcg gccggacctt gtcttcgtga   60480
gtccacagag gagccggggg tggcctgcgt tggggcattg ggacctggac gccgcagggg   60540
atcgaggctg ggtcggcaag gagatttagg ccgaaactgc caggccaagg tctgggaacc   60600
ctaatgggcc agagaccgga tcgtcatgtc cgcaccgaac tgtccaggag taaaaatatg   60660
gtgttgtatc ttcgggtctg agtagaaaac cactgtcgaa gggaagcgtc tagcctcccg   60720 aaccagggggc ggaaatgggg gcgtgcaggg aatgggagag gaggaagatc gcataactga   60780
accttgagag gtgaagatcg gtgtctgaag taaaggcttg cttacgaggc cagggttctg   60840
gtttctggga tgaaggcttg gttttctgga tagcggtctc taggcctgga ctgcagcatg   60900
acagtttctg gggtggtggc caggctagaa gaaccctggt gatgtggagc ttgtcaggcg   60960
atggccagtg aaatacttac tctctggagt agaggcgtga catcttcacc agattcttgg   61020
tgtgcagagt taaggcttg gcttctggtg tataactcct cctgtgagat aaaggcctag   61080
cttttaattt ctggggcaga gttgagctag acgctggcta gtgggatcct gggggcgggg   61140
ctagtggctt ggaatctgga cctgagagcc ctggtggctg gggtaaagat ctggtcatct   61200
gggcctgggg tggagatggg tcagatggtg acagtggag tctgagggc aaaggcctgg     61260 tgtctgggaa gaggcacgtt ttgaagaagt ggggtctggt gtccaggact ggcatctggg   61320
ccagggcctt ggtatctaag gagtctgacc atctggggca gaaagcgagt ggtgatgcgg   61380
actcattcct ggcccagagc cctaatgact gagaagtctg atgatttggg ttcgattttg   61440
ggtagttgaa ttctgagggg taaggtctg ggccactgtc ttggtgtcgg gcatctggtt    61500
tggtgcctgg gcatctggtg acctgacttc cttggtgggt ggtgggatct aggtaaaagt   61560
ccggagtttg gacctgagcc ccagcagtgg gatggtgctg cacacaggct ctgagggtag   61620
gcctctcttc ttcccattcc ctggccctgg caggaggaag aggacctccc ctatgaggag   61680
gaaatcatgc ggaaccaatt ctctgtcaaa tgctggcttc gctacatcga gttcaaacag   61740
ggcgccccga agcccaggct caatcagcta tacgagcggg cactcaagct gctgccctgc   61800
aggtgggaat ggctccagct gccctgccca ccagccccca ccccacctgg tccagttata   61860
acaaaactgc caagtgggtc ccgggtcccg ggtgattgct tcgtgtttca tcactgacct   61920
```

```
gtacatccct tgatgggtca gcacaccttc tctgatgtcc cagtctgtcc ctgtcattgc    61980
tgagacatgt caccectccc acacccette ttcccacatt tgccaactgg ggcagggcaa    62040
atggttctgg gggtgtccat aaagctgacc gatcagcatc tgtccctcc tattccccag    62100 ctacaaactc tggtaccgat acctgaaggc gcgtcgggca caggtgaagc atcgctgtgt    62160
gaccgaccct gcctatgaag atgtcaacaa ctgtcatgag agggcctttg tgttcatgca    62220
caaggtttgg ggctcggcga ggggatgaat cgggaagtgg agctcagtcc atggtggtgg    62280
gtggggcggg gacaggggct gggctcagca tgttagggat gggggcttgg attcctgttg    62340 cttcttttgca tgggaagttg ggctggactc agtcctggag ctgggggttt ctgggtcccg    62400 ccgcattat gtggtggccc caggtgtggc tcagccacag gacatcgagt gtctgtggcc    62460
aggccatgga gtccgtggct tagccccagc cgcctctccc cacaccccca gatgcctcgt    62520
ctgtggctag attactgcca gttcctcatg gaccaggggc gcgtcacaca cacccgccgc    62580
accttcgacc gtgccctccg ggcactgccc atcacgcagc actctcgaat ttggcccctg    62640
tatctgcgct tcctgcgctc acacccactg cctgagacag ctgtgcgagg ctatcggcgc    62700
ttcctcaagg tgagcctagc aggtgcgctg gttccccagg ttagtttcca gaaacggcct    62760
cactgtgaca ctagctccgt gtaggatgtc acccagcaga cgggatgtgg gaagaggctc    62820
ctggagatgc atgtgttttg ttgttgtccg tgattcatgt cttatttttc caaatagttt    62880
gttcacactg gttcacatt aggcatagcg atgggtgctg aggacagtgt gactaagaca    62940
ctccctgcct gcacggagct tttagtctaa ctaggaagac agatgcatat gagctgatgg    63000
catgaactag agtaaaacca cagccatgaa gagggccagg aataagggtg gggagaagca    63060
ggcagggtgg agagtggaag caccagccgg gcggagtgg ggcatggttt gctcaaactt    63120
aaagtatctg ttttatgacg tttggattct aagctggacc agtcaggact gaggctggac    63180
ccgtggggcc caggctggac actatagtca aggctggacc catgggatca aggctgaccc    63240 aaagggggcca aggctagacc agtcaggact gaggctggac tagtggagcc aaggctggac    63300
ccattgtggg ttgggggtca attctaaccc aaaaggacca aggctggacc attgggggtg    63360
agactggacc accgcagtca aggctgtgcc cttgcgggtc aaggctaacc caaaaagtcc    63420
acagctggtc tagtcaggac tgaggctgga ccagtggagc caaggcagga cccacagggg    63480
gttgagccta acccagtggg gccaaggcta gaccagtagg aaccgggctg gaccagtggg    63540
gctgaggctg gtttgacagg gcttgctttt gcccaagaca ctcataaatg ggtggggggg    63600
gacgccccga agccactgaa tcgggaggtg ggcgtagccc tgccaccca ctgactgcct    63660 gagggggtggc tcggtcccca gctgagtcct gagagtgcag aggagtacat tgagtacctc    63720
aagtcaagtg accggctgga tgaggccgcc cagcgcctgg ccaccgtggt gaacgacgag    63780
cgtttcgtgt ctaaggccgg caagtccaac taccaggtgg gcctgccggg agccggcaac    63840
tgggtgggag ggccacccc tccatgactg agcctgagac tctcccccac tgccccatgc    63900
cctgcagctg tggcacgagc tgtgcgacct catctcccag aatccggaca aggtacagtc    63960
cctcaatgtg gacgccatca tccgcggggg cctcacccgc ttcaccgacc agctgggcaa    64020
gctctggtgt tctctcgccg actactacat ccgcagcggc catttcgaga aggtgcatgc    64080
tggcacacgg ggctctgggt tcggggcggg gtctccctcc gacactcggg gacacatgtt    64140
gacacatgca cagacagaaa acatgccatt tatggctggg tgtggtggct cacacctgtc    64200
atcccagcac tttgggaggc cgaggcggta ggatcacttg aggtcagcag ttcaagacca    64260
```

-continued

```
gcctggccaa catggtgaaa ccccatcact actaaaaata caaaaattag tcagacatgg  64320
tggtgcgcgc ctgtaatccc agctactcgg gaggctgagg caggagaatc gcttgaactt  64380
gggaggtgga ggttgccgtg agctgcgatc gcgccacgga agtccagcct gggtggcaga  64440
gcgagactcc atctcaaaaa aaaaaaaaaa aaaaaaaagt gccatttttg acagacatgc  64500
atatccctgc acacgattac tatcctgctg agggtggggg agcactcctg cccgcaagca  64560
cgtcagcctt tggagttcag ccacattttg cgttcagggt ttcaccctct tggctctgcg  64620
gcctttgccc caactaaggg tggtttgttc tttcatttgt aaaaatcagg gtgacagttt  64680
actgccttgt caccaatcag                                              64700
```